(12) United States Patent
Abel et al.

(10) Patent No.: US 11,981,739 B2
(45) Date of Patent: May 14, 2024

(54) CHIMERIC ANTIGEN RECEPTOR SPECIFIC FOR INTERLEUKIN-23 RECEPTOR

(71) Applicant: SANGAMO THERAPEUTICS FRANCE, Valbonne Sophia Antipolis (FR)

(72) Inventors: Tobias Abel, Antibes (FR); Julie Gertner-Dardenne, Grasse (FR); François Meyer, Porrentruy (CH)

(73) Assignee: SANGAMO THERAPEUTICS FRANCE, Valbonne Sophia Antipolis (FR)

( * ) Notice: Subject to any disclaimer, the term of this patent is extended or adjusted under 35 U.S.C. 154(b) by 884 days.

(21) Appl. No.: 17/047,232

(22) PCT Filed: Apr. 15, 2019

(86) PCT No.: PCT/EP2019/059590
§ 371 (c)(1),
(2) Date: Oct. 13, 2020

(87) PCT Pub. No.: WO2019/197678
PCT Pub. Date: Oct. 17, 2019

(65) Prior Publication Data
US 2021/0380704 A1  Dec. 9, 2021

Related U.S. Application Data
(60) Provisional application No. 62/657,233, filed on Apr. 13, 2018.

(51) Int. Cl.
| | | |
|---|---|---|
| *C07K 14/705* | (2006.01) | |
| *A61K 35/17* | (2015.01) | |
| *A61P 17/00* | (2006.01) | |
| *A61P 29/00* | (2006.01) | |
| *C07K 14/725* | (2006.01) | |
| *C07K 16/28* | (2006.01) | |
| *C12N 5/0783* | (2010.01) | |

(52) U.S. Cl.
CPC .......... *C07K 16/2866* (2013.01); *A61K 35/17* (2013.01); *A61P 17/00* (2018.01); *A61P 29/00* (2018.01); *C07K 14/7051* (2013.01); *C07K 14/70517* (2013.01); *C07K 14/70578* (2013.01); *C12N 5/0637* (2013.01); *C07K 2317/622* (2013.01); *C07K 2319/02* (2013.01); *C07K 2319/03* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | |
|---|---|---|
| 4,816,567 A | 3/1989 | Cabilly et al. |
| 5,350,674 A | 9/1994 | Boenisch et al. |
| 5,585,362 A | 12/1996 | Wilson |
| 5,858,358 A | 1/1999 | June et al. |
| 5,883,223 A | 3/1999 | Gray |
| 6,326,193 B1 | 12/2001 | Liu et al. |
| 6,352,694 B1 | 3/2002 | June et al. |
| 6,534,055 B1 | 3/2003 | June et al. |
| 6,692,964 B1 | 2/2004 | June et al. |
| 6,703,199 B1 | 3/2004 | Koide |
| 6,797,514 B2 | 9/2004 | Berenson et al. |
| 6,867,041 B2 | 3/2005 | Berenson et al. |
| 6,905,680 B2 | 6/2005 | June et al. |
| 6,905,681 B1 | 6/2005 | June et al. |
| 6,905,874 B2 | 6/2005 | Berenson et al. |
| 7,067,318 B2 | 6/2006 | June et al. |
| 7,144,575 B2 | 12/2006 | June et al. |
| 7,172,869 B2 | 2/2007 | June et al. |
| 7,175,843 B2 | 2/2007 | June et al. |
| 7,232,566 B2 | 6/2007 | June et al. |
| 8,697,359 B1 | 4/2014 | Zhang |
| 8,771,945 B1 | 7/2014 | Zhang |
| 8,795,965 B2 | 8/2014 | Zhang |
| 8,906,682 B2 | 9/2014 | June et al. |
| 8,865,406 B2 | 10/2014 | Zhang et al. |
| 8,871,445 B2 | 10/2014 | Cong et al. |
| 2004/0101519 A1 | 5/2004 | June et al. |
| 2006/0034810 A1 | 2/2006 | Riley et al. |
| 2006/0121005 A1 | 6/2006 | Berenson et al. |
| 2006/0200869 A1 | 9/2006 | Naldini et al. |
| 2007/0036773 A1 | 2/2007 | Cooper et al. |

(Continued)

FOREIGN PATENT DOCUMENTS

| | | |
|---|---|---|
| WO | 2001029058 A1 | 4/2001 |
| WO | 2001096584 A3 | 12/2001 |

(Continued)

OTHER PUBLICATIONS

Frieder et al. (Clin Pharmacol Ther. 2018;103(1):88-101). (Year: 2018).*

(Continued)

*Primary Examiner* — Zachary S Skelding

(74) *Attorney, Agent, or Firm* — Z. Ying Li; Wyan-Ching M. Lee

(57) ABSTRACT

The present invention relates to a chimeric antigen receptor (CAR) specific for an IL-23 receptor, and to a nucleic acid encoding the same. The present invention further relates to a T cell expressing said CAR, and to the use thereof for treating an autoimmune and/or inflammatory disease or disorder.

20 Claims, 5 Drawing Sheets

Specification includes a Sequence Listing.

(56) References Cited

U.S. PATENT DOCUMENTS

| | | | |
|---|---|---|---|
| 2010/0135974 A1* | 6/2010 | Eshhar | A61K 39/0008 |
| | | | 435/375 |
| 2011/0158957 A1 | 6/2011 | Bonini et al. | |
| 2012/0060230 A1 | 3/2012 | Collingwood et al. | |
| 2014/0068797 A1 | 3/2014 | Doudna et al. | |
| 2014/0370017 A1 | 12/2014 | June et al. | |
| 2015/0329637 A1* | 11/2015 | Urech | A61P 35/02 |
| | | | 424/135.1 |
| 2016/0024470 A1 | 1/2016 | Aarvak et al. | |
| 2018/0348227 A1 | 12/2018 | Sadelain et al. | |
| 2020/0283529 A1* | 9/2020 | Levings | C07K 14/70578 |

FOREIGN PATENT DOCUMENTS

| | | |
|---|---|---|
| WO | 2007110785 A2 | 10/2007 |
| WO | 2012138475 A1 | 10/2012 |
| WO | 2013/059593 A1 | 4/2013 |
| WO | 2014180577 A1 | 11/2014 |
| WO | 2015172800 A1 | 11/2015 |
| WO | 2016055551 | 4/2016 |
| WO | 2016184570 A1 | 11/2016 |
| WO | 2017165245 | 9/2017 |
| WO | 2017173410 A1 | 10/2017 |
| WO | 2017/216561 A1 | 12/2017 |
| WO | 2017210749 A1 | 12/2017 |
| WO | 2018001874 | 1/2018 |
| WO | 2018224443 A1 | 12/2018 |

OTHER PUBLICATIONS

Hanzel et al. (Expert Opinion on Biological Therapy, 20:4, 399-406 (2019)). (Year: 2019).*
Petermann et al. (Immunity. Sep. 24, 2010;33(3):351-63, supplemental information pp. 1-6). (Year: 2010).*
Papotto (EMBO Reports (2017) 18: 1957-1967). (Year: 2017).*
Miralles et al. (Neurotherapeutics (2017) 14:1095-1106). (Year: 2017).*
Lee et al. (JCI Insight. 2017;2(17):e91663). (Year: 2017).*
Dai et al. (J Immunol (2017) 199 (3): 903-910). (Year: 2017).*
Pepple et al. (Ophthalmology 2018;125:1977-1983). (Year: 2018).*
Dawson et al. (Front. Immunol. 8:1460 (2017)). (Year: 2017).*
Hawkes et al., J Allergy Clin Immunol 2017;140:645-53. (Year: 2017).*
Tsai et al., Ther Adv Musculoskel Dis., 2017, vol. 9(11) 277-294. (Year: 2017).*
Emilie Duvallet et al., "Interleukin-23: a key cytokine in inflammatory diseases", Annals of Medicine, Nov. 2011, vol. 43, No. 7, pp. 503-511 (9 pp.), doi: 10.3109/07853890.2011.577093.
Andrew J Wood et al., "Targeted genome editing across species using ZFNs and TALENs", NIH Public Access Author Manuscript, Science, Jul. 15, 2011, vol. 333, No. 6040, pp. 307, doi: 10.1126/science.1207773.
B Al-Lazikani et al., "Standard conformations for the canonical structures of immunoglobulins", Journal of Molecular Biology, Nov. 7, 1997, vol. 273, No. 4, pp. 927-948 (22 pp.), doi: 10.1006/jmbi.1997.1354.
Barry L Stoddard, "Homing endonucleases: from microbial genetic invaders to reagents for targeted DNA modification", HHS Public Access Author Manuscript, Structure, Jan. 12, 2011, vol. 19, No. 1, pp. 7-15 (9 pp.), doi: 10.1016/j.str.2010.12.003.
Benjamin S Jones et al., "Improving the safety of cell therapy products by suicide gene transfer", Frontiers in Pharmacology, Nov. 27, 2014, vol. 5, Article 254 (8 pp.), doi: 10.3389/fphar.2014.00254.
Blake Wiedenheft et al., "RNA-guided genetic silencing systems in bacteria and archaea", Nature, Feb. 15, 2012, vol. 482, No. 7385, pp. 331-338 (8 pp.), doi: 10.1038/nature10886.
Brett Chevalier et al., "Flexible DNA target site recognition by divergent homing endonuclease isoschizomers I-CreI and I-MsoI", Journal of Molecular Biology, May 30, 2003, vol. 329, No. 2, pp. 253-269 (17 pp.), doi: 10.1016/s0022-2836(03)00447-9.
Brett Chevalier et al., "The LAGLIDADG Homing Endonuclease Family", 2005, In: Belfort M., Wood D.W., Stoddard B.L., Derbyshire V. (eds) Homing Endonucleases and Inteins. Nucleic Acids and Molecular Biology, vol. 16. Springer, Berlin, Heidelberg., pp. 33-47 (15 pp.), https://doi.org/10.1007/3-540-29474-0_3.
Brian G Feagan et al., "Ustekinumab as Induction and Maintenance Therapy for Crohn's Disease", The New England Journal of Medicine, Nov. 17, 2016, vol. 375, No. 20, pp. 1946-1960 (15 pp.), doi: 10.1056/NEJMoa1602773.
Carl H June, "Adoptive T cell therapy for cancer in the clinic", Journal of Clinical Investigation, Jun. 2007, vol. 117, No. 6, pp. 1466-1476 (11 pp.), doi: 10.1172/JCI32446.
Dana Carroll, "Genome engineering with zinc-finger nucleases", Genetics Society of America, Aug. 2011, vol. 188, No. 4, pp. 773-782 (10 pp.), doi: 10.1534/genetics.111.131433.
Dirk Hockemeyer et al., "Genetic engineering of human pluripotent cells using TALE nucleases", HHS Public Access Author Manuscript, Nature Biotechnology, Jul. 7, 2011, vol. 29, No. 8, pp. 731-734 (4 pp.), doi: 10.1038/nbt.1927.
Durga Sivanesan et al., "IL23R (Interleukin 23 Receptor) variants protective against inflammatory bowel diseases (IBD) display loss of function due to impaired protein stability and intracellular trafficking", Journal of Biological Chemistry, Apr. 15, 2016, vol. 291, No. 16, pp. 8673-8685 (13 pp.), doi: 10.1074/jbc.M116.715870.
E A Kabat and T T Wu, "Identical V region amino acid sequences and segments of sequences in antibodies of different specificities. Relative contributions of VH and VL genes, minigenes, and complementarity-determining regions to binding of antibody-combining sites", Journal of Immunology, Sep. 1, 1991, vol. 147, No. 5, pp. 1709-1719 (11 pp.), PMID: 1908882.
E T Schenborn and R C Mierendorf Jr, "A novel transcription property of SP6 and T7 RNA polymerases: dependence on template structure" Nucleic Acids Research, Sep. 11, 1985, vol. 13, No. 17, pp. 6223-6236 (14 pp.), doi: 10.1093/nar/13.17.6223.
Ebby G Simon et al., "Ustekinumab for the treatment of Crohn's disease: can it find its niche?", Therapeutic Advances in Gastroenterology, Jan. 2016, vol. 9, No. 1, pp. 26-36 (11 pp.), doi: 10.1177/1756283X15618130.
Elena Provasi et al., "Editing T cell specificity towards leukemia by zinc finger nucleases and lentiviral gene transfer", HHS Public Access Author Manuscript, Nature Medicine, May 2012, vol. 18, No. 5, pp. 807-815 (9 pp.), doi: 10.1038/nm.2700.
Elizabeth Pennisi, "The CRISPR craze", Science, Aug. 23, 2013, vol. 341, No. 6148, pp. 833-836 (4 pp.), doi: 10.1126/science.341.6148.833.
Feidi Chen et al., "mTOR Mediates IL-23 Induction of Neutrophil IL-17 and IL-22 Production" Journal of Immunology, May 15, 2016, vol. 196, No. 10, pp. 4390-4399 (10 pp.), doi: 10.4049/jimmunol.1501541.
Feng Zhang et al., "Programmable Sequence-Specific Transcriptional Regulation of Mammalian Genome Using Designer TAL Effectors", HHS Public Access Author Manuscript, Nature Biotechnology, Feb. 2011, vol. 29, No. 2, pp. 149-153 (5 pp.), doi: 10.1038/nbt.1775.
Annette M Griffin and Hugh G Griffin "Computer Analysis of Sequence Data, Parts I and II". 1994, Humana Press, New Jersey. (392 pp and 456 pp). $59.50 each part (comb bound). ISBN: 0-89603-246-9 (pt. 1), 0-89603-276-0 (pt. 2) . . . Journal of Evolutionary Biology, 7: 628-629.
G Kohler and C Milstein, "Continuous cultures of fused cells secreting antibody of predefined specificity", Nature, Aug. 7, 1975, vol. 256, No. 5517, pp. 495-497 (3 pp.), doi: 10.1038/256495a0.
Genovega A Nacheva and Alfredo Berzal-Herranz, "Preventing nondesired RNA-primed RNA extension catalyzed by T7 RNA polymerase", European Journal of Biochemistry, Apr. 2003, vol. 270, No. 7, pp. 1458-1465 (8 pp.), doi: 10.1046/j.1432-1033.2003.03510.x.
H Jorn Bovenschen et al., "Foxp3+ regulatory T cells of psoriasis patients easily differentiate into IL-17A-producing cells and are found in lesional skin", Journal of Investigative Dermatology, Sep. 2011, vol. 131, No. 9, pp. 1853-1860 (8 pp.), doi: 10.1038/jid.2011.139.

(56) References Cited

OTHER PUBLICATIONS

Hiroki Torikai et al., "Toward eliminating HLA class I expression to generate universal cells from allogeneic donors", Blood, Aug. 22, 2013, vol. 122, No. 8, pp. 1341-1349 (9 pp.), doi: 10.1182/blood-2013-03-478255.

I J ten Berge et al., "Selective expansion of a peripheral blood CD8+ memory T cell subset expressing both granzyme B and L-selectin during primary viral infection in renal allograft recipients", Transplantation Proceedings, Dec. 1998, vol. 30, No. 8, pp. 3975-3977 (3 pp.), doi: 10.1016/s0041-1345(98)01309-8.

Ibtissem Grissa et al., "CRISPRFinder: a web tool to identify clustered regularly interspaced short palindromic repeats", Nucleic Acids Research, Jul. 2007, vol. 35, (Web Server issue), W52-W57 (6 pp.), doi: 10.1093/nar/gkm360.

J B Haanen et al., "Selective expansion of cross-reactive CD8(+) memory T cells by viral variants", Journal of Experimental Medicine, Nov. 1, 1999, vol. 190, No. 9, pp. 1319-1328 (10 pp.), doi: 10.1084/jem.190.9.1319.

J Bitinaite et al., "FokI dimerization is required for DNA cleavage", Proceedings of the National Academy of Sciences of the United States of America, Sep. 1, 1998, vol. 95, No. 18, pp. 10570-10575 (6 pp.), doi: 10.1073/pnas.95.18.10570.

J D Marks et al., "By-passing immunization. Human antibodies from V-gene libraries displayed on phage", Journal of Molecular Biology, Dec. 5, 1991, vol. 222, No. 3, pp. 581-597 (17 pp.), doi: 10.1016/0022-2836(91)90498-u.

J Devereux et al., "A comprehensive set of sequence analysis programs for the VAX", Nucleic Acids Research, Jan. 11, 1984, vol. 12, No. 1 Pt 1, pp. 387-395 (9 pp.), doi: 10.1093/nar/12.1part1.387.

J S Huston et al., "Protein engineering of antibody binding sites: recovery of specific activity in an anti-digoxin single-chain Fv analogue produced in *Escherichia coli*", Proceedings of the National Academy of Sciences of the United States of America, Aug. 1988, vol. 85, No. 16, pp. 5879-5883, doi: 10.1073/pnas.85.16.5879.

J Sethuraman et al., "Genes within genes: multiple LAGLIDADG homing endonucleases target the ribosomal protein S3 gene encoded within an rnl group I intron of Ophiostoma and related taxa", Molecular Biology and Evolution, Oct. 2009, vol. 26, No. 10, pp. 2299-2315 (17 pp.), doi: 10.1093/molbev/msp145.

J Stepinski et al., "Synthesis and properties of mRNAs containing the novel 'anti-reverse' cap analogs 7-methyl(3'-O-methyl)GpppG and 7-methyl (3'-deoxy)GpppG", RNA, Oct. 2001, vol. 7, No. 10, pp. 1486-1495 (10 pp.).

Jacob Z Dalgaard et al., "Statistical modeling and analysis of the LAGLIDADG family of site-specific endonucleases and identification of an intein that encodes a site-specific endonuclease of the HNH family", Nucleic Acids Research, Nov. 15, 1997, vol. 25, No. 22, pp. 4626-4638 (13 pp.), doi: 10.1093/nar/25.22.4626.

Jeffery C Miller et al., "A TALE nuclease architecture for efficient genome editing", Nature Biotechnology, Feb. 2011, vol. 29, No. 2, pp. 143-148 (6 pp.), doi: 10.1038/nbt.1755.

Jens Boch et al., "Breaking the code of DNA binding specificity of TAL-type III effectors", Science, Dec. 11, 2009, vol. 326, No. 5959, pp. 1509-1512 (4 pp.), doi: 10.1126/science.1178811.

Jens Boch, "TALEs of genome targeting", Nature Biotechnology, Feb. 2011, vol. 29, No. 2, pp. 135-136 (2 pp.), doi: 10.1038/nbt.1767.

Jing Guo et al., "Directed evolution of an enhanced and highly efficient FokI cleavage domain for zinc finger nucleases", HHS Public Access Author Manuscript, Journal of Molecular Biology, Jul. 2, 2010, vol. 400, No. 1, pp. 96-107 (12 pp.), doi: 10.1016/j.jmb.2010.04.060.

Karen E Flick et al., "DNA binding and cleavage by the nuclear intron-encoded homing endonuclease I-PpoI", Nature, Jul. 2, 1998, vol. 394, No. 6688, pp. 96-101 (6 pp.), doi: 10.1038/27952.

Kira S Makarova et al., "A putative RNA-interference-based immune system in prokaryotes: computational analysis of the predicted enzymatic machinery, functional analogies with eukaryotic RNAi, and hypothetical mechanisms of action", Biology Direct, Mar. 16, 2006, vol. 1, Article 7 (26 pp.), doi: 10.1186/1745-6150-1-7.

Kulemzin et al., "Engineering Chimeric Antigen Receptors," Acta Naturae (2017) 9(1(32)):6-14.

Long et.al., "4-1BB Costimulation Ameliorates T Cell Exhaustion Induced by Tonic Signaling of Chimeric Antigen Receptors," Nat Med. (2015) 21(6):580-90.

Shi et.al., "Chimeric Antigen Receptor for Adoptive Immunotherapy of Cancer: Latest Research and Future Prospects," Molecular Cancer (2014) 13:219.

Lipowska-Bhalla et.al., "Targeted Immunotherapy of Cancer with CAR T Cells: Achievements and Challenges," Cancer Immunol Immunotherapy (2012) 61:953-62.

Zhang et.al., "Engineering CAR-T Cells," Biomarker Research (2017) 5:22.

Huston et.al., "Protein Engineering of Single-Chain Fv Analogs and Fusion Proteins," Methods in Enzymology (1991) 203:46-50.

Muller et al., "Spliceosomal Peptide P140 for Immunotherapy of Systemic Lupus Erythematosus: Results of an Early Phase II Clinical Trial," Arthritis & Rheumatism (2008) 58(12): 3873-883.

Wegmann, "Targeting Cytokines in Asthma Therapy: Could IL-37 be a Solution?," Expert Review of Respiratory Medicine (2017) 11(9):675-77.

Kochenderfer et al., "Construction and Preclinical Evaluation of an anti-CD19 Chimeric Antigen Receptor," J Immonother. (2009) 32(7):689-702.

Boardman et al., "Antigen-Specificity Using Chimeric Antigen Receptors: The Future of Regulatory T-Cell Therapy?," Biochemical Society Transactions (2016) 44(2):342-8.

Michel Szczepek et al., "Structure-based redesign of the dimerization interface reduces the toxicity of zinc-finger nucleases", Nature Biotechnology, Jul. 2007, vol. 25, No. 7, pp. 786-793 (8 pp.), doi: 10.1038/nbt1317.

Michelle Scalley-Kim et al., "Coevolution of a homing endonuclease and its host target sequence", HHS Public Access Author Manuscript, Journal of Molecular Biology, Oct. 5, 2007, vol. 372, No. 5, pp. 1305-1319 (15 pp.), doi: 10.1016/j.jmb.2007.07.052.

Narayanasamy Elango et al., "Optimized transfection of mRNA transcribed from a d(A/T)100 tail-containing vector", Biochemical and Biophysical Research Communications, May 13, 2005, vol. 330, No. 3, pp. 958-966 (9 pp.), doi: 10.1016/j.bbrc.2005.03.067.

Nicolas Cougot et al., "'Cap-tabolism'", Trends in Biochemical Sciences, Aug. 2004, vol. 29, No. 8, pp. 436-444 (9 pp.), doi: 10.1016/j.tibs.2004.06.008.

P T Jones et al., "Replacing the complementarity-determining regions in a human antibody with those from a mouse", Nature, May 29-Jun. 4, 1986, vol. 321, No. 6069, pp. 522-525 (4 pp.), doi: 10.1038/321522a0.

Philipp Holliger and Peter J Hudson, "Engineered antibody fragments and the rise of single domains", Nature Biotechnology, Sep. 2005, vol. 23, No. 9, pp. 1126-1136 (11 pp.), doi: 10.1038/nbt1142.

Philippe Horvath and Rodolphe Barrangou, "CRISPR/Cas, the immune system of bacteria and archaea", Science, Jan. 8, 2010, vol. 327, No. 5962, pp. 167-170 (4 pp.), doi: 10.1126/science.1179555.

R E Bird et al., "Single-chain antigen-binding proteins", Science, Oct. 21, 1988, vol. 242, No. 4877, pp. 423-426 (4 pp.), doi: 10.1126/science.3140379.

R J Garland et al., "The use of Teflon cell culture bags to expand functionally active CD8+ cytotoxic T lymphocytes", Journal of Immunological Methods, Jul. 30, 1999, vol. 227, No. 1-2, pp. 53-63 (11 pp.), doi: 10.1016/s0022-1759(99)00068-x.

René Geissler et al., "Transcriptional Activators of Human Genes with Programmable DNA-Specificity", PLoS ONE, 2011, vol. 6, No. 5, Article e19509 (7 pp.), doi: 10.1371/journal.pone.0019509.

Rodolphe Barrangou et al., "CRISPR provides acquired resistance against viruses in prokaryotes", Science, Mar. 23, 2007, vol. 315, No. 5819, pp. 1709-1712 (4 pp.), doi: 10.1126/science.1138140.

Ryo Takeuchi et al., "Engineering of customized meganucleases via in vitro compartmentalization and in cellulo optimization", HHS Public Access Author Manuscript, Methods in Molecular Biology, 2015, vol. 1239, pp. 105-132, doi: 10.1007/978-1-4939-1862-1_6.

S F Altschul et al., "Basic local alignment search tool", Journal of Molecular Biology, Oct. 5, 1990, vol. 215, No. 3, pp. 403-410 (8 pp.), doi: 10.1016/S0022-2836(05)80360-2.

(56) References Cited

OTHER PUBLICATIONS

Sandrine Boissel et al., "MegaTALs: a rare-cleaving nuclease architecture for therapeutic genome engineering", Nucleic Acids Research, Feb. 2014, vol. 42, No. 4, pp. 2591-2601 (11 pp.), doi: 10.1093/nar/gkt1224.
S-h Kan et al., "Identification and characterization of multiple splice forms of the human interleukin-23 receptor alpha chain in mitogen-activated leukocytes", Genes and Immunity, Oct. 2008, vol. 9, No. 7, pp. 631-639 (9 pp.), doi: 10.1038/gene.2008.64.
Shengdar Q Tsai et al., "Dimeric CRISPR RNA-guided FokI nucleases for highly specific genome editing", HHS Public Access Author Manuscript, Nature Biotechnology, Jun. 2014, vol. 32, No. 6, pp. 569-576 (8 pp.), doi: 10.1038/nbt.2908.
Sofia Mumtaz et al., "Design of liposomes for circumventing the reticuloendothelial cells", Glycobiology, Nov. 1991, vol. 1, No. 5, pp. 505-510 (6 pp.), doi: 10.1093/glycob/1.5.505.
T Clackson et al., "Making antibody fragments using phage display libraries", Nature, Aug. 15, 1991, vol. 352, No. 6336, pp. 624-628 (5 pp.), doi: 10.1038/352624a0.
Tomas Cermak et al., "Efficient design and assembly of custom TALEN and other TAL effector-based constructs for DNA targeting", Nucleic Acids Research, Jul. 2011, vol. 39, No. 12, Article e82 (11 pp.), doi: 10.1093/nar/gkr218.
Toni Cathomen and J Keith Joung, "Zinc-finger nucleases: the next generation emerges", Molecular Therapy, Jul. 2008, vol. 16, No. 7, pp. 1200-1207 (8 pp.), doi: 10.1038/mt.2008.
Wida Razawy et al., "The role of IL-23 receptor signaling in inflammation-mediated erosive autoimmune arthritis and bone remodeling", European Journal of Immunology, Feb. 2018, vol. 48, No. 2, pp. 220-229 (10 pp.), doi: 10.1002/eji.201646787.
Y G Kim et al., "Hybrid restriction enzymes: zinc finger fusions to Fok I cleavage domain", Proceedings of the National Academy of Sciences of the United States of America, Feb. 6, 1996, vol. 93, No. 3, pp. 1156-1160 (5 pp.), doi: 10.1073/pnas.93.3.1156.
Yannick Doyon et al., "Enhancing zinc-finger-nuclease activity with improved obligate heterodimeric architectures", Nature Methods, Jan. 2011, vol. 8, No. 1, pp. 74-79 (6 pp.), doi: 10.1038/nmeth.1539.
Yaxiong Deng et al. "The Inflammatory Response in Psoriasis: a Comprehensive Review", Clinical Reviews in Allergy & Immunology, Jun. 2016, vol. 50, No. 3, pp. 377-389 (13 pp.), doi: 10.1007/s12016-016-8535-x.
International search report issued for WO2019/197678.
Koyle T Roybal et al., "Precision tumor recognition by T cells With combinatorial antigen-sensing circuits", Cell, Feb. 11, 2016, vol. 164, No. 4, pp. 770-779 (10 pp.), doi: 10.1016/j.cell.2016.01.011.
L G Presta, "Antibody engineering", Current Opinion in Structural Biology, Aug. 1992, vol. 3, No. 4, pp. 394-398 (5 pp.), doi: 10.1016/0958-1669(92)90168-i.
Le Cong et al., "Multiplex genome engineering using CRISPR/Cas systems", HHS Public Access Author Manuscript, Science, Feb. 15, 2013, vol. 339, No. 6121, pp. 819-823 (5 pp.), doi: 10.1126/science.
Luciano A Marraffini and Erik J Sontheimer, "CRISPR interference limits horizontal gene transfer in staphylococci by targeting DNA", HHS Public Access Author Manuscript, Science, Dec. 19, 2008, vol. 322, No. 5909, pp. 1843-1845 (3 pp.), doi: 10.1126/science.1165771.
Luting Yang et al., "Impaired function of regulatory T cells in patients with psoriasis is mediated by phosphorylation of STAT3", Journal of Dermatological Science, Feb. 2016, vol. 81, No. 2, pp. 85-92 (8 pp.), doi: 10.1016/j.jdermsci.2015.11.007.
Lutz Riechmann et al., "Reshaping human antibodies for therapy", Nature, Mar. 24, 1988, vol. 332, No. 6162, pp. 323-327 (5 pp.), doi: 10.1038/332323a0.
Makiya Nishikawa and Leaf Huang, "Nonviral vectors in the new millennium: delivery barriers in gene transfer", Human Gene Therapy, May 20, 2001; vol. 12, No. 8, pp. 861-870 (10 pp.), doi: 10.1089/104303401750195836.
Matthew J Moscou and Adam J Bogdanove, "A simple cipher governs DNA recognition by TAL effectors", Science, Dec. 11, 2009, vol. 326, No. 5959, p. 1501, doi: 10.1126/science.1178817.
Michael C Milone et al., "Chimeric receptors containing CD137 signal transduction domains mediate enhanced survival of T cells and increased antileukemic efficacy in vivo", Molecular Therapy, Aug. 2009, vol. 17, No. 8, pp. 1453-1464 (12 pp.), doi: 10.1038/mt.2009.83.

\* cited by examiner

SEQUENCE LISTING

<160> NUMBER OF SEQ ID NOS: 78

<210> SEQ ID NO 1

```
<211> LENGTH: 4
<212> TYPE: PRT
<213> ORGANISM: Artificial Sequence
<220> FEATURE:
<223> OTHER INFORMATION: linker

<400> SEQUENCE: 1

Gly Gly Gly Ser
1

<210> SEQ ID NO 2
<211> LENGTH: 20
<212> TYPE: PRT
<213> ORGANISM: Artificial Sequence
<220> FEATURE:
<223> OTHER INFORMATION: linker

<400> SEQUENCE: 2

Gly Gly Gly Gly Ser Gly Gly Gly Ser Gly Gly Gly Gly Ser Gly
1               5                   10                  15

Gly Gly Gly Ser
            20

<210> SEQ ID NO 3
<211> LENGTH: 15
<212> TYPE: PRT
<213> ORGANISM: Artificial Sequence
<220> FEATURE:
<223> OTHER INFORMATION: linker

<400> SEQUENCE: 3

Gly Gly Gly Gly Ser Gly Gly Gly Gly Ser Gly Gly Gly Gly Ser
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: linker

<400> SEQUENCE: 4

Gly Gly Gly Gly Ser Gly Gly Gly Gly Ser
1               5                   10

<210> SEQ ID NO 5
<211> LENGTH: 5
<212> TYPE: PRT
<213> ORGANISM: Artificial Sequence
<220> FEATURE:
<223> OTHER INFORMATION: linker

<400> SEQUENCE: 5

Gly Gly Gly Gly Ser
1               5

<210> SEQ ID NO 6
<211> LENGTH: 16
<212> TYPE: PRT
<213> ORGANISM: Artificial Sequence
<220> FEATURE:
<223> OTHER INFORMATION: linker

<400> SEQUENCE: 6

Gly Gly Gly Ser Gly Gly Gly Ser Gly Gly Gly Ser Gly Gly Gly Ser
1               5                   10                  15
```

<210> SEQ ID NO 7
<211> LENGTH: 16
<212> TYPE: PRT
<213> ORGANISM: Artificial Sequence
<220> FEATURE:
<223> OTHER INFORMATION: linker

<400> SEQUENCE: 7

Ala Gly Ser Ser Ser Gly Gly Ser Thr Thr Gly Gly Ser Thr Thr
1               5                   10                  15

<210> SEQ ID NO 8
<211> LENGTH: 16
<212> TYPE: PRT
<213> ORGANISM: Artificial Sequence
<220> FEATURE:
<223> OTHER INFORMATION: linker

<400> SEQUENCE: 8

Gly Thr Thr Ala Ala Ser Gly Ser Ser Gly Gly Ser Ser Ser Gly Ala
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: linker

<400> SEQUENCE: 9

Ser Ser Ala Thr Ala Thr Ala Gly Thr Gly Ser Ser Thr Gly Ser Thr
1               5                   10                  15

<210> SEQ ID NO 10
<211> LENGTH: 16
<212> TYPE: PRT
<213> ORGANISM: Artificial Sequence
<220> FEATURE:
<223> OTHER INFORMATION: linker

<400> SEQUENCE: 10

Thr Ser Gly Ser Thr Gly Thr Ala Ala Ser Ser Thr Ser Thr Ser Thr
1               5                   10                  15

<210> SEQ ID NO 11
<211> LENGTH: 30
<212> TYPE: DNA
<213> ORGANISM: Artificial Sequence
<220> FEATURE:
<223> OTHER INFORMATION: linker

<400> SEQUENCE: 11
ggtggcggag gttctggagg tggaggttcc                                        30

<210> SEQ ID NO 12
<211> LENGTH: 7
<212> TYPE: PRT
<213> ORGANISM: Artificial Sequence
<220> FEATURE:
<223> OTHER INFORMATION: hinge KIR2DS2

<400> SEQUENCE: 12

Lys Ile Arg Arg Asp Ser Ser
1               5

<210> SEQ ID NO 13

```
<211> LENGTH: 45
<212> TYPE: PRT
<213> ORGANISM: Artificial Sequence
<220> FEATURE:
<223> OTHER INFORMATION: CD8 hinge

<400> SEQUENCE: 13

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp
        35                  40                  45

<210> SEQ ID NO 14
<211> LENGTH: 135
<212> TYPE: DNA
<213> ORGANISM: Artificial Sequence
<220> FEATURE:
<223> OTHER INFORMATION: CD8 hinge

<400> SEQUENCE: 14
accacgacgc cagcgccgcg accaccaaca ccggcgccca ccatcgcgtc gcagcccctg      60
tccctgcgcc cagaggcgtg ccggccagcg gcggggggcg cagtgcacac gagggggctg     120
gacttcgcct gtgat                                                     135

<210> SEQ ID NO 15
<211> LENGTH: 230
<212> TYPE: PRT
<213> ORGANISM: Artificial Sequence
<220> FEATURE:
<223> OTHER INFORMATION: IgG4 hinge

<400> SEQUENCE: 15

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

Thr Val Asp Lys Ser Arg Trp Gln Glu Gly Asn Val Phe Ser Cys Ser
            195                 200                 205

Val Met His Glu Ala Leu His Asn His Tyr Thr Gln Lys Ser Leu Ser
    210                 215                 220

Leu Ser Leu Gly Lys Met
225             230

<210> SEQ ID NO 16
<211> LENGTH: 690
<212> TYPE: DNA
<213> ORGANISM: Artificial Sequence
<220> FEATURE:
<223> OTHER INFORMATION: IgG4 hinge

<400> SEQUENCE: 16
gagagcaagt acggccctcc ctgcccccct tgccctgccc ccgagttcct gggcggaccc      60
agcgtgttcc tgttcccccc caagcccaag acaccctga tgatcagccg gaccccgag     120 gtgacctgtg tggtggtgga cgtgtcccag gaggaccccg aggtccagtt caactggtac    180
gtggacggcg tggaggtgca caacgccaag accaagcccc gggaggagca gttcaatagc    240
acctaccggg tggtgtccgt gctgaccgtg ctgcaccagg actggctgaa cggcaaggaa    300
tacaagtgta aggtgtccaa caagggcctg cccagcagca tcgagaaaac catcagcaag    360
gccaagggcc agcctcggga gccccaggtg tacaccctgc cccctagcca agaggagatg    420
accaagaacc aggtgtccct gacctgcctg gtgaagggct tctacccag cgacatcgcc     480 gtggagtggg agagcaacgg ccagcccgag aacaactaca agaccacccc ccctgtgctg    540
gacagcgacg gcagcttctt cctgtacagc cggctgaccg tggacaagag ccggtggcag    600
gagggcaacg tctttagctg ctccgtgatg cacgaggccc tgcacaacca ctacacccag    660
aagagcctga gcctgtccct gggcaagatg                                      690

<210> SEQ ID NO 17
<211> LENGTH: 282
<212> TYPE: PRT
<213> ORGANISM: Artificial Sequence
<220> FEATURE:
<223> OTHER INFORMATION: IgD hinge

<400> SEQUENCE: 17

Arg Trp Pro Glu Ser Pro Lys Ala Gln Ala Ser Ser Val Pro Thr Ala
1               5                   10                  15

Gln Pro Gln Ala Glu Gly Ser Leu Ala Lys Ala Thr Thr Ala Pro Ala
            20                  25                  30

Thr Thr Arg Asn Thr Gly Arg Gly Gly Glu Glu Lys Lys Lys Glu Lys
        35                  40                  45

Glu Lys Glu Glu Gln Glu Glu Arg Glu Thr Lys Thr Pro Glu Cys Pro
    50                  55                  60

Ser His Thr Gln Pro Leu Gly Val Tyr Leu Leu Thr Pro Ala Val Gln
65                  70                  75                  80

Asp Leu Trp Leu Arg Asp Lys Ala Thr Phe Thr Cys Phe Val Val Gly
            85                  90                  95

Ser Asp Leu Lys Asp Ala His Leu Thr Trp Glu Val Ala Gly Lys Val
            100                 105                 110

Pro Thr Gly Gly Val Glu Glu Gly Leu Leu Glu Arg His Ser Asn Gly
        115                 120                 125

Ser Gln Ser Gln His Ser Arg Leu Thr Leu Pro Arg Ser Leu Trp Asn
    130                 135                 140

```
Ala Gly Thr Ser Val Thr Cys Thr Leu Asn His Pro Ser Leu Pro Pro
145                 150                 155                 160

Gln Arg Leu Met Ala Leu Arg Glu Pro Ala Gln Ala Pro Val Lys
            165                 170                 175

Leu Ser Leu Asn Leu Leu Ala Ser Ser Asp Pro Pro Glu Ala Ala Ser
            180                 185                 190

Trp Leu Leu Cys Glu Val Ser Gly Phe Ser Pro Pro Asn Ile Leu Leu
            195                 200                 205

Met Trp Leu Glu Asp Gln Arg Glu Val Asn Thr Ser Gly Phe Ala Pro
            210                 215                 220

Ala Arg Pro Pro Gln Pro Gly Ser Thr Thr Phe Trp Ala Trp Ser
225                 230                 235                 240

Val Leu Arg Val Pro Ala Pro Pro Ser Pro Gln Pro Ala Thr Tyr Thr
                245                 250                 255

Cys Val Val Ser His Glu Asp Ser Arg Thr Leu Leu Asn Ala Ser Arg
                260                 265                 270

Ser Leu Glu Val Ser Tyr Val Thr Asp His
            275                 280
```

<210> SEQ ID NO 18
<211> LENGTH: 847
<212> TYPE: DNA
<213> ORGANISM: Artificial Sequence
<220> FEATURE:
<223> OTHER INFORMATION: IgD hinge

<400> SEQUENCE: 18

```
aggtggcccg aaagtcccaa ggcccaggca tctagtgttc ctactgcaca gccccaggca      60
gaaggcagcc tagccaaagc tactactgca cctgccacta cgcgcaatac tggccgtggc     120
ggggaggaga agaaaaagga gaaagagaaa gaagaacagg aagagaggga gaccaagacc     180
cctgaatgtc catcccatac ccagccgctg ggcgtctatc tcttgactcc cgcagtacag     240
gacttgtggc ttagagataa ggccaccttt acatgtttcg tcgtgggctc tgacctgaag     300
gatgcccatt tgacttggga ggttgccgga aaggtaccca ggggggggt tgaggaaggg     360
ttgctggagc gccattccaa tggctctcag agccagcact caagactcac ccttccgaga     420
tccctgtgga acgccgggac tctgtcaca tgtactctaa atcatcctag cctgccccca     480
cagcgtctga tggcccttag agagccagcc gcccaggcac cagttaagct tagcctgaat     540
ctgctcgcca gtagtgatcc cccagaggcc gccagctggc tcttatgcga agtgtccggc     600
tttagcccgc ccaacatctt gctcatgtgg ctggaggacc agcgagaagt gaacaccagc     660
ggcttcgctc cagcccggcc cccacccag ccggggttcta ccacattctg ggcctggagt     720
gtcttaaggg tcccagcacc acctagcccc cagccagcca catacacctg tgttgtgtcc     780
catgaagata gcaggaccct gctaaatgct tctaggagtc tggaggtttc ctacgtgact     840
gaccatt                                                              847
```

<210> SEQ ID NO 19
<211> LENGTH: 39
<212> TYPE: PRT
<213> ORGANISM: Artificial Sequence
<220> FEATURE:
<223> OTHER INFORMATION: CD28 hinge

<400> SEQUENCE: 19

```
Ile Glu Val Met Tyr Pro Pro Pro Tyr Leu Asp Asn Glu Lys Ser Asn
```

Gly Thr Ile Ile His Val Lys Gly Lys His Leu Cys Pro Ser Pro Leu
1               5                   10                  15

Phe Pro Gly Pro Ser Lys Pro
            20                  25                  30

35

<210> SEQ ID NO 20
<211> LENGTH: 117
<212> TYPE: DNA
<213> ORGANISM: Artificial Sequence
<220> FEATURE:
<223> OTHER INFORMATION: CD28 hinge

<400> SEQUENCE: 20
attgaagtta tgtatcctcc tccttaccta gacaatgaga agagcaatgg aaccattatc     60
catgtgaaag ggaaacacct tgtccaagt cccctatttc ccggaccttc taagccc        117

<210> SEQ ID NO 21
<211> LENGTH: 24
<212> TYPE: PRT
<213> ORGANISM: Artificial Sequence
<220> FEATURE:
<223> OTHER INFORMATION: CD8 transmembrane

<400> SEQUENCE: 21

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 22
<211> LENGTH: 72
<212> TYPE: DNA
<213> ORGANISM: Artificial Sequence
<220> FEATURE:
<223> OTHER INFORMATION: CD8 transmembrane

<400> SEQUENCE: 22
atctacatct gggcgccctt ggccgggact tgtggggtcc ttctcctgtc actggttatc     60
accctttact gc                                                         72

<210> SEQ ID NO 23
<211> LENGTH: 27
<212> TYPE: PRT
<213> ORGANISM: Artificial Sequence
<220> FEATURE:
<223> OTHER INFORMATION: CD28 transmembrane

<400> SEQUENCE: 23

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 24
<211> LENGTH: 81
<212> TYPE: DNA
<213> ORGANISM: Artificial Sequence
<220> FEATURE:
<223> OTHER INFORMATION: CD28 transmembrane

<400> SEQUENCE: 24
ttttgggtgc tggtggtggt tggtggagtc ctggcttgct atagcttgct agtaacagtg     60

```
gcctttatta ttttctgggt g                                                  81
```

<210> SEQ ID NO 25
<211> LENGTH: 112
<212> TYPE: PRT
<213> ORGANISM: Artificial Sequence
<220> FEATURE:
<223> OTHER INFORMATION: CD3-zeta

<400> SEQUENCE: 25

```
Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 26
<211> LENGTH: 112
<212> TYPE: PRT
<213> ORGANISM: Artificial Sequence
<220> FEATURE:
<223> OTHER INFORMATION: CD3-zeta

<400> SEQUENCE: 26

```
Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

<210> SEQ ID NO 27
<211> LENGTH: 336
<212> TYPE: DNA
<213> ORGANISM: Artificial Sequence
<220> FEATURE:
<223> OTHER INFORMATION: CD3-zeta

<400> SEQUENCE: 27

```
agagtgaagt tcagcaggag cgcagacgcc cccgcgtaca agcagggcca gaaccagctc      60
tataacgagc tcaatctagg acgaagagag gagtacgatg ttttggacaa gagacgtggc     120
```

```
cgggaccctg agatgggggg aaagccgaga aggaagaacc ctcaggaagg cctgtacaat       180
gaactgcaga aagataagat ggcggaggcc tacagtgaga ttgggatgaa aggcgagcgc       240
cggaggggca aggggcacga tggcctttac cagggtctca gtacagccac caaggacacc       300
tacgacgccc ttcacatgca ggccctgccc cctcgc                                 336
```

```
<210> SEQ ID NO 28
<211> LENGTH: 336
<212> TYPE: DNA
<213> ORGANISM: Artificial Sequence
<220> FEATURE:
<223> OTHER INFORMATION: CD3-zeta

<400> SEQUENCE: 28
agagtgaagt tcagcaggag cgcagacgcc cccgcgtacc agcagggcca gaaccagctc        60
tataacgagc tcaatctagg acgaagagag gagtacgatg tttttggacaa gagacgtggc      120 cgggaccctg agatgggggg aaagccgaga aggaagaacc ctcaggaagg cctgtacaat      180
gaactgcaga aagataagat ggcggaggcc tacagtgaga ttgggatgaa aggcgagcgc      240
cggaggggca aggggcacga tggcctttac cagggtctca gtacagccac caaggacacc      300
tacgacgccc ttcacatgca ggccctgccc cctcgc                                 336
```

```
<210> SEQ ID NO 29
<211> LENGTH: 42
<212> TYPE: PRT
<213> ORGANISM: Artificial Sequence
<220> FEATURE:
<223> OTHER INFORMATION: 4-1BB intracellular aa

<400> SEQUENCE: 29

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40
```

```
<210> SEQ ID NO 30
<211> LENGTH: 48
<212> TYPE: PRT
<213> ORGANISM: Artificial Sequence
<220> FEATURE:
<223> OTHER INFORMATION: CD27 intracellular aa

<400> SEQUENCE: 30

Gln Arg Arg Lys Tyr Arg Ser Asn Lys Gly Glu Ser Pro Val Glu Pro
1               5                   10                  15

Ala Glu Pro Cys Arg Tyr Ser Cys Pro Arg Glu Glu Glu Gly Ser Thr
            20                  25                  30

Ile Pro Ile Gln Glu Asp Tyr Arg Lys Pro Glu Pro Ala Cys Ser Pro
        35                  40                  45
```

```
<210> SEQ ID NO 31
<211> LENGTH: 41
<212> TYPE: PRT
<213> ORGANISM: Artificial Sequence
<220> FEATURE:
<223> OTHER INFORMATION: CD28 intracellular aa

<400> SEQUENCE: 31

Arg Ser Lys Arg Ser Arg Leu Leu His Ser Asp Tyr Met Asn Met Thr
```

```
                1               5                  10                 15
              Pro Arg Arg Pro Gly Pro Thr Arg Lys His Tyr Gln Pro Tyr Ala Pro
                               20                 25                 30

Pro Arg Asp Phe Ala Ala Tyr Arg Ser
                       35                  40

<210> SEQ ID NO 32
<211> LENGTH: 126
<212> TYPE: DNA
<213> ORGANISM: Artificial Sequence
<220> FEATURE:
<223> OTHER INFORMATION: 4-1BB intracellular nt

<400> SEQUENCE: 32
aaacggggca gaaagaaact cctgtatata ttcaaacaac catttatgag accagtacaa    60
actactcaag aggaagatgg ctgtagctgc cgatttccag aagaagaaga aggaggatgt   120
gaactg                                                              126

<210> SEQ ID NO 33
<211> LENGTH: 144
<212> TYPE: DNA
<213> ORGANISM: Artificial Sequence
<220> FEATURE:
<223> OTHER INFORMATION: CD27 intracellular nt

<400> SEQUENCE: 33
caacgaagga atatagatc aaacaaagga gaaagtcctg tggagcctgc agagccttgt     60
cgttacagct gccccaggga ggaggagggc agcaccatcc ccatccagga ggattaccga   120
aaaccggagc ctgcctgctc cccc                                          144

<210> SEQ ID NO 34
<211> LENGTH: 123
<212> TYPE: DNA
<213> ORGANISM: Artificial Sequence
<220> FEATURE:
<223> OTHER INFORMATION: CD28 intracellular

<400> SEQUENCE: 34
aggagtaaga ggagcaggct cctgcacagt gactacatga acatgactcc ccgccgcccc    60
gggcccaccc gcaagcatta ccagccctat gccccaccac gcgacttcgc agcctatcgc   120
tcc                                                                 123

<210> SEQ ID NO 35
<211> LENGTH: 222
<212> TYPE: PRT
<213> ORGANISM: Artificial Sequence
<220> FEATURE:
<223> OTHER INFORMATION: CAR

<400> SEQUENCE: 35

Ala Ala Ala Ile Glu Val Met Tyr Pro Pro Pro Tyr Leu Asp Asn Glu
1               5                   10                  15

Lys Ser Asn Gly Thr Ile Ile His Val Lys Gly Lys His Leu Cys Pro
            20                  25                  30

Ser Pro Leu Phe Pro Gly Pro Ser Lys Pro Phe Trp Val Leu Val Val
        35                  40                  45

Val Gly Gly Val Leu Ala Cys Tyr Ser Leu Leu Val Thr Val Ala Phe
    50                  55                  60

Ile Ile Phe Trp Val Arg Ser Lys Arg Ser Arg Leu Leu His Ser Asp
```

```
                65                  70                  75                  80
Tyr Met Asn Met Thr Pro Arg Pro Gly Pro Thr Arg Lys His Tyr
                    85                  90                  95

Gln Pro Tyr Ala Pro Pro Arg Asp Phe Ala Ala Tyr Arg Ser Arg Val
                    100                 105                 110

Lys Phe Ser Arg Ser Ala Asp Ala Pro Ala Tyr Gln Gln Gly Gln Asn
                    115                 120                 125

Gln Leu Tyr Asn Glu Leu Asn Leu Gly Arg Arg Glu Glu Tyr Asp Val
            130                 135                 140

Leu Asp Lys Arg Arg Gly Arg Asp Pro Glu Met Gly Gly Lys Pro Arg
145                 150                 155                 160

Arg Lys Asn Pro Gln Glu Gly Leu Tyr Asn Glu Leu Gln Lys Asp Lys
                    165                 170                 175

Met Ala Glu Ala Tyr Ser Glu Ile Gly Met Lys Gly Glu Arg Arg Arg
                    180                 185                 190

Gly Lys Gly His Asp Gly Leu Tyr Gln Gly Leu Ser Thr Ala Thr Lys
            195                 200                 205

Asp Thr Tyr Asp Ala Leu His Met Gln Ala Leu Pro Pro Arg
        210                 215                 220

<210> SEQ ID NO 36
<211> LENGTH: 249
<212> TYPE: PRT
<213> ORGANISM: Artificial Sequence
<220> FEATURE:
<223> OTHER INFORMATION: scFv anti IL-23R

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
                20                  25                  30

Leu Ala Trp Tyr Gln Gln Lys Pro Gly Lys Ala Pro Lys Leu Leu Ile
            35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gly Gly Thr Lys Leu Thr Val Leu
                100                 105                 110

Gly Gly Gly Gly Ser Gly Gly Gly Ser Gly Gly Gly Gly Ser
            115                 120                 125

Glu Val Gln Leu Val Glu Ser Gly Gly Gly Leu Val Gln Pro Gly Gly
        130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
                180                 185                 190

Trp Ala Lys Gly Arg Phe Thr Ile Ser Arg Asp Asn Ser Lys Asn Thr
            195                 200                 205

Val Tyr Leu Gln Met Asn Ser Leu Arg Ala Glu Asp Thr Ala Val Tyr
```

```
                210                 215                 220
Tyr Cys Ala Thr Ser Gly Ser Ser Val Leu Tyr Phe Lys Phe Trp Gly
225                 230                 235                 240

Gln Gly Thr Leu Val Thr Val Ser Ser
                245

<210> SEQ ID NO 37
<211> LENGTH: 121
<212> TYPE: PRT
<213> ORGANISM: Artificial Sequence
<220> FEATURE:
<223> OTHER INFORMATION: VH anti-IL23R

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Asn Ser Asn
            20                  25                  30

Tyr Tyr Met Cys Trp Val Arg Gln Ala Pro Gly Lys Gly Leu Glu Trp
        35                  40                  45

Ile Gly Cys Ile Tyr Val Gly Ser His Val Asn Thr Tyr Tyr Ala Asn
50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120

<210> SEQ ID NO 38
<211> LENGTH: 113
<212> TYPE: PRT
<213> ORGANISM: Artificial Sequence
<220> FEATURE:
<223> OTHER INFORMATION: VL anti-IL23R

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly

<210> SEQ ID NO 39
<211> LENGTH: 21
<212> TYPE: PRT
```

```
<213> ORGANISM: Artificial Sequence
<220> FEATURE:
<223> OTHER INFORMATION: CD8 leader

<400> SEQUENCE: 39

Met Ala Leu Pro Val Thr Ala Leu Leu Pro Leu Ala Leu Leu Leu
1               5                   10                  15

His Ala Ala Arg Pro
            20

<210> SEQ ID NO 40
<211> LENGTH: 493
<212> TYPE: PRT
<213> ORGANISM: Artificial Sequence
<220> FEATURE:
<223> OTHER INFORMATION: CAR

<400> SEQUENCE: 40

Met Ala Leu Pro Val Thr Ala Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Gln Ala Ser Glu
        35                  40                  45

Asn Ile Tyr Ser Phe Leu Ala Trp Tyr Gln Gln Lys Pro Gly Lys Ala
    50                  55                  60

Pro Lys Leu Leu Ile Tyr Ser Ala Ser Lys Leu Ala Ala Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Thr
            100                 105                 110

Asn Arg Tyr Ser Asn Pro Asp Ile Tyr Asn Val Phe Gly Gln Gly Thr
        115                 120                 125

Lys Leu Thr Val Leu Gly Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Ile
                165                 170                 175

Asp Phe Asn Ser Asn Tyr Tyr Met Cys Trp Val Arg Gln Ala Pro Gly
            180                 185                 190

Lys Gly Leu Glu Trp Ile Gly Cys Ile Tyr Val Gly Ser His Val Asn
        195                 200                 205

Thr Tyr Tyr Ala Asn Trp Ala Lys Gly Arg Phe Thr Ile Ser Arg Asp
    210                 215                 220

Asn Ser Lys Asn Thr Val Tyr Leu Gln Met Asn Ser Leu Arg Ala Glu
225                 230                 235                 240

Asp Thr Ala Val Tyr Tyr Cys Ala Thr Ser Gly Ser Ser Val Leu Tyr
                245                 250                 255

Phe Lys Phe Trp Gly Gln Gly Thr Leu Val Thr Val Ser Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300
```

```
Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
            325                 330                 335

Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
            355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Arg Arg
            420                 425                 430

Lys Asn Pro Gln Glu Gly Leu Tyr Asn Glu Leu Gln Lys Asp Lys Met
                435                 440                 445

Ala Glu Ala Tyr Ser Glu Ile Gly Met Lys Gly Glu Arg Arg Arg Gly
    450                 455                 460

Lys Gly His Asp Gly Leu Tyr Gln Gly Leu Ser Thr Ala Thr Lys Asp
465                 470                 475                 480

Thr Tyr Asp Ala Leu His Met Gln Ala Leu Pro Pro Arg
                485                 490

<210> SEQ ID NO 41
<211> LENGTH: 472
<212> TYPE: PRT
<213> ORGANISM: Artificial Sequence
<220> FEATURE:
<223> OTHER INFORMATION: CAR

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175
```

```
Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser Thr Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

Glu Glu Glu Gly Gly Cys Glu Leu Arg Val Lys Phe Ser Arg Ser Ala
        355                 360                 365

Asp Ala Pro Ala Tyr Gln Gln Gly Gln Asn Gln Leu Tyr Asn Glu Leu
    370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Arg Arg Lys Asn Pro Gln Glu
                405                 410                 415

Gly Leu Tyr Asn Glu Leu Gln Lys Asp Lys Met Ala Glu Ala Tyr Ser
            420                 425                 430

Glu Ile Gly Met Lys Gly Glu Arg Arg Arg Gly Lys Gly His Asp Gly
        435                 440                 445

Leu Tyr Gln Gly Leu Ser Thr Ala Thr Lys Asp Thr Tyr Asp Ala Leu
    450                 455                 460

His Met Gln Ala Leu Pro Pro Arg
465                 470

<210> SEQ ID NO 42
<211> LENGTH: 506
<212> TYPE: PRT
<213> ORGANISM: Artificial Sequence
<220> FEATURE:
<223> OTHER INFORMATION: CAR

<400> SEQUENCE: 42

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Gln Ala Ser Glu
        35                  40                  45

Asn Ile Tyr Ser Phe Leu Ala Trp Tyr Gln Gln Lys Pro Gly Lys Ala
    50                  55                  60
```

```
Pro Lys Leu Leu Ile Tyr Ser Ala Ser Lys Leu Ala Gly Val Pro
 65                  70                  75                  80

Ser Arg Phe Ser Gly Ser Gly Ser Gly Thr Asp Phe Thr Leu Thr Ile
                 85                  90                  95

Ser Ser Leu Gln Pro Glu Asp Phe Ala Thr Tyr Tyr Cys Gln Gln Thr
            100                 105                 110

Asn Arg Tyr Ser Asn Pro Asp Ile Tyr Asn Val Phe Gly Gln Gly Thr
            115                 120                 125

Lys Leu Thr Val Leu Gly Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Ile
                165                 170                 175

Asp Phe Asn Ser Asn Tyr Tyr Met Cys Trp Val Arg Gln Ala Pro Gly
                180                 185                 190

Lys Gly Leu Glu Trp Ile Gly Cys Ile Tyr Val Gly Ser His Val Asn
            195                 200                 205

Thr Tyr Tyr Ala Asn Trp Ala Lys Gly Arg Phe Thr Ile Ser Arg Asp
    210                 215                 220

Asn Ser Lys Asn Thr Val Tyr Leu Gln Met Asn Ser Leu Arg Ala Glu
225                 230                 235                 240

Asp Thr Ala Val Tyr Tyr Cys Ala Thr Ser Gly Ser Ser Val Leu Tyr
                245                 250                 255

Phe Lys Phe Trp Gly Gln Gly Thr Leu Val Thr Val Ser Ser Asn Trp
                260                 265                 270

Ser His Pro Gln Phe Glu Lys Met His Thr Thr Thr Pro Ala Pro Arg
    275                 280                 285

Pro Pro Thr Pro Ala Pro Thr Ile Ala Ser Gln Pro Leu Ser Leu Arg
290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Lys Arg
                340                 345                 350

Gly Arg Lys Lys Leu Leu Tyr Ile Phe Lys Gln Pro Phe Met Arg Pro
            355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Thr Arg Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Arg Arg Lys Asn Pro
            435                 440                 445

Gln Glu Gly Leu Tyr Asn Glu Leu Gln Lys Asp Lys Met Ala Glu Ala
    450                 455                 460

Tyr Ser Glu Ile Gly Met Lys Gly Glu Arg Arg Arg Gly Lys Gly His
465                 470                 475                 480

Asp Gly Leu Tyr Gln Gly Leu Ser Thr Ala Thr Lys Asp Thr Tyr Asp
```

```
                        485                 490                 495
Ala Leu His Met Gln Ala Leu Pro Pro Arg
            500                 505
```

<210> SEQ ID NO 43
<211> LENGTH: 485
<212> TYPE: PRT
<213> ORGANISM: Artificial Sequence
<220> FEATURE:
<223> OTHER INFORMATION: CAR

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly Gly Gly Gly Ser Gly Gly Gly Ser Gly Gly Gly Ser
        115                 120                 125

Glu Val Gln Leu Val Glu Ser Gly Gly Gly Leu Val Gln Pro Gly Gly
        130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser Asn Trp Ser His Pro Gln Phe
                245                 250                 255

Glu Lys Met His Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
```

```
                340                 345                 350
Glu Glu Asp Gly Cys Ser Cys Arg Phe Pro Glu Glu Glu Gly Gly
            355                 360                 365
Cys Glu Leu Thr Arg Arg Val Lys Phe Ser Arg Ser Ala Asp Ala Pro
        370                 375                 380
Ala Tyr Gln Gln Gly Gln Asn Gln Leu Tyr Asn Glu Leu Asn Leu Gly
385                 390                 395                 400
Arg Arg Glu Glu Tyr Asp Val Leu Asp Lys Arg Arg Gly Arg Asp Pro
                405                 410                 415
Glu Met Gly Gly Lys Pro Arg Arg Lys Asn Pro Gln Glu Gly Leu Tyr
            420                 425                 430
Asn Glu Leu Gln Lys Asp Lys Met Ala Glu Ala Tyr Ser Glu Ile Gly
        435                 440                 445
Met Lys Gly Glu Arg Arg Arg Gly Lys Gly His Asp Gly Leu Tyr Gln
        450                 455                 460
Gly Leu Ser Thr Ala Thr Lys Asp Thr Tyr Asp Ala Leu His Met Gln
465                 470                 475                 480
Ala Leu Pro Pro Arg
            485

<210> SEQ ID NO 44
<211> LENGTH: 22
<212> TYPE: PRT
<213> ORGANISM: Artificial Sequence
<220> FEATURE:
<223> OTHER INFORMATION: P2A

<400> SEQUENCE: 44

Gly Ser Gly Ala Thr Asn Phe Ser Leu Leu Lys Gln Ala Gly Asp Val
1               5                   10                  15
Glu Glu Asn Pro Gly Pro
            20

<210> SEQ ID NO 45
<211> LENGTH: 239
<212> TYPE: PRT
<213> ORGANISM: Artificial Sequence
<220> FEATURE:
<223> OTHER INFORMATION: GFP

<400> SEQUENCE: 45

Met Val Ser Lys Gly Glu Glu Leu Phe Thr Gly Val Val Pro Ile Leu
1               5                   10                  15
Val Glu Leu Asp Gly Asp Val Asn Gly His Lys Phe Ser Val Ser Gly
            20                  25                  30
Glu Gly Glu Gly Asp Ala Thr Tyr Gly Lys Leu Thr Leu Lys Phe Ile
        35                  40                  45
Cys Thr Thr Gly Lys Leu Pro Val Pro Trp Pro Thr Leu Val Thr Thr
    50                  55                  60
Leu Thr Tyr Gly Val Gln Cys Phe Ser Arg Tyr Pro Asp His Met Lys
65                  70                  75                  80
Gln His Asp Phe Phe Lys Ser Ala Met Pro Glu Gly Tyr Val Gln Glu
                85                  90                  95
Arg Thr Ile Phe Phe Lys Asp Asp Gly Asn Tyr Lys Thr Arg Ala Glu
            100                 105                 110
Val Lys Phe Glu Gly Asp Thr Leu Val Asn Arg Ile Glu Leu Lys Gly
        115                 120                 125
```

```
Ile Asp Phe Lys Glu Asp Gly Asn Ile Leu Gly His Lys Leu Glu Tyr
            130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
                195                 200                 205

Ser Lys Asp Pro Asn Glu Lys Arg Asp His Met Val Leu Leu Glu Phe
210                 215                 220

Val Thr Ala Ala Gly Ile Thr Leu Gly Met Asp Glu Leu Tyr Lys
225                 230                 235
```

<210> SEQ ID NO 46
<211> LENGTH: 113
<212> TYPE: PRT
<213> ORGANISM: Artificial Sequence
<220> FEATURE:
<223> OTHER INFORMATION: VL anti-IL-23R

<400> SEQUENCE: 46

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gly Gly Thr Lys Leu Thr Val Leu
            100                 105                 110

Gly
```

<210> SEQ ID NO 47
<211> LENGTH: 496
<212> TYPE: PRT
<213> ORGANISM: Artificial Sequence
<220> FEATURE:
<223> OTHER INFORMATION: CAR

<400> SEQUENCE: 47

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Gln Ala Ser Glu
        35                  40                  45

Asn Ile Tyr Ser Phe Leu Ala Trp Tyr Gln Gln Lys Pro Gly Lys Ala
    50                  55                  60

Pro Lys Leu Leu Ile Tyr Ser Ala Ser Lys Leu Ala Ala Gly Val Pro
65                  70                  75                  80
```

```
Ser Arg Phe Ser Gly Ser Gly Ser Gly Thr Asp Phe Thr Leu Thr Ile
                85              90                  95

Ser Ser Leu Gln Pro Glu Asp Phe Ala Thr Tyr Tyr Cys Gln Gln Thr
            100                 105                 110

Asn Arg Tyr Ser Asn Pro Asp Ile Tyr Asn Val Phe Gly Gln Gly Thr
        115                 120                 125

Lys Leu Thr Val Leu Gly Gly Gly Gly Ser Gly Gly Gly Gly Ser
130                 135                 140

Gly Gly Gly Ser Glu Val Gln Leu Val Glu Ser Gly Gly Gly Leu
145             150                 155                 160

Val Gln Pro Gly Gly Ser Leu Arg Leu Ser Cys Ala Ala Ser Gly Ile
            165                 170                 175

Asp Phe Asn Ser Asn Tyr Tyr Met Cys Trp Val Arg Gln Ala Pro Gly
            180                 185                 190

Lys Gly Leu Glu Trp Ile Gly Cys Ile Tyr Val Gly Ser His Val Asn
        195                 200                 205

Thr Tyr Tyr Ala Asn Trp Ala Lys Gly Arg Phe Thr Ile Ser Arg Asp
    210                 215                 220

Asn Ser Lys Asn Thr Val Tyr Leu Gln Met Asn Ser Leu Arg Ala Glu
225                 230                 235                 240

Asp Thr Ala Val Tyr Tyr Cys Ala Thr Ser Gly Ser Ser Val Leu Tyr
                245                 250                 255

Phe Lys Phe Trp Gly Gln Gly Thr Leu Val Thr Val Ser Ser Met His
            260                 265                 270

Thr Thr Thr Pro Ala Pro Arg Pro Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Arg Ser Lys Arg Ser Arg Leu Leu His Ser Asp
            340                 345                 350

Tyr Met Asn Met Thr Pro Arg Arg Pro Gly Pro Thr Arg Lys His Tyr
            355                 360                 365

Gln Pro Tyr Ala Pro Pro Arg Asp Phe Ala Ala Tyr Arg Ser Thr Arg
    370                 375                 380

Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
                405                 410                 415

Asp Val Leu Asp Lys Arg Arg Gly Arg Asp Pro Glu Met Gly Gly Lys
            420                 425                 430

Pro Arg Arg Lys Asn Pro Gln Glu Gly Leu Tyr Asn Glu Leu Gln Lys
        435                 440                 445

Asp Lys Met Ala Glu Ala Tyr Ser Glu Ile Gly Met Lys Gly Glu Arg
    450                 455                 460

Arg Arg Gly Lys Gly His Asp Gly Leu Tyr Gln Gly Leu Ser Thr Ala
465                 470                 475                 480

Thr Lys Asp Thr Tyr Asp Ala Leu His Met Gln Ala Leu Pro Pro Arg
                485                 490                 495
```

<210> SEQ ID NO 48
<211> LENGTH: 475
<212> TYPE: PRT
<213> ORGANISM: Artificial Sequence
<220> FEATURE:
<223> OTHER INFORMATION: CAR

<400> SEQUENCE: 48

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly Gly Gly Gly Gly Ser Gly Gly Gly Ser Gly Gly Gly Gly Ser
        115                 120                 125

Glu Val Gln Leu Val Glu Ser Gly Gly Leu Val Gln Pro Gly Gly
            130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser Met His Thr Thr Thr Pro Ala
                245                 250                 255

Pro Arg Pro Pro Thr Pro Ala Pro Thr Ile Ala Ser Gln Pro Leu Ser
            260                 265                 270

Leu Arg Pro Glu Ala Cys Arg Pro Ala Ala Gly Gly Ala Val His Thr
        275                 280                 285

Arg Gly Leu Asp Phe Ala Cys Asp Ile Tyr Ile Trp Ala Pro Leu Ala
290                 295                 300

Gly Thr Cys Gly Val Leu Leu Leu Ser Leu Val Ile Thr Leu Tyr Cys
305                 310                 315                 320

Arg Ser Lys Arg Ser Arg Leu Leu His Ser Asp Tyr Met Asn Met Thr
                325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Thr Arg Val Lys Phe Ser
        355                 360                 365

Arg Ser Ala Asp Ala Pro Ala Tyr Gln Gln Gly Gln Asn Gln Leu Tyr
```

```
                370             375             380
Asn Glu Leu Asn Leu Gly Arg Arg Glu Tyr Asp Val Leu Asp Lys
385                 390                 395                 400

Arg Arg Gly Arg Asp Pro Glu Met Gly Gly Lys Pro Arg Arg Lys Asn
                405                 410                 415

Pro Gln Glu Gly Leu Tyr Asn Glu Leu Gln Lys Asp Lys Met Ala Glu
            420                 425                 430

Ala Tyr Ser Glu Ile Gly Met Lys Gly Glu Arg Arg Arg Gly Lys Gly
        435                 440                 445

His Asp Gly Leu Tyr Gln Gly Leu Ser Thr Ala Thr Lys Asp Thr Tyr
    450                 455                 460

Asp Ala Leu His Met Gln Ala Leu Pro Pro Arg
465                 470                 475

<210> SEQ ID NO 49
<211> LENGTH: 223
<212> TYPE: PRT
<213> ORGANISM: Artificial Sequence
<220> FEATURE:
<223> OTHER INFORMATION: CAR

<400> SEQUENCE: 49

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Gln Gln Gly Gln
        115                 120                 125

Asn Gln Leu Tyr Asn Glu Leu Asn Leu Gly Arg Arg Glu Glu Tyr Asp
    130                 135                 140

Val Leu Asp Lys Arg Arg Gly Arg Asp Pro Glu Met Gly Gly Lys Pro
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
            180                 185                 190

Arg Gly Lys Gly His Asp Gly Leu Tyr Gln Gly Leu Ser Thr Ala Thr
        195                 200                 205

Lys Asp Thr Tyr Asp Ala Leu His Met Gln Ala Leu Pro Pro Arg
    210                 215                 220

<210> SEQ ID NO 50
<211> LENGTH: 236
<212> TYPE: PRT
<213> ORGANISM: Artificial Sequence
<220> FEATURE:
<223> OTHER INFORMATION: CAR
```

<400> SEQUENCE: 50

Asn Trp Ser His Pro Gln Phe Glu Lys Met His Thr Thr Thr Pro Ala
1               5                   10                  15

Pro Arg Pro Pro Thr Pro Ala Pro Thr Ile Ala Ser Gln Pro Leu Ser
            20                  25                  30

Leu Arg Pro Glu Ala Cys Arg Pro Ala Ala Gly Gly Ala Val His Thr
        35                  40                  45

Arg Gly Leu Asp Phe Ala Cys Asp Ile Tyr Ile Trp Ala Pro Leu Ala
    50                  55                  60

Gly Thr Cys Gly Val Leu Leu Leu Ser Leu Val Ile Thr Leu Tyr Cys
65                  70                  75                  80

Lys Arg Gly Arg Lys Lys Leu Leu Tyr Ile Phe Lys Gln Pro Phe Met
                85                  90                  95

Arg Pro Val Gln Thr Thr Gln Glu Glu Asp Gly Cys Ser Cys Arg Phe
            100                 105                 110

Pro Glu Glu Glu Glu Gly Gly Cys Glu Leu Thr Arg Arg Val Lys Phe
        115                 120                 125

Ser Arg Ser Ala Asp Ala Pro Ala Tyr Gln Gln Gly Gln Asn Gln Leu
    130                 135                 140

Tyr Asn Glu Leu Asn Leu Gly Arg Arg Glu Glu Tyr Asp Val Leu Asp
145                 150                 155                 160

Lys Arg Arg Gly Arg Asp Pro Glu Met Gly Gly Lys Pro Arg Arg Lys
                165                 170                 175

Asn Pro Gln Glu Gly Leu Tyr Asn Glu Leu Gln Lys Asp Lys Met Ala
            180                 185                 190

Glu Ala Tyr Ser Glu Ile Gly Met Lys Gly Glu Arg Arg Arg Gly Lys
        195                 200                 205

Gly His Asp Gly Leu Tyr Gln Gly Leu Ser Thr Ala Thr Lys Asp Thr
    210                 215                 220

Tyr Asp Ala Leu His Met Gln Ala Leu Pro Pro Arg
225                 230                 235

<210> SEQ ID NO 51
<211> LENGTH: 226
<212> TYPE: PRT
<213> ORGANISM: Artificial Sequence
<220> FEATURE:
<223> OTHER INFORMATION: CAR

<400> SEQUENCE: 51

Met His Thr Thr Thr Pro Ala Pro Arg Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Val Ile Thr Leu Tyr Cys Arg Ser Lys Arg Ser Arg Leu Leu His
65                  70                  75                  80

Ser Asp Tyr Met Asn Met Thr Pro Arg Pro Gly Pro Thr Arg Lys
                85                  90                  95

His Tyr Gln Pro Tyr Ala Pro Pro Arg Asp Phe Ala Ala Tyr Arg Ser
            100                 105                 110

```
Thr Arg Arg Val Lys Phe Ser Arg Ser Ala Asp Ala Pro Ala Tyr Gln
        115                 120                 125

Gln Gly Gln Asn Gln Leu Tyr Asn Glu Leu Asn Leu Gly Arg Arg Glu
130                 135                 140

Glu Tyr Asp Val Leu Asp Lys Arg Gly Arg Asp Pro Glu Met Gly
145                 150                 155                 160

Gly Lys Pro Arg Arg Lys Asn Pro Gln Glu Gly Leu Tyr Asn Glu Leu
                165                 170                 175

Gln Lys Asp Lys Met Ala Glu Ala Tyr Ser Glu Ile Gly Met Lys Gly
            180                 185                 190

Glu Arg Arg Arg Gly Lys Gly His Asp Gly Leu Tyr Gln Gly Leu Ser
        195                 200                 205

Thr Ala Thr Lys Asp Thr Tyr Asp Ala Leu His Met Gln Ala Leu Pro
    210                 215                 220

Pro Arg
225

<210> SEQ ID NO 52
<211> LENGTH: 505
<212> TYPE: PRT
<213> ORGANISM: Artificial Sequence
<220> FEATURE:
<223> OTHER INFORMATION: CAR

<400> SEQUENCE: 52

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Gln Ala Ser Glu
            35                  40                  45

Asn Ile Tyr Ser Phe Leu Ala Trp Tyr Gln Gln Lys Pro Gly Lys Ala
        50                  55                  60

Pro Lys Leu Leu Ile Tyr Ser Ala Ser Lys Leu Ala Ala Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Thr
            100                 105                 110

Asn Arg Tyr Ser Asn Pro Asp Ile Tyr Asn Val Phe Gly Gln Gly Thr
        115                 120                 125

Lys Leu Thr Val Leu Gly Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Ile
                165                 170                 175

Asp Phe Asn Ser Asn Tyr Tyr Met Cys Trp Val Arg Gln Ala Pro Gly
            180                 185                 190

Lys Gly Leu Glu Trp Ile Gly Cys Ile Tyr Val Gly Ser His Val Asn
        195                 200                 205

Thr Tyr Tyr Ala Asn Trp Ala Lys Gly Arg Phe Thr Ile Ser Arg Asp
    210                 215                 220

Asn Ser Lys Asn Thr Val Tyr Leu Gln Met Asn Ser Leu Arg Ala Glu
225                 230                 235                 240
```

```
Asp Thr Ala Val Tyr Tyr Cys Ala Thr Ser Gly Ser Ser Val Leu Tyr
                245                 250                 255

Phe Lys Phe Trp Gly Gln Gly Thr Leu Val Thr Val Ser Ser Asn Trp
            260                 265                 270

Ser His Pro Gln Phe Glu Lys Met His Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Arg Ser
            340                 345                 350

Lys Arg Ser Arg Leu Leu His Ser Asp Tyr Met Asn Met Thr Pro Arg
        355                 360                 365

Arg Pro Gly Pro Thr Arg Lys His Tyr Gln Pro Tyr Ala Pro Pro Arg
    370                 375                 380

Asp Phe Ala Ala Tyr Arg Ser Thr Arg Arg Val Lys Phe Ser Arg Ser
385                 390                 395                 400

Ala Asp Ala Pro Ala Tyr Gln Gln Gly Gln Asn Gln Leu Tyr Asn Glu
                405                 410                 415

Leu Asn Leu Gly Arg Arg Glu Glu Tyr Asp Val Leu Asp Lys Arg Arg
            420                 425                 430

Gly Arg Asp Pro Glu Met Gly Gly Lys Pro Arg Arg Lys Asn Pro Gln
        435                 440                 445

Glu Gly Leu Tyr Asn Glu Leu Gln Lys Asp Lys Met Ala Glu Ala Tyr
    450                 455                 460

Ser Glu Ile Gly Met Lys Gly Glu Arg Arg Arg Gly Lys Gly His Asp
465                 470                 475                 480

Gly Leu Tyr Gln Gly Leu Ser Thr Ala Thr Lys Asp Thr Tyr Asp Ala
                485                 490                 495

Leu His Met Gln Ala Leu Pro Pro Arg
            500                 505

<210> SEQ ID NO 53
<211> LENGTH: 484
<212> TYPE: PRT
<213> ORGANISM: Artificial Sequence
<220> FEATURE:
<223> OTHER INFORMATION: CAR

<400> SEQUENCE: 53

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95
```

Pro Asp Ile Tyr Asn Val Phe Gly Gln Gly Thr Lys Leu Thr Val Leu
            100                 105                 110

Gly Gly Gly Gly Ser Gly Gly Gly Gly Ser Gly Gly Gly Ser
    115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser Asn Trp Ser His Pro Gln Phe
                245                 250                 255

Glu Lys Met His Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Thr Arg Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
385                 390                 395                 400

Arg Glu Glu Tyr Asp Val Leu Asp Lys Arg Arg Gly Arg Asp Pro Glu
                405                 410                 415

Met Gly Gly Lys Pro Arg Arg Lys Asn Pro Gln Glu Gly Leu Tyr Asn
            420                 425                 430

Glu Leu Gln Lys Asp Lys Met Ala Glu Ala Tyr Ser Glu Ile Gly Met
        435                 440                 445

Lys Gly Glu Arg Arg Arg Gly Lys Gly His Asp Gly Leu Tyr Gln Gly
    450                 455                 460

Leu Ser Thr Ala Thr Lys Asp Thr Tyr Asp Ala Leu His Met Gln Ala
465                 470                 475                 480

Leu Pro Pro Arg

<210> SEQ ID NO 54
<211> LENGTH: 754
<212> TYPE: PRT
<213> ORGANISM: Artificial Sequence

<220> FEATURE:
<223> OTHER INFORMATION: CAR

<400> SEQUENCE: 54

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Gln Ala Ser Glu
        35                  40                  45

Asn Ile Tyr Ser Phe Leu Ala Trp Tyr Gln Gln Lys Pro Gly Lys Ala
    50                  55                  60

Pro Lys Leu Leu Ile Tyr Ser Ala Ser Lys Leu Ala Ala Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Thr
            100                 105                 110

Asn Arg Tyr Ser Asn Pro Asp Ile Tyr Asn Val Phe Gly Gln Gly Thr
        115                 120                 125

Lys Leu Thr Val Leu Gly Gly Gly Gly Ser Gly Gly Gly Gly Ser
    130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Ile
                165                 170                 175

Asp Phe Asn Ser Asn Tyr Tyr Met Cys Trp Val Arg Gln Ala Pro Gly
            180                 185                 190

Lys Gly Leu Glu Trp Ile Gly Cys Ile Tyr Val Gly Ser His Val Asn
        195                 200                 205

Thr Tyr Tyr Ala Asn Trp Ala Lys Gly Arg Phe Thr Ile Ser Arg Asp
    210                 215                 220

Asn Ser Lys Asn Thr Val Tyr Leu Gln Met Asn Ser Leu Arg Ala Glu
225                 230                 235                 240

Asp Thr Ala Val Tyr Tyr Cys Ala Thr Ser Gly Ser Ser Val Leu Tyr
                245                 250                 255

Phe Lys Phe Trp Gly Gln Gly Thr Leu Val Thr Val Ser Ser Thr Thr
            260                 265                 270

Thr Pro Ala Pro Arg Pro Pro Thr Pro Ala Pro Thr Ile Ala Ser Gln
        275                 280                 285

Pro Leu Ser Leu Arg Pro Glu Ala Cys Arg Pro Ala Ala Gly Gly Ala
    290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
            340                 345                 350

Pro Phe Met Arg Pro Val Gln Thr Thr Gln Glu Glu Asp Gly Cys Ser
        355                 360                 365

Cys Arg Phe Pro Glu Glu Glu Glu Gly Gly Cys Glu Leu Arg Val Lys
    370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Tyr Asp Val Leu
            405                 410                 415

Asp Lys Arg Arg Gly Arg Asp Pro Glu Met Gly Lys Pro Arg Arg
            420                 425                 430

Lys Asn Pro Gln Glu Gly Leu Tyr Asn Glu Leu Gln Lys Asp Lys Met
            435                 440                 445

Ala Glu Ala Tyr Ser Glu Ile Gly Met Lys Gly Glu Arg Arg Arg Gly
450                         455                 460

Lys Gly His Asp Gly Leu Tyr Gln Gly Leu Ser Thr Ala Thr Lys Asp
465                 470                     475                 480

Thr Tyr Asp Ala Leu His Met Gln Ala Leu Pro Pro Arg Gly Ser Gly
                485                 490                 495

Ala Thr Asn Phe Ser Leu Leu Lys Gln Ala Gly Asp Val Glu Glu Asn
                500                 505                 510

Pro Gly Pro Met Val Ser Lys Gly Glu Glu Leu Phe Thr Gly Val Val
            515                 520                 525

Pro Ile Leu Val Glu Leu Asp Gly Asp Val Asn Gly His Lys Phe Ser
            530                 535                 540

Val Ser Gly Glu Gly Glu Gly Asp Ala Thr Tyr Gly Lys Leu Thr Leu
545                 550                     555                 560

Lys Phe Ile Cys Thr Thr Gly Lys Leu Pro Val Pro Trp Pro Thr Leu
                565                 570                 575

Val Thr Thr Leu Thr Tyr Gly Val Gln Cys Phe Ser Arg Tyr Pro Asp
                580                 585                 590

His Met Lys Gln His Asp Phe Phe Lys Ser Ala Met Pro Glu Gly Tyr
            595                 600                 605

Val Gln Glu Arg Thr Ile Phe Phe Lys Asp Asp Gly Asn Tyr Lys Thr
            610                 615                 620

Arg Ala Glu Val Lys Phe Glu Gly Asp Thr Leu Val Asn Arg Ile Glu
625                 630                     635                 640

Leu Lys Gly Ile Asp Phe Lys Glu Asp Gly Asn Ile Leu Gly His Lys
                645                 650                 655

Leu Glu Tyr Asn Tyr Asn Ser His Asn Val Tyr Ile Met Ala Asp Lys
            660                 665                 670

Gln Lys Asn Gly Ile Lys Val Asn Phe Lys Ile Arg His Asn Ile Glu
            675                 680                 685

Asp Gly Ser Val Gln Leu Ala Asp His Tyr Gln Gln Asn Thr Pro Ile
            690                 695                 700

Gly Asp Gly Pro Val Leu Leu Pro Asp Asn His Tyr Leu Ser Thr Gln
705                 710                 715                     720

Ser Ala Leu Ser Lys Asp Pro Asn Glu Lys Arg Asp His Met Val Leu
                725                 730                 735

Leu Glu Phe Val Thr Ala Ala Gly Ile Thr Leu Gly Met Asp Glu Leu
            740                 745                 750

Tyr Lys

<210> SEQ ID NO 55
<211> LENGTH: 249
<212> TYPE: PRT
<213> ORGANISM: Artificial Sequence
<220> FEATURE:
<223> OTHER INFORMATION: scFv anti-IL-23R

<400> SEQUENCE: 55

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly Gly Gly Gly Ser Gly Gly Gly Ser Gly Gly Gly Gly Ser
        115                 120                 125

Glu Val Gln Leu Val Glu Ser Gly Gly Leu Val Gln Pro Gly Gly
            130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser
                245

<210> SEQ ID NO 56
<211> LENGTH: 113
<212> TYPE: PRT
<213> ORGANISM: Artificial Sequence
<220> FEATURE:
<223> OTHER INFORMATION: VL

<400> SEQUENCE: 56

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110
```

Gly

<210> SEQ ID NO 57
<211> LENGTH: 249
<212> TYPE: PRT
<213> ORGANISM: Artificial Sequence
<220> FEATURE:
<223> OTHER INFORMATION: scFv anti IL-23R

<400> SEQUENCE: 57

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly Gly Gly Gly Ser Gly Gly Gly Ser Gly Gly Gly Ser
        115                 120                 125

Glu Val Gln Leu Val Glu Ser Gly Gly Gly Leu Val Gln Pro Gly Gly
130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser
                245
```

<210> SEQ ID NO 58
<211> LENGTH: 9
<212> TYPE: PRT
<213> ORGANISM: Artificial Sequence
<220> FEATURE:
<223> OTHER INFORMATION: LAGLIDADG motif

<400> SEQUENCE: 58

```
Leu Ala Gly Leu Ile Asp Ala Asp Gly
1               5
```

<210> SEQ ID NO 59
<211> LENGTH: 9
<212> TYPE: PRT
<213> ORGANISM: Artificial Sequence
<220> FEATURE:

```
<223> OTHER INFORMATION: Tag

<400> SEQUENCE: 59

Asn Trp Ser His Pro Gln Phe Glu Lys
1               5

<210> SEQ ID NO 60
<211> LENGTH: 10
<212> TYPE: PRT
<213> ORGANISM: Artificial Sequence
<220> FEATURE:
<223> OTHER INFORMATION: Tag

<400> SEQUENCE: 60

Ser Ala Trp Ser His Pro Gln Phe Glu Lys
1               5                   10

<210> SEQ ID NO 61
<211> LENGTH: 113
<212> TYPE: PRT
<213> ORGANISM: Artificial Sequence
<220> FEATURE:
<223> OTHER INFORMATION: CD3-zeta

<400> SEQUENCE: 61

Arg Val Lys Phe Ser Arg Ser Ala Asp Ala Pro Ala Tyr Lys Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 62
<211> LENGTH: 113
<212> TYPE: PRT
<213> ORGANISM: Artificial Sequence
<220> FEATURE:
<223> OTHER INFORMATION: CD3-zeta

<400> SEQUENCE: 62

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Gln Arg Arg Lys Asn Pro Gln Glu Gly Leu Tyr Asn Glu Leu Gln
        50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
```

```
                    85                  90                  95

Ala Thr Lys Asp Thr Tyr Asp Ala Leu His Met Gln Ala Leu Pro Pro
                100                 105                 110

Arg

<210> SEQ ID NO 63
<211> LENGTH: 223
<212> TYPE: PRT
<213> ORGANISM: Artificial Sequence
<220> FEATURE:
<223> OTHER INFORMATION: CAR

<400> SEQUENCE: 63

Ala Ala Ala Ile Glu Val Met Tyr Pro Pro Tyr Leu Asp Asn Glu
1               5                   10                  15

Lys Ser Asn Gly Thr Ile Ile His Val Lys Gly Lys His Leu Cys Pro
                20                  25                  30

Ser Pro Leu Phe Pro Gly Pro Ser Lys Pro Phe Trp Val Leu Val Val
            35                  40                  45

Val Gly Gly Val Leu Ala Cys Tyr Ser Leu Leu Val Thr Val Ala Phe
    50                  55                  60

Ile Ile Phe Trp Val Arg Ser Lys Arg Ser Arg Leu Leu His Ser Asp
65                  70                  75                  80

Tyr Met Asn Met Thr Pro Arg Arg Pro Gly Pro Thr Arg Lys His Tyr
                85                  90                  95

Gln Pro Tyr Ala Pro Pro Arg Asp Phe Ala Ala Tyr Arg Ser Arg Val
                100                 105                 110

Lys Phe Ser Arg Ser Ala Asp Ala Pro Ala Tyr Gln Gln Gly Gln Asn
            115                 120                 125

Gln Leu Tyr Asn Glu Leu Asn Leu Gly Arg Arg Glu Glu Tyr Asp Val
    130                 135                 140

Leu Asp Lys Arg Arg Gly Arg Asp Pro Glu Met Gly Gly Lys Pro Gln
145                 150                 155                 160

Arg Arg Lys Asn Pro Gln Glu Gly Leu Tyr Asn Glu Leu Gln Lys Asp
                165                 170                 175

Lys Met Ala Glu Ala Tyr Ser Glu Ile Gly Met Lys Gly Glu Arg Arg
                180                 185                 190

Arg Gly Lys Gly His Asp Gly Leu Tyr Gln Gly Leu Ser Thr Ala Thr
            195                 200                 205

Lys Asp Thr Tyr Asp Ala Leu His Met Gln Ala Leu Pro Pro Arg
    210                 215                 220

<210> SEQ ID NO 64
<211> LENGTH: 494
<212> TYPE: PRT
<213> ORGANISM: Artificial Sequence
<220> FEATURE:
<223> OTHER INFORMATION: CAR

<400> SEQUENCE: 64

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Gln Ala Ser Glu
            35                  40                  45

Asn Ile Tyr Ser Phe Leu Ala Trp Tyr Gln Gln Lys Pro Gly Lys Ala
```

```
                50                  55                  60
Pro Lys Leu Leu Ile Tyr Ser Ala Ser Lys Leu Ala Ala Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Thr
                100                 105                 110

Asn Arg Tyr Ser Asn Pro Asp Ile Tyr Asn Val Phe Gly Gln Gly Thr
                115                 120                 125

Lys Leu Thr Val Leu Gly Gly Gly Gly Ser Gly Gly Gly Gly Ser
                130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Ile
                165                 170                 175

Asp Phe Asn Ser Asn Tyr Tyr Met Cys Trp Val Arg Gln Ala Pro Gly
                180                 185                 190

Lys Gly Leu Glu Trp Ile Gly Cys Ile Tyr Val Gly Ser His Val Asn
                195                 200                 205

Thr Tyr Tyr Ala Asn Trp Ala Lys Gly Arg Phe Thr Ile Ser Arg Asp
                210                 215                 220

Asn Ser Lys Asn Thr Val Tyr Leu Gln Met Asn Ser Leu Arg Ala Glu
225                 230                 235                 240

Asp Thr Ala Val Tyr Tyr Cys Ala Thr Ser Gly Ser Ser Val Leu Tyr
                245                 250                 255

Phe Lys Phe Trp Gly Gln Gly Thr Leu Val Thr Val Ser Ser Thr Thr
                260                 265                 270

Thr Pro Ala Pro Arg Pro Thr Pro Ala Pro Thr Ile Ala Ser Gln
                275                 280                 285

Pro Leu Ser Leu Arg Pro Glu Ala Cys Arg Pro Ala Ala Gly Gly Ala
                290                 295                 300

Val His Thr Arg Gly Leu Asp Phe Ala Cys Asp Ile Tyr Ile Trp Ala
305                 310                 315                 320

Pro Leu Ala Gly Thr Cys Gly Val Leu Leu Leu Ser Leu Val Ile Thr
                325                 330                 335

Leu Tyr Cys Lys Arg Gly Arg Lys Lys Leu Leu Tyr Ile Phe Lys Gln
                340                 345                 350

Pro Phe Met Arg Pro Val Gln Thr Thr Gln Glu Glu Asp Gly Cys Ser
                355                 360                 365

Cys Arg Phe Pro Glu Glu Glu Gly Gly Cys Glu Leu Arg Val Lys
                370                 375                 380

Phe Ser Arg Ser Ala Asp Ala Pro Ala Tyr Gln Gln Gly Gln Asn Gln
385                 390                 395                 400

Leu Tyr Asn Glu Leu Asn Leu Gly Arg Arg Glu Glu Tyr Asp Val Leu
                405                 410                 415

Asp Lys Arg Arg Gly Arg Asp Pro Glu Met Gly Gly Lys Pro Gln Arg
                420                 425                 430

Arg Lys Asn Pro Gln Glu Gly Leu Tyr Asn Glu Leu Gln Lys Asp Lys
                435                 440                 445

Met Ala Glu Ala Tyr Ser Glu Ile Gly Met Lys Gly Glu Arg Arg Arg
450                 455                 460

Gly Lys Gly His Asp Gly Leu Tyr Gln Gly Leu Ser Thr Ala Thr Lys
465                 470                 475                 480
```

Asp Thr Tyr Asp Ala Leu His Met Gln Ala Leu Pro Pro Arg
            485                 490

<210> SEQ ID NO 65
<211> LENGTH: 473
<212> TYPE: PRT
<213> ORGANISM: Artificial Sequence
<220> FEATURE:
<223> OTHER INFORMATION: CAR

<400> SEQUENCE: 65

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser Thr Thr Pro Ala Pro Arg
                245                 250                 255

Pro Pro Thr Pro Ala Pro Thr Ile Ala Ser Gln Pro Leu Ser Leu Arg
            260                 265                 270

Pro Glu Ala Cys Arg Pro Ala Ala Gly Gly Ala Val His Thr Arg Gly
        275                 280                 285

Leu Asp Phe Ala Cys Asp Ile Tyr Ile Trp Ala Pro Leu Ala Gly Thr
    290                 295                 300

Cys Gly Val Leu Leu Leu Ser Leu Val Ile Thr Leu Tyr Cys Lys Arg
305                 310                 315                 320

Gly Arg Lys Lys Leu Leu Tyr Ile Phe Lys Gln Pro Phe Met Arg Pro
                325                 330                 335

Val Gln Thr Thr Gln Glu Glu Asp Gly Cys Ser Cys Arg Phe Pro Glu
            340                 345                 350

```
Glu Glu Glu Gly Gly Cys Glu Leu Arg Val Lys Phe Ser Arg Ser Ala
            355                 360                 365

Asp Ala Pro Ala Tyr Gln Gln Gly Gln Asn Gln Leu Tyr Asn Glu Leu
370                 375                 380

Asn Leu Gly Arg Arg Glu Glu Tyr Asp Val Leu Asp Lys Arg Arg Gly
385                 390                 395                 400

Arg Asp Pro Glu Met Gly Gly Lys Pro Gln Arg Arg Lys Asn Pro Gln
                405                 410                 415

Glu Gly Leu Tyr Asn Glu Leu Gln Lys Asp Lys Met Ala Glu Ala Tyr
            420                 425                 430

Ser Glu Ile Gly Met Lys Gly Glu Arg Arg Arg Gly Lys Gly His Asp
            435                 440                 445

Gly Leu Tyr Gln Gly Leu Ser Thr Ala Thr Lys Asp Thr Tyr Asp Ala
450                 455                 460

Leu His Met Gln Ala Leu Pro Pro Arg
465                 470

<210> SEQ ID NO 66
<211> LENGTH: 507
<212> TYPE: PRT
<213> ORGANISM: Artificial Sequence
<220> FEATURE:
<223> OTHER INFORMATION: CAR

<400> SEQUENCE: 66

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
                20                  25                  30

Ser Ala Ser Val Gly Asp Arg Val Thr Ile Thr Cys Gln Ala Ser Glu
            35                  40                  45

Asn Ile Tyr Ser Phe Leu Ala Trp Tyr Gln Gln Lys Pro Gly Lys Ala
        50                  55                  60

Pro Lys Leu Leu Ile Tyr Ser Ala Ser Lys Leu Ala Ala Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Thr
            100                 105                 110

Asn Arg Tyr Ser Asn Pro Asp Ile Tyr Asn Val Phe Gly Gln Gly Thr
        115                 120                 125

Lys Leu Thr Val Leu Gly Gly Gly Gly Ser Gly Gly Gly Gly Ser
130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Ile
                165                 170                 175

Asp Phe Asn Ser Asn Tyr Tyr Met Cys Trp Val Arg Gln Ala Pro Gly
            180                 185                 190

Lys Gly Leu Glu Trp Ile Gly Cys Ile Tyr Val Gly Ser His Val Asn
        195                 200                 205

Thr Tyr Tyr Ala Asn Trp Ala Lys Gly Arg Phe Thr Ile Ser Arg Asp
    210                 215                 220

Asn Ser Lys Asn Thr Val Tyr Leu Gln Met Asn Ser Leu Arg Ala Glu
225                 230                 235                 240
```

```
Asp Thr Ala Val Tyr Tyr Cys Ala Thr Ser Gly Ser Val Leu Tyr
                245                 250                 255

Phe Lys Phe Trp Gly Gln Gly Thr Leu Val Thr Val Ser Ser Asn Trp
            260                 265                 270

Ser His Pro Gln Phe Glu Lys Met His Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
    370                 375                 380

Glu Glu Glu Gly Gly Cys Glu Leu Thr Arg Arg Val Lys Phe Ser Arg
385                 390                 395                 400

Ser Ala Asp Ala Pro Ala Tyr Gln Gln Gly Gln Asn Gln Leu Tyr Asn
                405                 410                 415

Glu Leu Asn Leu Gly Arg Arg Glu Glu Tyr Asp Val Leu Asp Lys Arg
            420                 425                 430

Arg Gly Arg Asp Pro Glu Met Gly Gly Lys Pro Gln Arg Arg Lys Asn
        435                 440                 445

Pro Gln Glu Gly Leu Tyr Asn Glu Leu Gln Lys Asp Lys Met Ala Glu
    450                 455                 460

Ala Tyr Ser Glu Ile Gly Met Lys Gly Glu Arg Arg Arg Gly Lys Gly
465                 470                 475                 480

His Asp Gly Leu Tyr Gln Gly Leu Ser Thr Ala Thr Lys Asp Thr Tyr
                485                 490                 495

Asp Ala Leu His Met Gln Ala Leu Pro Pro Arg
            500                 505

<210> SEQ ID NO 67
<211> LENGTH: 486
<212> TYPE: PRT
<213> ORGANISM: Artificial Sequence
<220> FEATURE:
<223> OTHER INFORMATION: CAR

<400> SEQUENCE: 67

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95
```

```
Pro Asp Ile Tyr Asn Val Phe Gly Gln Gly Thr Lys Leu Thr Val Leu
                100                 105                 110

Gly Gly Gly Gly Ser Gly Gly Gly Ser Gly Gly Gly Ser
            115                 120                 125

Glu Val Gln Leu Val Glu Ser Gly Gly Gly Leu Val Gln Pro Gly Gly
            130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
            195                 200                 205

Val Tyr Leu Gln Met Asn Ser Leu Arg Ala Glu Asp Thr Ala Val Tyr
        210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser Asn Trp Ser His Pro Gln Phe
                245                 250                 255

Glu Lys Met His Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
        290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Lys Arg Gly Arg Lys Lys Leu
                325                 330                 335

Leu Tyr Ile Phe Lys Gln Pro Phe Met Arg Pro Val Gln Thr Thr Gln
            340                 345                 350

Glu Glu Asp Gly Cys Ser Cys Arg Phe Pro Glu Glu Glu Glu Gly Gly
            355                 360                 365

Cys Glu Leu Thr Arg Arg Val Lys Phe Ser Arg Ser Ala Asp Ala Pro
370                 375                 380

Ala Tyr Gln Gln Gly Gln Asn Gln Leu Tyr Asn Glu Leu Asn Leu Gly
385                 390                 395                 400

Arg Arg Glu Glu Tyr Asp Val Leu Asp Lys Arg Arg Gly Arg Asp Pro
                405                 410                 415

Glu Met Gly Gly Lys Pro Gln Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
        450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 68
<211> LENGTH: 497
```

-continued

```
<212> TYPE: PRT
<213> ORGANISM: Artificial Sequence
<220> FEATURE:
<223> OTHER INFORMATION: CAR

<400> SEQUENCE: 68

Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Gln Ala Ser Glu
        35                  40                  45

Asn Ile Tyr Ser Phe Leu Ala Trp Tyr Gln Gln Lys Pro Gly Lys Ala
    50                  55                  60

Pro Lys Leu Leu Ile Tyr Ser Ala Ser Lys Leu Ala Ala Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Thr
            100                 105                 110

Asn Arg Tyr Ser Asn Pro Asp Ile Tyr Asn Val Phe Gly Gln Gly Thr
        115                 120                 125

Lys Leu Thr Val Leu Gly Gly Gly Gly Ser Gly Gly Gly Gly Ser
130                 135                 140

Gly Gly Gly Gly Ser Glu Val Gln Leu Val Glu Ser Gly Gly Gly Leu
145                 150                 155                 160

Val Gln Pro Gly Gly Ser Leu Arg Leu Ser Cys Ala Ala Ser Gly Ile
                165                 170                 175

Asp Phe Asn Ser Asn Tyr Tyr Met Cys Trp Val Arg Gln Ala Pro Gly
            180                 185                 190

Lys Gly Leu Glu Trp Ile Gly Cys Ile Tyr Val Gly Ser His Val Asn
        195                 200                 205

Thr Tyr Tyr Ala Asn Trp Ala Lys Gly Arg Phe Thr Ile Ser Arg Asp
    210                 215                 220

Asn Ser Lys Asn Thr Val Tyr Leu Gln Met Asn Ser Leu Arg Ala Glu
225                 230                 235                 240

Asp Thr Ala Val Tyr Tyr Cys Ala Thr Gly Ser Ser Val Leu Tyr
                245                 250                 255

Phe Lys Phe Trp Gly Gln Gly Thr Leu Val Thr Val Ser Ser Met His
            260                 265                 270

Thr Thr Thr Pro Ala Pro Arg Pro Thr Pro Ala Pro Thr Ile Ala
        275                 280                 285

Ser Gln Pro Leu Ser Leu Arg Pro Glu Ala Cys Arg Pro Ala Ala Gly
    290                 295                 300

Gly Ala Val His Thr Arg Gly Leu Asp Phe Ala Cys Asp Ile Tyr Ile
305                 310                 315                 320

Trp Ala Pro Leu Ala Gly Thr Cys Gly Val Leu Leu Leu Ser Leu Val
                325                 330                 335

Ile Thr Leu Tyr Cys Arg Ser Lys Arg Ser Arg Leu Leu His Ser Asp
            340                 345                 350

Tyr Met Asn Met Thr Pro Arg Arg Pro Gly Pro Thr Arg Lys His Tyr
        355                 360                 365

Gln Pro Tyr Ala Pro Pro Arg Asp Phe Ala Ala Tyr Arg Ser Thr Arg
    370                 375                 380
```

-continued

```
Arg Val Lys Phe Ser Arg Ser Ala Asp Ala Pro Ala Tyr Gln Gln Gly
385                 390                 395                 400

Gln Asn Gln Leu Tyr Asn Glu Leu Asn Leu Gly Arg Arg Glu Glu Tyr
            405                 410                 415

Asp Val Leu Asp Lys Arg Arg Gly Arg Asp Pro Glu Met Gly Gly Lys
        420                 425                 430

Pro Gln Arg Arg Lys Asn Pro Gln Glu Gly Leu Tyr Asn Glu Leu Gln
    435                 440                 445

Lys Asp Lys Met Ala Glu Ala Tyr Ser Glu Ile Gly Met Lys Gly Glu
450                 455                 460

Arg Arg Arg Gly Lys Gly His Asp Gly Leu Tyr Gln Gly Leu Ser Thr
465                 470                 475                 480

Ala Thr Lys Asp Thr Tyr Asp Ala Leu His Met Gln Ala Leu Pro Pro
                485                 490                 495

Arg
```

<210> SEQ ID NO 69
<211> LENGTH: 476
<212> TYPE: PRT
<213> ORGANISM: Artificial Sequence
<220> FEATURE:
<223> OTHER INFORMATION: CAR

<400> SEQUENCE: 69

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser Met His Thr Thr Thr Pro Ala
```

```
                    245                 250                 255
Pro Arg Pro Thr Pro Ala Pro Thr Ile Ala Ser Gln Pro Leu Ser
            260                 265                 270

Leu Arg Pro Glu Ala Cys Arg Pro Ala Ala Gly Gly Ala Val His Thr
            275                 280                 285

Arg Gly Leu Asp Phe Ala Cys Asp Ile Tyr Ile Trp Ala Pro Leu Ala
            290                 295                 300

Gly Thr Cys Gly Val Leu Leu Leu Ser Leu Val Ile Thr Leu Tyr Cys
305                 310                 315                 320

Arg Ser Lys Arg Ser Arg Leu Leu His Ser Asp Tyr Met Asn Met Thr
            325                 330                 335

Pro Arg Arg Pro Gly Pro Thr Arg Lys His Tyr Gln Pro Tyr Ala Pro
            340                 345                 350

Pro Arg Asp Phe Ala Ala Tyr Arg Ser Thr Arg Arg Val Lys Phe Ser
            355                 360                 365

Arg Ser Ala Asp Ala Pro Ala Tyr Gln Gln Gly Gln Asn Gln Leu Tyr
            370                 375                 380

Asn Glu Leu Asn Leu Gly Arg Arg Glu Glu Tyr Asp Val Leu Asp Lys
385                 390                 395                 400

Arg Arg Gly Arg Asp Pro Glu Met Gly Gly Lys Pro Gln Arg Arg Lys
            405                 410                 415

Asn Pro Gln Glu Gly Leu Tyr Asn Glu Leu Gln Lys Asp Lys Met Ala
            420                 425                 430

Glu Ala Tyr Ser Glu Ile Gly Met Lys Gly Glu Arg Arg Arg Gly Lys
            435                 440                 445

Gly His Asp Gly Leu Tyr Gln Gly Leu Ser Thr Ala Thr Lys Asp Thr
            450                 455                 460

Tyr Asp Ala Leu His Met Gln Ala Leu Pro Pro Arg
465                 470                 475

<210> SEQ ID NO 70
<211> LENGTH: 224
<212> TYPE: PRT
<213> ORGANISM: Artificial Sequence
<220> FEATURE:
<223> OTHER INFORMATION: CAR

<400> SEQUENCE: 70

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
        50                  55                  60

Ile Thr Leu Tyr Cys Lys Arg Gly Arg Lys Lys Leu Leu Tyr Ile Phe
65                  70                  75                  80

Lys Gln Pro Phe Met Arg Pro Val Gln Thr Thr Gln Glu Glu Asp Gly
                85                  90                  95

Cys Ser Cys Arg Phe Pro Glu Glu Glu Glu Gly Gly Cys Glu Leu Arg
            100                 105                 110

Val Lys Phe Ser Arg Ser Ala Asp Ala Pro Ala Tyr Gln Gln Gly Gln
            115                 120                 125

Asn Gln Leu Tyr Asn Glu Leu Asn Leu Gly Arg Arg Glu Glu Tyr Asp
```

```
                130             135             140
Val Leu Asp Lys Arg Arg Gly Arg Asp Pro Glu Met Gly Gly Lys Pro
145                 150                 155                 160

Gln Arg Arg Lys Asn Pro Gln Glu Gly Leu Tyr Asn Glu Leu Gln Lys
                165                 170                 175

Asp Lys Met Ala Glu Ala Tyr Ser Glu Ile Gly Met Lys Gly Glu Arg
            180                 185                 190

Arg Arg Gly Lys Gly His Asp Gly Leu Tyr Gln Gly Leu Ser Thr Ala
                195                 200                 205

Thr Lys Asp Thr Tyr Asp Ala Leu His Met Gln Ala Leu Pro Pro Arg
            210                 215                 220
```

<210> SEQ ID NO 71
<211> LENGTH: 237
<212> TYPE: PRT
<213> ORGANISM: Artificial Sequence
<220> FEATURE:
<223> OTHER INFORMATION: CAR

<400> SEQUENCE: 71

```
Asn Trp Ser His Pro Gln Phe Glu Lys Met His Thr Thr Thr Pro Ala
1               5                   10                  15

Pro Arg Pro Pro Thr Pro Ala Pro Thr Ile Ala Ser Gln Pro Leu Ser
                20                  25                  30

Leu Arg Pro Glu Ala Cys Arg Pro Ala Ala Gly Gly Ala Val His Thr
            35                  40                  45

Arg Gly Leu Asp Phe Ala Cys Asp Ile Tyr Ile Trp Ala Pro Leu Ala
        50                  55                  60

Gly Thr Cys Gly Val Leu Leu Leu Ser Leu Val Ile Thr Leu Tyr Cys
65                  70                  75                  80

Lys Arg Gly Arg Lys Lys Leu Leu Tyr Ile Phe Lys Gln Pro Phe Met
                85                  90                  95

Arg Pro Val Gln Thr Thr Gln Glu Glu Asp Gly Cys Ser Cys Arg Phe
                100                 105                 110

Pro Glu Glu Glu Glu Gly Gly Cys Glu Leu Thr Arg Arg Val Lys Phe
            115                 120                 125

Ser Arg Ser Ala Asp Ala Pro Ala Tyr Gln Gln Gly Gln Asn Gln Leu
        130                 135                 140

Tyr Asn Glu Leu Asn Leu Gly Arg Arg Glu Glu Tyr Asp Val Leu Asp
145                 150                 155                 160

Lys Arg Arg Gly Arg Asp Pro Glu Met Gly Gly Lys Pro Gln Arg Arg
                165                 170                 175

Lys Asn Pro Gln Glu Gly Leu Tyr Asn Glu Leu Gln Lys Asp Lys Met
                180                 185                 190

Ala Glu Ala Tyr Ser Glu Ile Gly Met Lys Gly Glu Arg Arg Arg Gly
            195                 200                 205

Lys Gly His Asp Gly Leu Tyr Gln Gly Leu Ser Thr Ala Thr Lys Asp
        210                 215                 220

Thr Tyr Asp Ala Leu His Met Gln Ala Leu Pro Pro Arg
225                 230                 235
```

<210> SEQ ID NO 72
<211> LENGTH: 227
<212> TYPE: PRT
<213> ORGANISM: Artificial Sequence
<220> FEATURE:
<223> OTHER INFORMATION: CAR

<400> SEQUENCE: 72

```
Met His Thr Thr Thr Pro Ala Pro Arg Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp Phe Ala Cys Asp Ile
        35                  40                  45

Tyr Ile Trp Ala Pro Leu Ala Gly Thr Cys Gly Val Leu Leu Leu Ser
    50                  55                  60

Leu Val Ile Thr Leu Tyr Cys Arg Ser Lys Arg Ser Arg Leu Leu His
65                  70                  75                  80

Ser Asp Tyr Met Asn Met Thr Pro Arg Arg Pro Gly Pro Thr Arg Lys
                85                  90                  95

His Tyr Gln Pro Tyr Ala Pro Pro Arg Asp Phe Ala Ala Tyr Arg Ser
            100                 105                 110

Thr Arg Arg Val Lys Phe Ser Arg Ser Ala Asp Ala Pro Ala Tyr Gln
        115                 120                 125

Gln Gly Gln Asn Gln Leu Tyr Asn Glu Leu Asn Leu Gly Arg Arg Glu
    130                 135                 140

Glu Tyr Asp Val Leu Asp Lys Arg Arg Gly Arg Asp Pro Glu Met Gly
145                 150                 155                 160

Gly Lys Pro Gln Arg Arg Lys Asn Pro Gln Glu Gly Leu Tyr Asn Glu
                165                 170                 175

Leu Gln Lys Asp Lys Met Ala Glu Ala Tyr Ser Glu Ile Gly Met Lys
            180                 185                 190

Gly Glu Arg Arg Arg Gly Lys Gly His Asp Gly Leu Tyr Gln Gly Leu
        195                 200                 205

Ser Thr Ala Thr Lys Asp Thr Tyr Asp Ala Leu His Met Gln Ala Leu
    210                 215                 220

Pro Pro Arg
225
```

<210> SEQ ID NO 73
<211> LENGTH: 506
<212> TYPE: PRT
<213> ORGANISM: Artificial Sequence
<220> FEATURE:
<223> OTHER INFORMATION: CAR

<400> SEQUENCE: 73

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Gln Ala Ser Glu
        35                  40                  45

Asn Ile Tyr Ser Phe Leu Ala Trp Tyr Gln Gln Lys Pro Gly Lys Ala
    50                  55                  60

Pro Lys Leu Leu Ile Tyr Ser Ala Ser Lys Leu Ala Ala Gly Val Pro
65                  70                  75                  80

Ser Arg Phe Ser Gly Ser Gly Ser Gly Thr Asp Phe Thr Leu Thr Ile
                85                  90                  95

Ser Ser Leu Gln Pro Glu Asp Phe Ala Thr Tyr Tyr Cys Gln Gln Thr
            100                 105                 110
```

```
Asn Arg Tyr Ser Asn Pro Asp Ile Tyr Asn Val Phe Gly Gln Gly Thr
            115                 120                 125
Lys Leu Thr Val Leu Gly Gly Gly Gly Ser Gly Gly Gly Gly Ser
130                 135                 140
Gly Gly Gly Gly Ser Glu Val Gln Leu Val Glu Ser Gly Gly Gly Leu
145                 150                 155                 160
Val Gln Pro Gly Gly Ser Leu Arg Leu Ser Cys Ala Ala Ser Gly Ile
                165                 170                 175
Asp Phe Asn Ser Asn Tyr Met Cys Trp Val Arg Gln Ala Pro Gly
            180                 185                 190
Lys Gly Leu Glu Trp Ile Gly Cys Ile Tyr Val Gly Ser His Val Asn
    195                 200                 205
Thr Tyr Tyr Ala Asn Trp Ala Lys Gly Arg Phe Thr Ile Ser Arg Asp
210                 215                 220
Asn Ser Lys Asn Thr Val Tyr Leu Gln Met Asn Ser Leu Arg Ala Glu
225                 230                 235                 240
Asp Thr Ala Val Tyr Tyr Cys Ala Thr Ser Gly Ser Ser Val Leu Tyr
                245                 250                 255
Phe Lys Phe Trp Gly Gln Gly Thr Leu Val Thr Val Ser Ser Asn Trp
                260                 265                 270
Ser His Pro Gln Phe Glu Lys Met His Thr Thr Thr Pro Ala Pro Arg
    275                 280                 285
Pro Pro Thr Pro Ala Pro Thr Ile Ala Ser Gln Pro Leu Ser Leu Arg
        290                 295                 300
Pro Glu Ala Cys Arg Pro Ala Ala Gly Gly Ala Val His Thr Arg Gly
305                 310                 315                 320
Leu Asp Phe Ala Cys Asp Ile Tyr Ile Trp Ala Pro Leu Ala Gly Thr
                325                 330                 335
Cys Gly Val Leu Leu Leu Ser Leu Val Ile Thr Leu Tyr Cys Arg Ser
                340                 345                 350
Lys Arg Ser Arg Leu Leu His Ser Asp Tyr Met Asn Met Thr Pro Arg
            355                 360                 365
Arg Pro Gly Pro Thr Arg Lys His Tyr Gln Pro Tyr Ala Pro Pro Arg
370                 375                 380
Asp Phe Ala Ala Tyr Arg Ser Thr Arg Arg Val Lys Phe Ser Arg Ser
385                 390                 395                 400
Ala Asp Ala Pro Ala Tyr Gln Gln Gly Gln Asn Gln Leu Tyr Asn Glu
                405                 410                 415
Leu Asn Leu Gly Arg Arg Glu Glu Tyr Asp Val Leu Asp Lys Arg Arg
                420                 425                 430
Gly Arg Asp Pro Glu Met Gly Gly Lys Pro Gln Arg Arg Lys Asn Pro
            435                 440                 445
Gln Glu Gly Leu Tyr Asn Glu Leu Gln Lys Asp Lys Met Ala Glu Ala
        450                 455                 460
Tyr Ser Glu Ile Gly Met Lys Gly Glu Arg Arg Arg Gly Lys Gly His
465                 470                 475                 480
Asp Gly Leu Tyr Gln Gly Leu Ser Thr Ala Thr Lys Asp Thr Tyr Asp
                485                 490                 495
Ala Leu His Met Gln Ala Leu Pro Pro Arg
                500                 505

<210> SEQ ID NO 74
<211> LENGTH: 485
<212> TYPE: PRT
```

<213> ORGANISM: Artificial Sequence
<220> FEATURE:
<223> OTHER INFORMATION: CAR

<400> SEQUENCE: 74

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Gln Gly Thr Lys Leu Thr Val Leu
            100                 105                 110

Gly Gly Gly Gly Ser Gly Gly Gly Ser Gly Gly Gly Gly Ser
        115                 120                 125

Glu Val Gln Leu Val Glu Ser Gly Gly Leu Val Gln Pro Gly Gly
    130                 135                 140

Ser Leu Arg Leu Ser Cys Ala Ala Ser Gly Ile Asp Phe Asn Ser Asn
145                 150                 155                 160

Tyr Tyr Met Cys Trp Val Arg Gln Ala Pro Gly Lys Gly Leu Glu Trp
                165                 170                 175

Ile Gly Cys Ile Tyr Val Gly Ser His Val Asn Thr Tyr Tyr Ala Asn
            180                 185                 190

Trp Ala Lys Gly Arg Phe Thr Ile Ser Arg Asp Asn Ser Lys Asn Thr
        195                 200                 205

Val Tyr Leu Gln Met Asn Ser Leu Arg Ala Glu Asp Thr Ala Val Tyr
    210                 215                 220

Tyr Cys Ala Thr Ser Gly Ser Ser Val Leu Tyr Phe Lys Phe Trp Gly
225                 230                 235                 240

Gln Gly Thr Leu Val Thr Val Ser Ser Asn Trp Ser His Pro Gln Phe
                245                 250                 255

Glu Lys Met His Thr Thr Thr Pro Ala Pro Arg Pro Pro Thr Pro Ala
            260                 265                 270

Pro Thr Ile Ala Ser Gln Pro Leu Ser Leu Arg Pro Glu Ala Cys Arg
        275                 280                 285

Pro Ala Ala Gly Gly Ala Val His Thr Arg Gly Leu Asp Phe Ala Cys
    290                 295                 300

Asp Ile Tyr Ile Trp Ala Pro Leu Ala Gly Thr Cys Gly Val Leu Leu
305                 310                 315                 320

Leu Ser Leu Val Ile Thr Leu Tyr Cys Arg Ser Lys Arg Ser Arg Leu
                325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
        355                 360                 365

Arg Ser Thr Arg Arg Val Lys Phe Ser Arg Ser Ala Asp Ala Pro Ala
    370                 375                 380

Tyr Gln Gln Gly Gln Asn Gln Leu Tyr Asn Glu Leu Asn Leu Gly Arg
```

```
                385                 390                 395                 400
Arg Glu Glu Tyr Asp Val Leu Asp Lys Arg Arg Gly Arg Asp Pro Glu
                    405                 410                 415

Met Gly Gly Lys Pro Gln Arg Arg Lys Asn Pro Gln Glu Gly Leu Tyr
                420                 425                 430

Asn Glu Leu Gln Lys Asp Lys Met Ala Glu Ala Tyr Ser Glu Ile Gly
                435                 440                 445

Met Lys Gly Glu Arg Arg Arg Gly Lys Gly His Asp Gly Leu Tyr Gln
            450                 455                 460

Gly Leu Ser Thr Ala Thr Lys Asp Thr Tyr Asp Ala Leu His Met Gln
465                 470                 475                 480

Ala Leu Pro Pro Arg
                485

<210> SEQ ID NO 75
<211> LENGTH: 4
<212> TYPE: PRT
<213> ORGANISM: Artificial Sequence
<220> FEATURE:
<223> OTHER INFORMATION: Cys2His2

<400> SEQUENCE: 75

Cys Cys His His
1

<210> SEQ ID NO 76
<211> LENGTH: 135
<212> TYPE: PRT
<213> ORGANISM: Artificial Sequence
<220> FEATURE:
<223> OTHER INFORMATION: Peptide comprising a marker moiety and a
      suicide moiety

<400> SEQUENCE: 76

Cys Pro Tyr Ser Asn Pro Ser Leu Cys Ser Gly Gly Gly Gly Ser Glu
1               5                   10                  15

Leu Pro Thr Gln Gly Thr Phe Ser Asn Val Ser Thr Asn Val Ser Pro
                20                  25                  30

Ala Lys Pro Thr Thr Thr Ala Cys Pro Tyr Ser Asn Pro Ser Leu Cys
            35                  40                  45

Ser Gly Gly Gly Gly Ser Pro Ala Pro Arg Pro Pro Thr Pro Ala Pro
        50                  55                  60

Thr Ile Ala Ser Gln Pro Leu Ser Leu Arg Pro Glu Ala Cys Arg Pro
65                  70                  75                  80

Ala Ala Gly Gly Ala Val His Thr Arg Gly Leu Asp Phe Ala Cys Asp
                85                  90                  95

Ile Tyr Ile Trp Ala Pro Leu Ala Gly Thr Cys Gly Val Leu Leu Leu
                100                 105                 110

Ser Leu Val Ile Thr Leu Tyr Cys Asn His Arg Asn Arg Arg Arg Val
            115                 120                 125

Cys Lys Cys Pro Arg Pro Trp
        130                 135

<210> SEQ ID NO 77
<211> LENGTH: 1479
<212> TYPE: DNA
<213> ORGANISM: Artificial Sequence
<220> FEATURE:
<223> OTHER INFORMATION: CAR
```

<400> SEQUENCE: 77

```
atggctctgc ctgtgacagc tctgctgctg cctctggctc tgcttcttca tgccgccaga      60
ccatctgagg tgcagctagt tgaatctggt ggaggcctgg ttcagcctgg tggctctctg     120
agactgtctt gtgccgccag cggcatcgac ttcaacagca actactacat gtgctgggtc     180
cgacaggccc ccggcaaagg acttgaatgg attggctgca tctacgtggg cagccatgtg     240
aacacctact acgcaaactg ggccaagggc agattcacca tcagccggga caacagcaag     300
aacaccgtgt acctgcagat gaacagcctg agagcagaag atactgccgt gtactactgt     360
gccacatctg gcagcagcgt gctgtacttc aagttctggg gccagggcac cctggtcaca     420
gtttcttcag gaggtggagg ctctggcggt ggaggaagtg gtggggagg ctctgacatc      480
cagatgacac agagcccag cagcctgtct gcctctgtgg agacagagt gaccatcact       540
tgccaggcca gcgagaacat ctacagcttc ctggcctggt accagcagaa gccaggcaag     600
gcccctaagc tgctgatcta cgcgcctct aaactagctg ccggggtgcc aagcagattt      660
tctggctctg gcagcggcac cgacttcacc ctgaccatat caagcctgca gcctgaggac     720
ttcgccacct actactgcca gcagaccaac aggtacagca ccccgacat ctacaacgtg      780
tttggacagg gcaccaagct gacagtgctt ggaatgcata tcgagttcat gtaccctcca     840
ccttacctgg acaacgagag aagcaacggc accatcatcc acatcaaaga gaagcacctc     900
tgtcacaccc agagcagccc aagctgtttt gggctcttg tggtggtggc tggcgtgctg      960
ttttgttacg gcctgctggt cacagtggcc ctgtgtgtga tttggaccac gcgtaacagc    1020
agaagaaaca gaggcggaca gagcgactac atgaacatga cccctagacg gcctggcctg    1080
acaagaaagc cctaccagcc ttacgctccc gccagagatt cgccgccta cagacctaga    1140
gccaagttca gcagatccgc cgaaacagcc gccaacttgc aagatcctaa ccagctgtac    1200
aacgagctga acctggggag aagagaagag tacgacgtgc tggaaaagaa gagggccaga    1260
gatccagaga tggcggcaa gcagcagaga agaagaaacc ctcaagaggg cgtgtacaac    1320
gctctgcaaa aagacaagat ggccgaggcc tacagcgaga tcggaactaa gggcgaacgc    1380
agaagaggca aggccacga tggactgtac cagggcctga gcacagccac caaggacaca    1440
tacgatgccc tgcacatgca gacactggcc cctagatag                            1479
```

<210> SEQ ID NO 78
<211> LENGTH: 492
<212> TYPE: PRT
<213> ORGANISM: Artificial Sequence
<220> FEATURE:
<223> OTHER INFORMATION: CAR

<400> SEQUENCE: 78

```
Met Ala Leu Pro Val Thr Ala Leu Leu Leu Pro Leu Ala Leu Leu Leu
1               5                   10                  15

His Ala Ala Arg Pro Ser Glu Val Gln Leu Val Glu Ser Gly Gly Gly
            20                  25                  30

Leu Val Gln Pro Gly Gly Ser Leu Arg Leu Ser Cys Ala Ala Ser Gly
        35                  40                  45

Ile Asp Phe Asn Ser Asn Tyr Tyr Met Cys Trp Val Arg Gln Ala Pro
    50                  55                  60

Gly Lys Gly Leu Glu Trp Ile Gly Cys Ile Tyr Val Gly Ser His Val
65                  70                  75                  80

Asn Thr Tyr Tyr Ala Asn Trp Ala Lys Gly Arg Phe Thr Ile Ser Arg
                85                  90                  95
```

```
Asp Asn Ser Lys Asn Thr Val Tyr Leu Gln Met Asn Ser Leu Arg Ala
            100                 105                 110

Glu Asp Thr Ala Val Tyr Tyr Cys Ala Thr Ser Gly Ser Ser Val Leu
            115                 120                 125

Tyr Phe Lys Phe Trp Gly Gln Gly Thr Leu Val Thr Val Ser Ser Gly
            130                 135                 140

Gly Gly Gly Ser Gly Gly Gly Gly Ser Gly Gly Gly Gly Ser Asp Ile
145                 150                 155                 160

Gln Met Thr Gln Ser Pro Ser Ser Leu Ser Ala Ser Val Gly Asp Arg
                165                 170                 175

Val Thr Ile Thr Cys Gln Ala Ser Glu Asn Ile Tyr Ser Phe Leu Ala
            180                 185                 190

Trp Tyr Gln Gln Lys Pro Gly Lys Ala Pro Lys Leu Leu Ile Tyr Ser
            195                 200                 205

Ala Ser Lys Leu Ala Ala Gly Val Pro Ser Arg Phe Ser Gly Ser Gly
            210                 215                 220

Ser Gly Thr Asp Phe Thr Leu Thr Ile Ser Ser Leu Gln Pro Glu Asp
225                 230                 235                 240

Phe Ala Thr Tyr Tyr Cys Gln Gln Thr Asn Arg Tyr Ser Asn Pro Asp
                245                 250                 255

Ile Tyr Asn Val Phe Gly Gln Gly Thr Lys Leu Thr Val Leu Gly Met
            260                 265                 270

His Ile Glu Phe Met Tyr Pro Pro Tyr Leu Asp Asn Glu Arg Ser
            275                 280                 285

Asn Gly Thr Ile Ile His Ile Lys Glu Lys His Leu Cys His Thr Gln
290                 295                 300

Ser Ser Pro Lys Leu Phe Trp Ala Leu Val Val Val Ala Gly Val Leu
305                 310                 315                 320

Phe Cys Tyr Gly Leu Leu Val Thr Val Ala Leu Cys Val Ile Trp Thr
                325                 330                 335

Thr Arg Asn Ser Arg Arg Asn Arg Gly Gly Gln Ser Asp Tyr Met Asn
                340                 345                 350

Met Thr Pro Arg Arg Pro Gly Leu Thr Arg Lys Pro Tyr Gln Pro Tyr
            355                 360                 365

Ala Pro Ala Arg Asp Phe Ala Ala Tyr Arg Pro Arg Ala Lys Phe Ser
            370                 375                 380

Arg Ser Ala Glu Thr Ala Ala Asn Leu Gln Asp Pro Asn Gln Leu Tyr
385                 390                 395                 400

Asn Glu Leu Asn Leu Gly Arg Arg Glu Glu Tyr Asp Val Leu Glu Lys
                405                 410                 415

Lys Arg Ala Arg Asp Pro Glu Met Gly Gly Lys Gln Arg Arg Arg
            420                 425                 430

Asn Pro Gln Glu Gly Val Tyr Asn Ala Leu Gln Lys Asp Lys Met Ala
            435                 440                 445

Glu Ala Tyr Ser Glu Ile Gly Thr Lys Gly Glu Arg Arg Arg Gly Lys
            450                 455                 460

Gly His Asp Gly Leu Tyr Gln Gly Leu Ser Thr Ala Thr Lys Asp Thr
465                 470                 475                 480

Tyr Asp Ala Leu His Met Gln Thr Leu Ala Pro Arg
            485                 490
```

CHIMERIC ANTIGEN RECEPTOR SPECIFIC FOR INTERLEUKIN-23 RECEPTOR

CROSS-REFERENCE TO RELATED APPLICATIONS

This application is a national stage application under 35 U.S.C. § 371 of International Patent Application No. PCT/EP2019/059590, filed Apr. 15, 2019, which claims the benefit of U.S. Provisional Patent Application No. 62/657,233, filed Apr. 13, 2018. The disclosures of those applications are incorporated by reference herein in their entirety.

SEQUENCE LISTING

The instant application contains a Sequence Listing which has been submitted electronically in ASCII format and is hereby incorporated by reference in its entirety. The electronic copy of the Sequence Listing, created on Oct. 13, 2020, is named 025297_US007_SL.txt and is 129,564 bytes in size.

FIELD OF INVENTION

The present invention relates to the field of immunotherapy. In particular, the present invention relates to a chimeric antigen receptor (CAR) specific for interleukin-23 receptor, to T cells expressing said CAR and to the use thereof for treating an autoimmune and/or inflammatory disease or disorder.

BACKGROUND OF THE INVENTION

The interleukin-23 (IL-23), a member of IL-12 cytokine family, is composed of two subunits, p19 and p40. The receptor for IL-23 (IL-23R) consists of an IL-23Rα subunit in complex with an IL-12Rβ1 subunit, which is a common subunit for the IL-12 receptor and interacts with Tyrosine kinase 2 (Tyk2). The IL-23R is associated constitutively with Janus Kinase 2 (JAK2) and associates with STAT3 and STAT4 upon its activation by IL-23.

The IL-23R is mainly expressed on immune cells, in particular T cells (e.g., Th17 and γδ T cells), macrophages, dendritic cells and NK cells (Duvallet et al., 2011). It has been recently shown that non-activated neutrophils express a basal amount of IL-23R and that IL-23R expression is increased upon cell activation (Chen et al., 2016).

IL-23R activation by IL-23 induces IL-23R phosphorylation as well as the recruitment of STAT3 and STAT4 forming homodimers that, once phosphorylated, translocate to nucleus and consequently induce the expression of the transcription factor RORγt. RORγt, in turn, activates the transcription of downstream pro-inflammatory cytokines such as IL-17A, IL-17F, IL-22, IL-6 and IFN-γ that are involved in the activation of the immune response (Razawy et al., 2018, Sivanesan et al., 2016 and Duvallet et al., 2011). In particular, the IL-23/IL-23R signaling pathway has been described as critical for promoting the proliferation and the differentiation of IL-17-secreting immune cells, in particular CD4+ Th17 cells and γδ T cells.

In the art, the expression of IL23R has been described as a common feature of pathogenic inflammatory cells involved in the appearance and maintenance of autoimmune diseases and chronic inflammation. Expression of IL23R at the surface is induced by IL23 exposure, and depends on inflammation levels. In human cells, whereas expression of IL23R at the RNA level is well documented, little was shown regarding the presence of the protein on the cell surface, and thus regarding its availability for a targeting agent.

The inhibition of IL-23/IL-23R signaling pathway has been investigated as a possible therapeutic approach for autoimmune and inflammatory diseases or disorders. In particular, Ustekinumab, an antibody directed to IL-12p40 subunit, has been tested with successful results on non-responsive patients with Crohn's disease and on patients with psoriasis (Fegan et al., 2016, Mease et al., 2015). Ustekinumab has been approved as a treatment for psoriasis in the United States. However, a case report revealed that psoriatic arthritis had been worsen in 4 patients following the treatment with Ustekinumab (Simon et al., 2016).

In addition, for a long-term treatment of autoimmune and/or inflammatory diseases or disorders, induction of tolerance is required, which may not be obtained when targeting the cytokine.

There is consequently still a need for a method for inhibiting the IL-23/IL-23R signaling pathway, thereby treating autoimmune and/or inflammatory diseases or disorders, that does not present the drawbacks of the method of the prior art.

The applicant herein provides a chimeric antigen receptor (CAR) directed to IL-23R and a Treg cell population expressing said IL-23R CAR. Said Treg cell population may in particular be used for treating diseases or disorders related to IL-23R expressing cells, in particular autoimmune and/or inflammatory diseases or disorders.

SUMMARY

The present invention relates to a chimeric antigen receptor (CAR) specific for at least one IL-23 receptor (IL-23R), wherein said CAR comprises:
 (i) an extracellular binding domain, wherein said binding domain binds to said IL-23R,
 (ii) optionally an extracellular hinge domain,
 (iii) a transmembrane domain,
 (iv) an intracellular signaling domain, and,
 (v) optionally a tag and/or a leader sequence.

In one embodiment, the extracellular binding domain comprises a scFv fragment directed against said IL-23R.

In one embodiment, the extracellular binding domain comprises a scFv fragment directed against said IL-23R, wherein said scFv comprises
 a heavy chain variable domain (VH) having the sequence of SEQ ID NO: 37 or a sequence having at least about 70% identity to SEQ ID NO: 37
 a light chain variable domain (VL) having a sequence selected from the group comprising or consisting of SEQ ID NOs: 38, 46 and 56 and sequences having at least about 70% identity to said SEQ ID NO: 38, 46 or 56, and
 optionally a linker between the VH and VL.

In one embodiment, the extracellular binding domain comprises a scFv fragment directed against said IL-23R wherein the scFv has a sequence SEQ ID NO: 55 or a sequence having at least about 70% identity with SEQ ID NO: 55.

In one embodiment, the hinge domain is a hinge region of human CD8, preferably having the sequence of SEQ ID NO: 13 or a sequence having at least about 70% identity to SEQ ID NO: 13.

In one embodiment, the transmembrane domain is a transmembrane domain derived from the human CD8a, preferably having the sequence of SEQ ID NO: 21 or a sequence having at least about 70% identity to SEQ ID NO: 21.

In one embodiment, the intracellular signaling domain comprises a costimulatory signaling domain of human 4-1BB, preferably having the sequence of SEQ ID NO: 29 or a sequence having at least about 70% identity to SEQ ID NO: 29 and a T cell primary signaling human CD3 zeta, preferably having the sequence of SEQ ID NO: 26 or a sequence having at least 70% identity to SEQ ID NO: 26.

In one embodiment, the CAR of the invention comprises:
(i) an anti-IL-23R scFv, preferably comprising a VH having the sequence of SEQ ID NO: 37 and a VL having the sequence of SEQ ID NO: 38, linked by a $(G_4S)_3$ linker (SEQ ID NO: 3),
(ii) a hinge domain derived from CD8a, preferably SEQ ID NO: 13,
(iii) a human CD8a transmembrane domain, preferably SEQ ID NO: 21,
(iv) an intracellular signaling domain comprising a human 4-1BB signaling domain, preferably SEQ ID NO: 29 and a human CD3 zeta domain, preferably SEQ ID NO: 26, and
(v) optionally a tag and/or a leader sequence.

The present invention further relates to a nucleic acid sequence encoding a CAR as described hereinabove.

The present invention further relates to a vector comprising the nucleic acid sequence as described hereinabove.

The present invention further relates to a T cell population, engineered to express on the cell surface a CAR specific for at least one IL-23 receptor, wherein said CAR comprises:
(i) an extracellular binding domain, wherein said binding domain binds to said IL-23R,
(ii) optionally an extracellular hinge domain,
(iii) a transmembrane domain,
(iv) an intracellular signaling domain, and,
(v) optionally a tag and/or a leader sequence.

In one embodiment, said T cell population is a regulatory T cell population.

In one embodiment, said T cell population is a Treg cell population selected from the group comprising or consisting of $CD4^+CD25^+Foxp3^+$ Treg, Tr1 cells, TGF-β secreting Th3 cells, regulatory NKT cells, regulatory γδ T cells, regulatory $CD8^+$ T cells, and double negative regulatory T cells.

The present invention further relates to a composition comprising at least one T cell population engineered to express on the cell surface a CAR specific for at least one IL-23 receptor, wherein said CAR comprises:
(i) an extracellular binding domain, wherein said binding domain binds to said IL-23R,
(ii) optionally an extracellular hinge domain,
(iii) a transmembrane domain,
(iv) an intracellular signaling domain, and,
(v) optionally a tag and/or a leader sequence.

In one embodiment, said composition is a pharmaceutical composition and further comprises at least one pharmaceutically acceptable excipient.

The present invention further relates to an ex vivo method for obtaining a T cell population engineered to express on the cell surface a CAR specific for at least one IL-23 receptor, wherein said CAR comprises:
(i) an extracellular binding domain, wherein said binding domain binds to said at least one IL-23R,
(ii) optionally an extracellular hinge domain,
(iii) a transmembrane domain,
(iv) an intracellular signaling domain, and,
(v) optionally a tag and/or a leader sequence,
wherein said method comprises the genetic modification, preferably the transduction, of at least one T cell with a nucleic acid encoding an IL-23R-CAR, and optionally an expansion step of the transduced cells.

The present invention further relates to a method for treating an IL-23R expressing cell-mediated disease or disorder, comprising administering to a subject in need thereof at least one T cell population engineered to express on the cell surface a CAR specific for at least one IL-23 receptor, wherein said CAR comprises:
(i) an extracellular binding domain, wherein said binding domain binds to said at least one IL-23R,
(ii) optionally an extracellular hinge domain,
(iii) a transmembrane domain,
(iv) an intracellular signaling domain, and,
(v) optionally a tag and/or a leader sequence.

The present invention further relates to a T cell population as described herein or to a composition as described herein for treating, or for use in treating, an IL-23R expressing cell-mediated disease or disorder.

In one embodiment, said IL-23R expressing cell-mediated disease or disorder is an autoimmune and/or inflammatory disease or disorder.

In one embodiment, said IL-23R expressing cell-mediated disease or disorder is selected from the group comprising or consisting of inflammatory bowel diseases (such as, for example, Crohn's disease and ulcerative colitis), systemic lupus erythematosus, rheumatoid arthritis, juvenile idiopathic arthritis, Sjögren syndrome, systemic sclerosis, ankylosing spondylitis, Type 1 diabetes, autoimmune thyroid disorders, multiple sclerosis, Myasthenia Gravis, psoriasis, psoriatic arthritis or uveitis. In one embodiment, said IL-23R expressing cell-mediated disease is an autoimmune and/or inflammatory disease or disorder, preferably Crohn's disease.

Definitions

In the present invention, the following terms have the following meanings:
The terms "a" and "an" refer to one or to more than one (i.e., to at least one) of the grammatical object of the article. By way of example, "an element" means one element or more than one element.
The term "about" when referring to a measurable value such as an amount, a temporal duration, and the like, is meant to encompass variations of ±20% or in some instances ±10%, or in some instances ±5%, or in some instances ±1%, or in some instances ±0.1% from the specified value, as such variations are appropriate to perform the disclosed methods.
The term "activation" as used herein, refers to the state of a T cell (e.g., a regulatory T cell) that has been sufficiently stimulated to induce a detectable cellular response. Activation can also be associated with detectable effector function(s) such as cytokine production or suppressive activity. The term "activated" regulatory T cells refers to, among other things, regulatory T cells that are capable of suppressing an immune response.
The term "antibody", as used herein, refers to a protein, or polypeptide sequence derived from an immunoglobulin molecule which specifically binds with an antigen. Antibodies can be polyclonal or monoclonal, multiple or single chain, or intact immunoglobulins, and may be derived from natural sources or from recombinant sources. The term "antibody" also includes multispecific antibodies (e.g., bispecific antibodies), and antibody fragments, so long as they exhibit the desired biological activity. Antibodies can be multimers of immunoglobulin molecules, such as tetramers of immunoglobulin molecules. The basic four-chain antibody unit is a heterotetrameric glycoprotein composed of two identical light (L) chains and two identical heavy (H) chains. The L chain from any vertebrate species can be assigned to one of two clearly distinct types, called kappa ([kappa]) and lambda ([lambda]), based on the amino acid sequences of their constant domains (CL). Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ([alpha]), delta ([delta]), epsilon ([epsilon]), gamma ([gamma]) and mu ([mu]), respectively. The [gamma] and [alpha] classes are further divided into subclasses on the basis of relatively minor differences in CH sequence and function, e.g., humans express the following subclasses: IgG1, IgG2, IgG3, IgG4, IgA1, and IgA2. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain (VH) followed by three constant domains (CH) for each of the [alpha] and [gamma] chains and four CH domains for [mu] and [epsilon] isotypes. Each L chain has at the N-terminus, a variable domain (VL) followed by a constant domain (CL) at its other end. The VL is aligned with the VH and the CL is aligned with the first constant domain of the heavy chain (CH1). Particular amino acid residues are believed to form an interface between the light chain and heavy chain variable domains. The pairing of a VH and a VL together forms a single antigen-binding site. An IgM antibody consists of five of the basic heterotetramer units along with an additional polypeptide called a J chain, and therefore, contains ten antigen-binding sites, while secreted IgA antibodies can polymerize to form polyvalent assemblages comprising 2-5 of the basic 4-chain units along with J chain. In the case of IgGs, the 4-chain unit is generally about 150,000 Daltons. For the structure and properties of the different classes of antibodies, see, e.g., Basic and Clinical Immunology, 8th edition, Daniel P. Stites, Abba I. Terr and Tristram G. Parslow (eds.), Appleton & Lange, Norwalk, Conn., 1994, page 71, and Chapter 6.

The term "monoclonal antibody" as used herein refers to an antibody obtained from a population of substantially homogeneous antibodies, i.e., the individual antibodies comprised in the population are identical except for possible naturally occurring mutations that may be present in minor amounts. Monoclonal antibodies are highly specific, being directed against a single antigenic site. Furthermore, in contrast to polyclonal antibody preparations that include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" is not to be construed as requiring production of the antibody by any particular method. For example, a monoclonal antibody may be prepared by the hybridoma methodology first described by Kohler et al., Nature, 256:495 (1975), or may be made using recombinant DNA methods in bacterial, eukaryotic animal or plant cells (see, e.g., U.S. Pat. No. 4,816,567). A "monoclonal antibody" may also be isolated from phage antibody libraries using the techniques described in Clackson et al., Nature, 352:624-628 (1991) and Marks et al., J. Mol. Biol., 222:581-597 (1991), for example. The monoclonal antibodies herein include "chimeric" antibodies.

The term "antibody fragment" refers to at least one portion of an intact antibody, preferably the antigen binding region or variable region of the intact antibody, that retains the ability to specifically interact with (e.g., by binding, steric hindrance, stabilizing/destabilizing, spatial distribution) an epitope of an antigen. Examples of antibody fragments include, but are not limited to, Fab, Fab', F(ab')$_2$, Fv fragments, scFv antibody fragments, disulfide-linked Fvs (sdFv), a Fd fragment consisting of the VH and CH1 domains, linear antibodies, single domain antibodies such as sdAb (either VL or VH), camelid VHH domains, multi-specific antibodies formed from antibody fragments such as a bivalent fragment comprising two Fab fragments linked by a disulfide bridge at the hinge region, and an isolated CDR or other epitope binding fragments of an antibody. An antigen binding fragment can also be incorporated into single domain antibodies, maxibodies, minibodies, nanobodies, intrabodies, diabodies, triabodies, tetrabodies, a v-NAR and a bis-scFv (see, e.g., Hollinger and Hudson, Nature Biotechnology 23:1126-1136, 2005). Antigen binding fragments can also be grafted into scaffolds based on polypeptides such as a fibronectin type III (see U.S. Pat. No. 6,703,199, which describes fibronectin polypeptide minibodies). Papain digestion of antibodies produces two identical antigen-binding fragments, called "Fab" fragments, and a residual "Fc" fragment, a designation reflecting the ability to crystallize readily. The Fab fragment consists of an entire L chain along with the variable region domain of the H chain (VH), and the first constant domain of one heavy chain (CH1). Each Fab fragment is monovalent with respect to antigen binding, i.e., it has a single antigen-binding site. Pepsin treatment of an antibody yields a single large F(ab')$_2$ fragment that roughly corresponds to two disulfide linked Fab fragments having divalent antigen-binding activity and is still capable of crosslinking antigen. Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments that have hinge cysteines between them. Other chemical couplings of antibody fragments are also known.

The "Fc" fragment of an antibody comprises the carboxy-terminal portions of both H chains held together by disulfides. The effector functions of antibodies are determined by sequences in the Fc region, which region is also the part recognized by Fc receptors (FcR) found on certain types of cells.

"Fv" is the minimum antibody fragment that contains a complete antigen-recognition and -binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although at a lower affinity than the entire binding site.

The term "scFv" refers to a fusion protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein an scFv may have the VL and VH variable regions in either order, e.g., with respect to the N-terminal and C-terminal ends of the polypeptide, the scFv may comprise VL-linker-VH or may comprise VH-linker-VL.

An "intact" antibody is one which comprises an antigen-binding site as well as a CL and at least heavy chain constant domains, CH1, CH2 and CH3. The constant domains may be native sequence constant domains (e.g., human native sequence constant domains) or amino acid sequence variants thereof. A "native sequence" polynucleotide is one that has the same nucleotide sequence as a polynucleotide derived from nature. A "native sequence" polypeptide is one that has the same amino acid sequence as a polypeptide (e.g., antibody) derived from nature (e.g., from any species). Such native sequence polynucleotides and polypeptides can be isolated from nature or can be produced by recombinant or synthetic means.

The term "antibody heavy chain", refers to the larger of the two types of polypeptide chains present in antibody molecules in their naturally occurring conformations, and which normally determines the class to which the antibody belongs.

The term "antibody light chain", refers to the smaller of the two types of polypeptide chains present in antibody molecules in their naturally occurring conformations. Kappa (κ) and lambda (λ) light chains refer to the two major antibody light chain isotypes.

The term "antigen" or "Ag" refers to a molecule that provokes an immune response. This immune response may involve either antibody production, and/or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequence or a partial nucleotide sequence encoding a protein that elicits an immune response therefore encodes an "antigen" as that term is used herein. Furthermore, one skilled in the art will understand that an antigen does not necessarily need to be encoded solely by a full-length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen does not necessarily need to be encoded by a "gene" at all. It is readily apparent that an antigen can be synthesized or can be derived from a biological sample, or might be macromolecule besides a polypeptide. Such a biological sample can include, but is not limited to a tissue sample, a cell or a fluid with other biological components.

The term "adnectin", also known as monobody, is well known in the art and refers to proteins designed to bind with high affinity and specificity to antigens. They belong to the class of molecules collectively called "antibody mimetics".

The term "alphabody", as used herein, that may also be referred to as Cell-Penetrating Alphabodies, refers to a type of antibody mimetics consisting of small 10 kDa proteins engineered to bind to a variety of antigens. Alphabodies are able to reach and bind to intracellular protein targets.

The term "affibody" is well known in the art and refers to affinity proteins based on a 58 amino acid residue protein domain, derived from one of the IgG binding domain of staphylococcal protein A.

The term "affilin" is well known in the art and refers to artificial proteins designed to selectively bind antigens. They resemble antibodies in their affinity and specificity to antigens but not in structure which makes them a type of antibody mimetic.

The term "anticalin" is well known in the art and refers to an antibody mimetic technology, wherein the binding specificity is derived from lipocalins. Anticalins may also be formatted as dual targeting protein, called Duocalins.

The term "armadillo repeat protein-based scaffold", as used herein, refers to a type of antibody mimetics corresponding to artificial peptide binding scaffolds based on armadillo repeat proteins. Armadillo repeat proteins are characterized by an armadillo domain, composed of tandem armadillo repeats of approximately 42 amino acids, which mediates interactions with peptides or proteins.

The term "atrimer" is well known in the art and refers to binding molecules for target protein that trimerize as a perquisite for their biological activity. They are relatively large compared to other antibody mimetic scaffolds.

The term "avimer" is well known in the art and refers to an antibody mimetic technology The term "DARPins" (Designed Ankyrin Repeat Proteins) is well known in the art and refers to an antibody mimetic DRP (designed repeat protein) technology developed to exploit the binding abilities of non-antibody polypeptides.

The term "diabody" refers to small antibody fragments prepared by constructing scFv fragments with short linkers (about 5-10 residues) between the VH and VL domains such that inter-chain but not intra-chain pairing of the V domains is achieved, resulting in a bivalent fragment, i.e., fragment having two antigen binding sites. Bispecific diabodies are heterodimers of two "crossover" scFv fragments in which the VH and VL domains of the two antibodies are present on different polypeptide chains. Diabodies are described more fully in, for example, EP 0404097; WO 93/11161; and Holliger et al., Proc. Natl. Acad. Sci. USA, 90:6444-6448 (1993).

The term "evasins" is well known in the art and refers to a class of chemokine-binding proteins.

The term "fynomers" is well known in the art and refers to proteins that belong to the class of antibody mimetic. They are attractive binding molecules due to their high thermal stability and reduced immunogenicity.

The term "knottin" (that may also be referred to as inhibitor cystine not), as used herein, refers to an antibody mimetic comprising a protein structural motif containing three disulfide bridges.

The term "domain kunitz peptide" refers to a type of antibody mimetics, and is based on the active domains of proteins inhibiting the function of proteases.

The term "nanobody" is well known in the art and refers to an antibody-derived therapeutic protein that contains the unique structural and functional properties of naturally-occurring heavy chain antibodies. These heavy chain antibodies contain a single variable domain (VHH) and two constant domains (CH2 and CH3).

The term "unibody" is well known in the art and refers to an antibody fragment lacking the hinge region of IgG4 antibodies. The deletion of the hinge region results in a molecule that is essentially half the size of traditional IgG4 antibodies and has a univalent binding region rather than the bivalent biding region of IgG4 antibodies.

The term "versabodies" is well known in the art and refers to another antibody mimetic technology. They are small proteins of 3-5 kDa with >15% cysteines, which form a high disulfide density scaffold, replacing the hydrophobic core the typical proteins have.

The term "antigen presenting cell" or "APC" refers to an immune system cell such as an accessory cell (e.g., a B-cell, a dendritic cell, and the like) that displays a foreign antigen complexed with major histocompatibility complexes (MHC's) on its surface. T-cells may recognize these complexes using their T-cell receptors (TCRs). APCs process antigens and present them to T-cells.

The term "allogeneic" refers to any material derived from a different individual of the same specie as the individual to whom the material is introduced. Two or more individuals are said to be allogeneic to one another when the genes at one or more loci are not identical. In some aspects, allogeneic material from individuals of the same species may be sufficiently unlike genetically to interact antigenically.

The term "autologous" refers to any material derived from the same individual to whom it is later to be re-introduced.

The term "chimeric receptor or chimeric antigen receptor or CR or CAR" refers to one polypeptide or to a set of polypeptides, typically two in the simplest embodiments, which when in an immune cell, provides the cell with specificity for a target ligand and with intracellular signal generation. In some embodiments, the set of polypeptides are contiguous with each other. In some embodiments, the chimeric receptor is a chimeric fusion protein comprising the set of polypeptides. In some embodiments, the set of polypeptides include a dimerization switch that, upon the presence of a dimerization molecule, can couple the polypeptides to one another, e.g., can couple a ligand binding domain to an intracellular signaling domain. In one embodiment, the chimeric receptor comprises an optional leader sequence at the amino-terminus (N-ter) of the chimeric receptor fusion protein. In one embodiment, the chimeric receptor further comprises a leader sequence at the N-terminus of the extracellular ligand binding domain, wherein the leader sequence is optionally cleaved from the ligand binding domain during cellular processing and localization of the chimeric receptor to the cellular membrane.

The term "conservative sequence modifications" refers to amino acid modifications that do not significantly affect or alter the biologic function of the protein containing the amino acid sequence. Such conservative modifications include amino acid substitutions, additions and deletions. Modifications can be introduced into a protein by standard techniques known in the art, such as site-directed mutagenesis and PCR-mediated mutagenesis. Conservative amino acid substitutions are ones in which the amino acid residue is replaced with an amino acid residue that has similar properties, such that one skilled in the art of peptide chemistry would expect the secondary structure and hydropathic nature of the polypeptide to be substantially unchanged. Amino acid substitutions are generally therefore based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include: arginine and lysine; glutamate and aspartate; serine and threonine; glutamine and asparagine; and valine, leucine and isoleucine. Amino acid substitutions may further be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Other families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, one or more amino acid residues within a chimeric receptor of the invention can be replaced with other amino acid residues from the same side chain family and the altered chimeric receptor can be tested using the functional assays described herein.

The term "constitutive" promoter refers to a nucleotide sequence which, when operably linked with a polynucleotide which encodes or specifies a gene product, causes the gene product to be produced in a cell under most or all physiological conditions of the cell.

The term a "costimulatory molecule" refers to a cognate binding partner on a T cell that specifically binds with a costimulatory ligand, thereby mediating a costimulatory response by the T cell, such as, but not limited to, proliferation. Costimulatory molecules are cell surface molecules other than antigen receptors or their ligands that contribute to an efficient immune response. A costimulatory signaling domain can be the intracellular portion of a costimulatory molecule. A costimulatory molecule can be represented in the following protein families: TNF receptor proteins, Immunoglobulin-like proteins, cytokine receptors, integrins, signaling lymphocytic activation molecules (SLAM proteins), and activating NK cell receptors.

The term "derived from" as used herein, indicates a relationship between a first and a second molecule. It generally refers to structural similarity between the first molecule and a second molecule and does not connote or include a process or source limitation on a first molecule that is derived from a second molecule. For example, in the case of an intracellular signaling domain that is derived from a CD3 zeta molecule, the intracellular signaling domain retains sufficient CD3 zeta structure such that is has the required function, namely, the ability to generate a signal under the appropriate conditions. It does not connote or include a limitation to a particular process of producing the intracellular signaling domain, e.g., it does not mean that, to provide the intracellular signaling domain, one must start with a CD3 zeta sequence and delete unwanted sequence, or impose mutations, to arrive at the intracellular signaling domain.

The term "encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (e.g., rRNA, tRNA and mRNA) or a defined sequence of amino acids and the biological properties resulting therefrom. Thus, a gene, cDNA, or RNA, encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. The phrase "nucleotide sequence that encodes a protein or a RNA" may also include introns to the extent that the nucleotide sequence encoding the protein may in some version contain an intron(s).

The term "endogenous" refers to any material from or produced inside an organism, cell, tissue or system.

The term "engineered" or "modified" refers to a cell that has been transfected, transformed or transduced.

The term "exogenous" refers to any material introduced from or produced outside an organism, cell, tissue or system.

The term "expression" refers to the transcription and/or translation of a particular nucleotide sequence driven by a promoter.

The term "expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, including cosmids, plasmids (e.g., naked or contained in liposomes) and viruses (e.g., lentiviruses, retroviruses, adenoviruses, and adeno-associated viruses) that incorporate the recombinant polynucleotide.

The term "homology" or "identity" refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous or identical at that position. The homology between two sequences is a direct function of the number of matching or homologous positions; e.g., if half (e.g., five positions in a polymer of ten subunits in length) of the positions in two sequences are homologous, the two sequences are 50% homologous; if 90% of the positions (e.g., 9 of 10), are matched or homologous, the two sequences are 90% homologous. Thus, the term "homologous" or "identical", when used in a relationship between the sequences of two or more polypeptides or of two or more nucleic acid molecules, refers to the degree of sequence relatedness between polypeptides or nucleic acid molecules, as determined by the number of matches between strings of two or more amino acid or nucleotide residues. "Identity" measures the percent of identical matches between the smaller of two or more sequences with gap alignments (if any) addressed by a particular mathematical model or computer program (i.e., "algorithms"). Identity of related polypeptides can be readily calculated by known methods. Such methods include, but are not limited to, those described in Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; Sequence Analysis Primer, Gribskov, M. and Devereux, J., eds., M. Stockton Press, New York, 1991; and Carillo et al., SIAM J. Applied Math. 48, 1073 (1988). Preferred methods for determining identity are designed to give the largest match between the sequences tested. Methods of determining identity are described in publicly available computer programs. Preferred computer program methods for determining identity between two sequences include the GCG program package, including GAP (Devereux et al., Nucl. Acid. Res. \2, 387 (1984); Genetics Computer Group, University of Wisconsin, Madison, Wis.), BLASTP, BLASTN, and FASTA (Altschul et al., J. Mol. Biol. 215, 403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra). The well-known Smith Waterman algorithm may also be used to determine identity.

The terms "humanized" forms of non-human (e.g., murine) antibodies refer to chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies and antibody fragments thereof are human immunoglobulins (recipient antibody or antibody fragment) in which residues from a complementary-determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, a humanized antibody/antibody fragment can comprise residues which are found neither in the recipient antibody nor in the imported CDR or framework sequences. These modifications can further refine and optimize antibody or antibody fragment performance. In general, the humanized antibody or antibody fragment thereof will comprise substantially all of at least one, and typically two, variable domains, in which all or substantially all of the CDR regions correspond to those of a non-human immunoglobulin and all or a significant portion of the FR regions are those of a human immunoglobulin sequence. The humanized antibody or antibody fragment can also comprise at least a portion of an immunoglobulin constant region (Fc), typically that of a human immunoglobulin. For further details, see Jones et al., Nature, 321: 522-525, 1986; Reichmann et al., Nature, 332: 323-329, 1988; Presta, Curr. Op. Struct. Biol., 2: 593-596, 1992.

As used herein, "in vitro transcribed RNA" refers to RNA, preferably mRNA, that has been synthesized in vitro. Generally, the in vitro transcribed RNA is generated from an in vitro transcription vector. The in vitro transcription vector comprises a template that is used to generate the in vitro transcribed RNA.

The term "inducible" promoter refers to a nucleotide sequence which, when operably linked with a polynucleotide which encodes or specifies a gene product, causes the gene product to be produced in a cell substantially only when an inducer which corresponds to the promoter is present in the cell.

As used herein, a "5' cap" (also termed an RNA cap, an RNA 7-methylguanosine cap or an RNA m7G cap) is a modified guanine nucleotide that has been added to the "front" or 5' end of a eukaryotic messenger RNA shortly after the start of transcription. The 5' cap thus consists of a terminal group which is linked to the first transcribed nucleotide. Its presence is critical for recognition by the ribosome and protection from RNases. Cap addition is coupled to transcription, and occurs co-transcriptionally, such that each influences the other. Shortly after the start of transcription, the 5' end of the mRNA being synthesized is bound by a cap-synthesizing complex associated with RNA polymerase. This enzymatic complex catalyzes the chemical reactions that are required for mRNA capping. Synthesis proceeds as a multi-step biochemical reaction. The capping moiety can be modified to modulate functionality of mRNA such as its stability or efficiency of translation.

In the context of the present invention, the following abbreviations for the commonly occurring nucleic acid bases are used. "A" refers to adenine, "C" refers to cytosine, "G" refers to guanine, "T" refers to thymine, and "U" refers to uracil.

The term "instructional material" includes a publication, a recording, a diagram, or any other medium of expression which can be used to communicate the usefulness of the compositions and methods of the invention. The instructional material of the kit of the invention may, for example, be affixed to a container which contains the cell of the invention or be shipped together with a container which contains the cell of the invention. Alternatively, the instructional material may be shipped separately from the container with the intention that the instructional material cell be used cooperatively by the recipient.

The term "intracellular signaling domain" as used herein, refers to an intracellular portion of a molecule. The intracellular signaling domain generates a signal that promotes an immune effector function of the chimeric receptor containing cell. Examples of immune effector function in a chimeric receptor-T cell may include cytolytic activity, suppressive activity, regulatory activity and helper activity, including the secretion of cytokines.

The term "isolated" means altered or removed from the natural state. For example, a nucleic acid or a peptide naturally present in a living animal is not "isolated", but the same nucleic acid or peptide partially or completely separated from the coexisting materials of its natural state is "isolated". An isolated nucleic acid or peptide can exist in substantially purified form, or can exist in a non-native environment such as, for example, a host cell. Typically, a preparation of isolated nucleic acid or peptide contains the nucleic acid or peptide at least about 80% pure, at least about 85% pure, at least about 90% pure, at least about 95% pure, greater than 95% pure, greater than about 96% pure, greater than about 97% pure, greater than about 98% pure, or greater than about 99% pure. An "isolated nucleic acid" is a nucleic acid that is substantially separated from other genome DNA sequences as well as proteins or complexes such as ribosomes and polymerases, which naturally accompany a native sequence. The term embraces a nucleic acid sequence that has been removed from its naturally occurring environment, and includes recombinant or cloned DNA isolates and chemically synthesized analogues or analogues biologically synthesized by heterologous systems. An "isolated polypeptide" is one that has been identified and separated and/or recovered from a component of its natural environment.

The term "lentivirus" refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses.

The term "lentiviral vector" refers to a vector derived from at least a portion of a lentivirus genome, including especially a self-inactivating lentiviral vector as provided in Milone et al., Mol. Ther. 17(8): 1453-1464 (2009). Other examples of lentivirus vectors that may be used in the clinic, include but are not limited to, the LENTIVECTOR® gene delivery technology from Oxford BioMedica, the LENTIMAX™ vector system from Lentigen and the like. Nonclinical types of lentiviral vectors are also available and would be known to one skilled in the art.

The term "ligand" refers to a member of a pair ligand/receptor, and binds to the other member of the pair.

The term "nucleic acid" or "polynucleotide" refers to a polymer of nucleotides covalently linked by phosphodiester bonds, such as deoxyribonucleic acids (DNA) or ribonucleic acids (RNA), in either single- or double-stranded form. Unless specifically limited, the term encompasses nucleic acids containing known analogues of natural nucleotides that have similar binding properties as the reference nucleic acid and are metabolized in a manner similar to naturally occurring nucleotides. Unless otherwise indicated, a particular nucleic acid sequence also implicitly encompasses conservatively modified variants thereof (e.g., degenerate codon substitutions), alleles, orthologs, SNPs, and complementary sequences as well as the sequence explicitly indicated. Specifically, degenerate codon substitutions may be achieved by generating sequences in which the third position of one or more selected (or all) codons is substituted with mixed-base and/or deoxyinosine residues (Batzer et al., Nucleic Acid Res. 19:5081 (1991); Ohtsuka et al., J. Biol. Chem. 260:2605-2608 (1985); and Rossolini et al., Mol. Cell. Probes 8:91-98 (1994)).

The term "operatively linked" or "transcriptional control" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Operably linked DNA sequences can be contiguous with each other and, e.g., where necessary to join two protein coding regions, are in the same reading frame.

The terms "peptide", "polypeptide", and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. A polypeptide includes a natural peptide, a recombinant peptide, or a combination thereof.

The term "pharmaceutically acceptable excipient" or "pharmaceutically acceptable carrier" refers to an excipient that does not produce an adverse, allergic or other untoward reaction when administered to an animal, preferably a human. It includes any and all solvents, dispersion media, coatings, antibacterial and antifungal agents, isotonic and absorption delaying agents and the like. For human administration, preparations should meet sterility, pyrogenicity, general safety and purity standards as required by regulatory offices, such as, for example, FDA Office or EMA.

The term "poly(A)" refers to a series of adenosines monophosphate attached to the mRNA. In one embodiment of a construct for transient expression, the polyA is between 50 and 5000 adenosines monophosphate, preferably greater than or equal to 64, more preferably greater than or equal to 100, most preferably greater than or equal to 300 or 400 adenosines monophosphate. Poly(A) sequences can be modified chemically or enzymatically to modulate mRNA functionality such as localization, stability or efficiency of translation.

The term "polyadenylation" refers to the covalent linkage of a polyadenylyl moiety, or its modified variant, to a messenger RNA molecule. In eukaryotic organisms, most messenger RNA (mRNA) molecules are polyadenylated at the 3' end. The 3' poly (A) tail is a long sequence of adenine nucleotides (often several hundred) added to the pre-mRNA through the action of an enzyme, polyadenylate polymerase. In higher eukaryotes, the poly(A) tail is added onto transcripts that contain a specific sequence, the polyadenylation signal. The poly(A) tail and the protein bound to it aid in protecting mRNA from degradation by exonucleases. Polyadenylation is also important for transcription termination, export of the mRNA from the nucleus, and translation. Polyadenylation occurs in the nucleus immediately after transcription of DNA into RNA, but additionally can also occur later in the cytoplasm. After transcription has been terminated, the mRNA chain is cleaved through the action of an endonuclease complex associated with RNA polymerase. The cleavage site is usually characterized by the presence of the base sequence AAUAAA near the cleavage site. After the mRNA has been cleaved, adenosine residues are added to the free 3' end at the cleavage site.

The term "promoter" refers to a DNA sequence recognized by the synthetic machinery of the cell, or introduced synthetic machinery, required to initiate the specific transcription of a polynucleotide sequence.

The term "promoter/regulatory sequence" refers to a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

The term "recombinant protein or peptide" refers to a protein or peptide (e.g., an antibody) which is generated using recombinant DNA technology, such as, for example, a protein or peptide (e.g., an antibody) expressed by a bacteriophage or yeast expression system. The term should also be construed to mean a protein or peptide (e.g., an antibody) which has been generated by the synthesis of a DNA molecule encoding the protein or peptide (e.g., the antibody) and which DNA molecule expresses a protein or peptide (e.g., an antibody), or an amino acid sequence specifying the protein or peptide (e.g., the antibody), wherein the DNA or amino acid sequence has been obtained using recombinant DNA or amino acid sequence technology which is available and well known in the art.

The term "signaling domain" refers to the functional portion of a protein which acts by transmitting information within the cell to regulate cellular activity via defined signaling pathways by generating second messengers or functioning as effectors by responding to such messengers.

The term "signal transduction pathway" refers to the biochemical relationship between a variety of signal transduction molecules that play a role in the transmission of a signal from one portion of a cell to another portion of a cell.

The term "specifically binds" refers to an antibody, or a ligand, which recognizes and binds with a binding partner present in a sample, but which antibody or ligand does not substantially recognize or bind other molecules in the sample.

The term "stimulation" refers to a primary response induced by binding of a stimulatory molecule (e.g., a TCR/CD3 complex or chimeric receptor) with its cognate ligand thereby mediating a signal transduction event, such as, but not limited to, signal transduction via the TCR/CD3 complex or signal transduction via signaling domains of the chimeric receptor. Stimulation can mediate altered expression of certain molecules.

The term "stimulatory molecule" refers to a molecule expressed by an immune cell (e.g., T cell, NK cell, B cell) that provides the cytoplasmic signaling sequence(s) that regulate activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as immunoreceptor tyrosine-based activation motif or ITAM.

The term "subject" is intended to include living organisms in which an immune response can be elicited (e.g., mammals, human). In one embodiment, a subject may be a "patient", i.e., a warm-blooded animal, more preferably a human, who/which is awaiting the receipt of, or is receiving medical care or was/is/will be the object of a medical procedure, or is monitored for the development of the targeted disease or condition, such as, for example, an inflammatory or autoimmune condition. In one embodiment, the subject is an adult (for example a subject above the age of 18). In another embodiment, the subject is a child (for example a subject below the age of 18). In one embodiment, the subject is a male. In another embodiment, the subject is a female. In one embodiment, the subject is affected, preferably is diagnosed, with an autoimmune and/or inflammatory disease or disorder, such as, for example an autoantibody-mediated autoimmune disease. In one embodiment, the subject is at risk of developing an autoimmune and/or inflammatory disease or disorder, such as, for example an autoantibody-mediated autoimmune disease. Examples of risks factor include, but are not limited to, genetic predisposition, or familial history of an autoimmune and/or inflammatory disease or disorder.

The term "substantially purified cell" refers to a cell that is essentially free of other cell types. A substantially purified cell also refers to a cell which has been separated from other cell types with which it is normally associated in its naturally occurring state. In one embodiment, a substantially purified cell refers to a cell which is at least about 75% free, 80% free, or 85% free, and preferably about 90%, 95%, 96%, 97%, 98%, or 99% free, from other cell types with which it is normally associated in its naturally occurring state. In some instances, a population of substantially purified cells refers to a homogenous population of cells. In one embodiment, a population of substantially purified cells refers to a population of cells at least about 750% homogenous, 80% homogenous, or 85% homogenous, and preferably about 90%, 95%, 96%, 97%, 98%, or 99% homogenous. In other instances, this term refers simply to cells that have been separated from the cells with which they are naturally associated in their natural state. In some aspects, the cells are cultured in vitro. In other aspects, the cells are not cultured in vitro.

The terms "therapeutically effective amount" refer to an amount of cells expressing a CAR as described herein, effective to achieve a particular biological result. Thus, the terms "therapeutically effective amount" mean a level or amount of agent that is aimed at, without causing significant negative or adverse side effects to the target, (1) delaying or preventing the onset of the targeted disease or condition; (2) slowing down or stopping the progression, aggravation, or deterioration of one or more symptoms of the targeted disease or condition; (3) bringing about ameliorations of the symptoms of the targeted disease or condition; (4) reducing the severity or incidence of the targeted disease or condition; or (5) curing the targeted disease or condition. A therapeutically effective amount may be administered prior to the onset of the targeted disease or condition, for a prophylactic or preventive action. Alternatively, or additionally, the therapeutically effective amount may be administered after initiation of the targeted disease or condition, for a therapeutic action.

The term "transfected" or "transformed" or "transduced" refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The term "transfer vector" refers to a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "transfer vector" includes an autonomously replicating plasmid or a virus. The term should also be construed to further include non-plasmid and non-viral compounds which facilitate transfer of nucleic acid into cells, such as, for example, a poly lysine compound, liposome, and the like. Examples of viral transfer vectors include, but are not limited to, adenoviral vectors, adeno-associated virus vectors, retroviral vectors, lentiviral vectors, and the like.

As used herein, "transient" refers to expression of a non-integrated transgene for a period of hours, days or weeks, wherein the period of time of expression is less than the period of time for expression of the gene if integrated into the genome or contained within a stable plasmid replicon in the host cell.

As used herein, the terms "treat", "treatment" and "treating" refer to the reduction or amelioration of the progression, severity and/or duration of a targeted disease or condition, e.g., an autoimmune condition, or the amelioration of one or more symptoms (preferably, one or more discernible symptoms) of a targeted disease or condition, e.g., an autoimmune condition, wherein said amelioration results from the administration of one or more therapies (e.g., one or more therapeutic agents such as a Treg cell of the invention). In specific embodiments, the terms "treat", "treatment" and "treating" refer to the amelioration of at least one measurable physical parameter of a targeted disease or condition, e.g., an autoimmune and/or inflammatory disease or disorder. In other embodiments, the terms "treat", "treatment" and "treating" refer to the inhibition of the progression of a targeted disease or condition, e.g., an autoimmune and/or inflammatory disease or disorder, either physically by, e.g., stabilization of a discernible symptom, physiologically by, e.g., stabilization of a physical parameter, or both. In other embodiments, the terms "treat", "treatment" and "treating" refer to the reduction or amelioration of the progression, severity and/or duration of a targeted disease or condition, e.g., an autoimmune and/or inflammatory disease or disorder, or the amelioration of one or more symptoms of a targeted disease or condition, e.g., an autoimmune and/or inflammatory disease or disorder. "Treating" or "treatment" refers to both therapeutic treatment and prophylactic or preventative measures; wherein the object is to prevent or slow down (lessen) the targeted disease or condition. Those in need of treatment include those already with the condition as well as those prone to have the condition or those in whom the condition is to be prevented. A subject is successfully "treated" for a disease or condition if, after receiving a therapeutic amount of a population of cells comprising a chimeric receptor according to the present invention, the subject shows observable and/or measurable improvement in one or more of the following: reduction in the number of pathogenic cells; reduction in the percent of total cells that are pathogenic; relief to some extent of one or more of the symptoms associated with the specific condition; reduced morbidity and mortality, and/or improvement in quality of life issues. The above parameters for assessing successful treatment and improvement in the condition are readily measurable by routine procedures familiar to a physician.

The term "Treg cell" refers to a cell capable of suppressing, inhibiting or preventing excessive or unwanted inflammatory responses, such as, for example, autoimmunity or allergic reactions. In one embodiment, the Treg cell population of the invention is capable of suppressive activity. In one embodiment, said suppressive activity is contact independent. In another embodiment, said suppressive activity is contact dependent. In one embodiment, the Treg cell population of the invention presents a suppressive action on effector T cells, preferably said suppressive action is dependent on TCR expression and/or activation.

The term polynucleotide "variant" as used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences of the invention and evaluating one or more biological activities of the encoded polypeptide as described herein and/or using any of a number of techniques well known in the art. Accordingly, the term "polypeptide variant" as used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences and evaluating one or more biological activities of the polypeptide as described herein and/or using any of a number of techniques well known in the art. Modifications may be made in the structure of the polynucleotides and polypeptides of the present invention and still obtain a functional molecule that encodes a variant or derivative polypeptide with desirable characteristics. When it is desired to alter the amino acid sequence of a polypeptide to create an equivalent, or even an improved, variant or portion of a polypeptide of the invention, one skilled in the art will typically change one or more of the codons of the encoding DNA sequence. For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with similar properties. It is thus contemplated that various changes may be made in the peptide sequences of the present invention, or corresponding DNA sequences that encode said peptides without appreciable loss of their biological utility or activity. In many instances, a polypeptide variant will contain one or more conservative substitutions. A variant may also, or alternatively, contain non-conservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide.

The term "zeta" or alternatively "zeta chain", "CD3-zeta" or "TCR-zeta" is defined as the protein provided as GenBank Acc. No. BAG36664.1, or the equivalent residues from a non-human species, e.g., mouse, rodent, monkey, ape and the like, and a "zeta stimulatory domain" or alternatively a "CD3-zeta stimulatory domain" or a "TCR-zeta stimulatory domain" is defined as the amino acid residues from the cytoplasmic domain of the zeta chain, or functional derivatives thereof, that are sufficient to functionally transmit an initial signal necessary for T cell activation. In one embodiment, the cytoplasmic domain of zeta comprises residues 52 through 164 of GenBank Acc. No. BAG36664.1 or the equivalent residues from a non-human species, e.g., mouse, rodent, monkey, ape and the like, that are functional orthologs thereof.

DETAILED DESCRIPTION

A first object of the present invention is a chimeric antigen receptor (CAR) specific for at least one IL-23 receptor (IL-23R), wherein said CAR comprises (i) an extracellular binding domain, wherein said binding domain binds to said IL-23R (that may be referred as an extracellular IL-23R binding domain), (ii) optionally an extracellular hinge domain, (iii) optionally a transmembrane domain, (iv) an intracellular signaling domain, and (v) optionally a tag and/or a leader sequence.

In one embodiment, the CAR comprises one or more polypeptides.

In one embodiment, the CAR of the invention recognizes and is capable to bind to an IL-23R expressed on the cell surface.

In another embodiment, the CAR of the invention recognizes and is capable to bind to a soluble IL-23R (i.e., not membrane bound).

In one embodiment, the CAR of the invention recognizes and binds to a human IL-23R. Human IL-23R is a protein encoded by a 2.8 kb long mRNA comprising 11 exons (Genbank accession number: NM_144701).

In one embodiment, the CAR of the invention recognizes and is capable to bind to an IL-23R variant, preferably a variant of a human IL-23R.

In one embodiment, a variant peptide of IL-23R refer to a modified IL-23R peptide wherein 1, 2, 3, 4, 5, 6, 7, 8, 9 or 10 amino acids are deleted, added or substituted as compared to the original peptide.

Splice variants of the human IL-23R have been previously identified (Kan et al, 2008). In particular, 24 different isoforms of IL-23R were described: isoform_v1 (encoded by a mRNA having the Genbank accession number AM990313), isoform_v2 (encoded by a mRNA having the Genbank accession number AM990314), isoform_v3 (encoded by a mRNA having the Genbank accession number AM990315), isoform_v4 (encoded by a mRNA having the Genbank accession number AM990316), isoform_v5 (encoded by a mRNA having the Genbank accession number AM990317), isoform_v6 (encoded by a mRNA having the Genbank accession number AM990318), isoform_v7 (encoded by a mRNA having the Genbank accession number AM990319), isoform_v8 (encoded by a mRNA having the Genbank accession number AM990320), isoform_v9 (encoded by a mRNA having the Genbank accession number AM990321), isoform_v10 (encoded by a mRNA having the Genbank accession number AM990322), isoform_v11 (encoded by a mRNA having the Genbank accession number AM990323), isoform_v12 (encoded by a mRNA having the Genbank accession number AM990324), isoform_v13 (encoded by a mRNA having the Genbank accession number AM990325), isoform_v14 (encoded by a mRNA having the Genbank accession number AM990326), isoform_v15 (encoded by a mRNA having the Genbank accession number AM990327), isoform_v16 (encoded by a mRNA having the Genbank accession number AM990328), isoform_v17 (encoded by a mRNA having the Genbank accession number AM990329), isoform_v18 (encoded by a mRNA having the Genbank accession number AM990330), isoform_v19 (encoded by a mRNA having the Genbank accession number AM990331), isoform_v20 (encoded by a mRNA having the Genbank accession number AM990332), isoform_v21 (encoded by a mRNA having the Genbank accession number AM990333), isoform_v22 (encoded by a mRNA having the Genbank accession number AM990334), isoform_v23 (encoded by a mRNA having the Genbank accession number AM990335) and isoform_v24 (encoded by a mRNA having the Genbank accession number AM990336).

Therefore, in one embodiment, the CAR of the invention recognizes and is capable to bind to a splice variant of the human IL-23R selected from the group comprising isoform_v1, isoform_v2, isoform_v3, isoform_v4, isoform_v5, isoform_v6, isoform_v7, isoform_v8, isoform_v9, isoform_v10, isoform_v11, isoform_v12, isoform_v13, isoform_v14, isoform_v15, isoform_v16, isoform_v17, isoform_v18, isoform_v19, isoform_v20, isoform_v21, isoform_v22, isoform_v23 and isoform_v24.

Moreover, single nucleotide polymorphisms in the alpha subunit of human IL-23R have been previously described (Kan et al., 2008 and Sivanesan et al. 2016).

In one embodiment, the CAR of the invention recognizes and is capable to bind to an IL-23R variant comprising a single nucleotide polymorphism (SNP) in the alpha subunit, wherein said SNP is selected from the group comprising R381Q, G149R, V362I and combinations thereof.

In one embodiment, the CAR of the invention recognizes and is capable to bind to a murine IL-23R.

In one embodiment, the extracellular IL-23R binding domain is an antibody directed to an IL-23R or an antigen binding fragment thereof.

The portion of the CAR of the invention comprising an antibody or antigen binding fragment thereof may exist in a variety of forms where the antigen binding domain is expressed as part of a contiguous polypeptide chain including, for example, a single chain antibody (scFv), a single domain antibody fragment (sdAb), a humanized antibody or bispecific antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, New York; Houston et al., 1988, Proc. Natl. Acad. Sci. USA 85:5879-5883; Bird et al., 1988, Science 242:423-426).

In one embodiment, the CAR of the invention comprises a whole antibody, a single chain antibody, a dimeric single chain antibody, a Fv, a scFv, a Fab, a F(ab)'$_2$, a defucosylated antibody, a bi-specific antibody, a diabody, a triabody, a tetrabody, a unibody, a domain antibody, a nanobody, or a antigen-binding fragment thereof.

In one embodiment, the extracellular IL-23R binding domain is an antibody mimetic. Examples of antibody mimetics include, but are not limited to, an affibody, an alphabody, an armadillo repeat protein based scaffold, a knottin, a kunitz domain peptide, an affilin, an affitin, an adnectin, an atrimer, an evasin, a DARPin, an anticalin, an avimer, a fynomer, a versabody or a duocalin.

In one embodiment, the extracellular binding domain of the CAR of the invention comprises or consists in an antibody fragment, such as, for example, a scFv.

The precise amino acid sequence boundaries of a given CDR can be determined using any of a number of well-known schemes, including those described by Kabat et al. (1991), "Sequences of Proteins of Immunological Interest" 5th Ed. Public Health Service, National Institutes of Health, Bethesda, MD ("Kabat" numbering scheme), Al-Lazikani et al., (1997) JMB 273, 927-948 ("Chothia" numbering scheme), or a combination thereof.

In one embodiment, the antibody comprised in the CAR of the invention is a multispecific antibody molecule, e.g., it comprises a plurality of immunoglobulin variable domain sequences, wherein a first immunoglobulin variable domain sequence of the plurality has binding specificity for a first epitope and a second immunoglobulin variable domain sequence of the plurality has binding specificity for a second epitope. In one embodiment, a multispecific antibody molecule is a bispecific antibody molecule. A bispecific antibody has specificity for no more than two antigens. A bispecific antibody molecule is characterized by a first immunoglobulin variable domain sequence which has binding specificity for a first epitope and a second immunoglobulin variable domain sequence that has binding specificity for a second epitope.

In one embodiment, the CAR comprises or consists of a scFv comprising a heavy chain VH having a sequence SEQ ID NO: 37, or a sequence having at least about 70%, preferably at least about 75%, 80%, 850%, 90%, 95% or more identity with SEQ ID NO: 37.

In one embodiment, the CAR comprises or consists of a scFv comprising a light chain VL selected from the group comprising SEQ ID NO: 38, 46 and 56 or sequences having at least about 70%, preferably at least about 75%, 80%, 85%, 90%, 95% or more identity with said SEQ ID NO: 38, 46 and 56, preferably comprises a light chain VL having the sequence SEQ ID NO: 38 or a sequence having at least about 70%, preferably at least about 75%, 80%, 85° %, 90%, 95% or more identity with said SEQ ID NO: 38.

In one embodiment, the scFv comprises a heavy chain VH having a SEQ ID NO: 37 (or a sequence having at least about 70%, preferably at least about 75%, 80%, 85%, 90%, 95% or more identity with said SEQ ID NO: 37) and a light chain VL selected from the group comprising SEQ ID NO: 38, 46, 56 and sequences having at least about 70%, preferably at least about 75%, 800%, 85%, 90%, 95% or more identity with said SEQ ID NO: 38, 46 and 56, preferably a VL having a SEQ ID NO: 38 (or a sequence having at least about 70%, preferably at least about 75%, 80%, 85%, 90%, 95% or more identity with said SEQ ID NO: 38).

In one embodiment, the scFv comprises a heavy chain VH having a SEQ ID NO: 37 (or a sequence having at least about 70%, preferably at least about 75%, 80%, 85%, 90%, 95% or more identity with said SEQ ID NO: 37) and a light chain VL having a SEQ ID NO: 38 (or a sequence having at least about 70%, preferably at least about 75%, 80%, 85° %, 90%, 95% or more identity with said SEQ ID NO: 38).

In one embodiment, the scFv comprises a heavy chain VH having a SEQ ID NO: 37 (or a sequence having at least about 70%, preferably at least about 75%, 80%, 85%, 90%, 95% or more identity with said SEQ ID NO: 37) and a light chain VL having a SEQ ID NO: 46 (or a sequence having at least about 70%, preferably at least about 75%, 80%, 85%, 90%, 95% or more identity with said SEQ ID NO: 46).

In one embodiment, the scFv comprises a heavy chain VH having a SEQ ID NO: 37 (or a sequence having at least about 70%, preferably at least about 75%, 80%, 85%, 90%, 95% or more identity with said SEQ ID NO: 37) and a light chain VL having a SEQ ID NO: 56 (or a sequence having at least about 70%, preferably at least about 75%, 80%, 85%, 90%, 95% or more identity with said SEQ ID NO: 56).

In one embodiment, the scFv comprises a linker that links the VH and the VL chains.

In one embodiment, the linker is a short oligo- or polypeptide, preferably having a length ranging from 2 to 10 amino acids.

For example, a glycine-serine doublet provides a particularly suitable hinge domain (GS linker). In one embodiment, the hinge domain is a Gly/Ser linker. Examples of Gly/Ser linkers include, but are not limited to, GS linkers, $G_2S$ linkers, $G_3S$ linkers, $G_4S$ linkers.

A non-limiting example of $G_2S$ linker is GGS.

$G_3S$ linkers comprise the amino acid sequence (Gly-Gly-Gly-Ser)$_n$, also referred to as (GGGS), or (SEQ ID NO: 1)$_n$, where n is a positive integer equal to or greater than 1 (such as, example, n=1, n=2, n=3, n=4, n=5, n=6, n=7, n=8, n=9 or n=10). Examples of $G_3S$ linkers include, but are not limited to, GGGSGGGSGGGSGGGS (SEQ ID NO: 6).

Examples of $G_4S$ linkers include, but are not limited to, (Gly$_4$ Ser) corresponding to GGGGS (SEQ ID NO: 5); (Gly$_4$ Ser)$_2$ corresponding to GGGGSGGGGS (SEQ ID NO: 4); (Gly$_4$Ser)$_3$ corresponding to GGGGSGGGGSGGGGS (SEQ ID NO: 3); and (Gly$_4$ Ser)$_4$ corresponding to GGGGSGGGGSGGGGSGGGGS (SEQ ID NO: 2).

In one embodiment, the linker is a $(G_4S)_3$ linker (SEQ ID NO: 3).

In one embodiment, the scFv comprises or consists in a sequence SEQ ID NO: 55, SEQ ID NO: 36 or SEQ ID NO: 57 or a sequence having at least about 70%, preferably at least about 75%, 80%, 85%, 90%, 95% or more identity with said SEQ ID NO: 55, SEQ ID NO: 36 or SEQ ID NO: 57. In one embodiment, the scFv comprises or consists in a sequence SEQ ID NO: 55 or a sequence having at least about 70%, preferably at least about 75%, 80%, 85%, 90%, 95% or more identity with said SEQ ID NO: 55.

In one embodiment, the CAR of the invention comprises an extracellular IL-23R binding domain and at least one other extracellular antigen binding domain. Therefore, according to this embodiment, the CAR of the invention is capable of binding IL-23R and at least one other antigen.

In one embodiment, the CAR of the invention is capable of binding an IL-23R, and a distinct antigen or ligand. In another embodiment, the CAR of the invention is capable of binding a first epitope on an IL-23R, and a distinct epitope on the same IL-23R. In another embodiment, the CAR of the invention is capable of binding an IL-23R, and a distinct IL-23R (such as, for example, a variant of IL-23R).

In one embodiment, said at least one other extracellular antigen binding domain is an antibody directed to a specific antigen or an antigen binding fragment thereof.

In one embodiment, said at least one other extracellular antigen binding domain comprises or consists in an antibody fragment, such as, for example, a scFv.

In one embodiment, said at least one other extracellular antigen binding domain (preferably scFv) is capable of binding to a food antigen from the common human diet.

The term "food antigen from common human diet" refers to an immunogenic peptide, which comes from foodstuffs common for humans, such as food antigens of the following non-limiting list: bovine antigens such as lipocalin, Ca-binding S100, alpha-lactalbumin, lactoglobulins such as beta-lactoglobulin, bovine serum albumin, caseins. Food-antigens may also be atlantic salmon antigens such as parvalbumin; chicken antigens such as ovomucoid, ovalbumin, Ag22, conalbumin, lysozyme or chicken serum albumin; peanut antigens; shrimp antigens such as tropomyosin; wheat antigens such as agglutinin or gliadin; celery antigens such as celery profilin; carrot antigens such as carrot profilin; apple antigens such as thaumatin, apple lipid transfer protein, or apple profilin; pear antigens such as pear profilin, or isoflavone reductase; avocado antigens such as endochitinase; apricot antigens such as apricot lipid transfer protein; peach antigens such as peach lipid transfer protein or peach profilin; soybean antigens such as HPS, soybean profilin or (SAM22) PR-I0 prot; fragments, variants and mixtures thereof.

In another embodiment, said at least one other extracellular antigen binding domain (preferably scFv) is capable of binding to an autoantigen, such as, for example, a multiple sclerosis-associated antigen, a joint-associated antigen, an eye-associated antigen, a human HSP antigen, a skin-associated antigen or an antigen involved in graft rejection or GVHD.

In one embodiment, the term "multiple sclerosis-associated antigen" refers to myelin basic protein (MBP). myelin associated glycoprotein (MAG), myelin oligodendrocyte glycoprotein (MOG), proteolipid protein (PLP), oligodendrocyte myelin oligoprotein (OMGP), myelin associated oligodendrocyte basic protein (MOBP), oligodendrocyte specific protein (OSP/Claudinl 1), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase), fragments, variants and mixtures thereof.

In one embodiment, the term "joint-associated antigen" refers to citrulline-substituted cyclic and linear filaggrin peptides, type II collagen peptides, human cartilage glycoprotein 39 (HCgp39) peptides, HSP, heterogeneous nuclear ribonucleoprotein (hnRNP) A2 peptides, hnRNP B1, hnRNP D, Ro60/52, HSP60, HSP65, HSP70 and HSP90, BiP, keratin, vimentin, fibrinogen, type I, III, IV and V collagen peptides, annexin V, Glucose 6 phosphate isomerase (GPI), acetyl-calpastatin, pyruvate dehydrogenase (PDH), aldolase, topoisomerase I, snRNP, PARP, Scl-70, Scl-100, phospholipid antigens including anionic cardiolipin and phosphatidylserine, neutrally charged phosphatidylethanolamine and phosphatidylcholine, matrix metalloproteinase, fibrillin, aggreccan, fragments, variants and mixtures thereof. Other examples of joint-associated antigens include, but are not limited to, citrullinated vimentin, citrullinated type II collagen, citrullinated fibrinogen.

In one embodiment, the term "eye-associated antigen" refers to type II collagen, retinal arrestin, S-arrestin, interphotoreceptor retinoid-binding proteins (IRBP1), beta-crystallin B1, retinal proteins, choroid proteins and fragments, variants and mixtures thereof. Other examples of eye-associated antigens include, but are not limited to, citrullinated vimentin, citrullinated type II collagen, citrullinated fibrinogen.

In one embodiment, the term "human HSP antigen" refers to human HSP60, HSP70, HSP90, fragments, variants and mixtures thereof.

In one embodiment, the antigen is an inflammatory nervous system condition-associated antigen, preferably a multiple sclerosis-associated antigen. Examples of inflammatory nervous system condition-associated antigens, preferably of multiple sclerosis-associated antigens include, but are not limited to myelin basic protein (MBP), myelin associated glycoprotein (MAG), myelin oligodendrocyte protein (MOG), proteolipid protein (PLP), oligodendrocyte myelin oligoprotein (OMGP), myelin associated oligodendrocyte basic protein (MOBP), oligodendrocyte specific protein (OSP/Claudinl 1), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase), fragments, variants and mixtures thereof.

In one embodiment, the antigen is a skin-associated antigen. Examples of skin-associated antigens include, but are not limited to, keratinocytes antigens, an antigen present in the dermis or epidermis, a melanocyte antigen (such as, for example, melanin or tyrosinase), desmoglein (e.g., desmoglein 1 or 3, that may also be referred to as Dsg1/3), BP180, BP230, plectin, integrins (e.g., integrin α4β6), collagens (e.g., collagen type VII), laminins (e.g., laminin 332 or laminin γ1), plakins (e.g., envoplakin, periplakin, or desmoplakins), keratins (e.g., KRT5, KRT8, KRT15, KRT17 and KRT31), keratin filament-associated proteins, filaggrin, corneodesmosin, and elastin.

In one embodiment, the antigen is an antigen involved in graft rejection or GVHD. Examples of such antigens include, but are not limited to, the MHC specific to the transplanted tissue or to the host, β2-microglobulin, antigens from ABO system, antigens from rhesus system (in particular antigens from the C, c, E et e and D system) and isohaemagglutinins. Other examples of antigens that may be involved in graft rejection or GVHD include, but are not limited to HLA-DR (in particular during the first six months following grafting), HLA-B (in particular during the first two years following grafting), HLA-A, minor histocompatibility antigens (miHA, e.g., HLA-E, HLA-F and HLA-G), HLAs corresponding to MHC class I (A, B, and C), HLAs corresponding to MHC class II (DP, DM, DOA, DOB, DQ, and DR) and HLAs corresponding to MHC class III (e.g., components of the complement system).

In one embodiment, the antigen is a HLA-A2 cell surface protein. In one embodiment, the extracellular binding domain comprises an antibody directed to HLA-A2 or an antigen binding fragment thereof.

The term "HLA-A2" as used herein refers to human leukocyte antigen (HLA) proteins including cell surface proteins, encoded by the HLA-A*02 allele family at the HLA-A locus of the HLA gene complex. HLA proteins encompassed by the term "HLA-A2" include HLA proteins identified as belonging to the HLA-A*02 antigen type by serological testing or genotyping. Additional names for the HLA-A*02 antigen type include "HLA-A2", HLA-A02" and "HLA-A*2". Different naming systems have been developed which identify HLA proteins encoded by this family of alleles including the HLA naming system developed in 2010 by the WHO Committee for Factors of the HLA System. The term "HLA-A2" refer to HLA proteins encoded by alleles having designations according to this naming system which begin with "HLA-A*02", including but not limited to designations which begin with "HLA-A*02:01", "HLA-A*02:02", "HLA-A*02:03", "HLA-A*02:04", "HLA-A*02:05", "HLA-A*02:06" "HLA-A*02:07", "HLA-A*02:08", "HLA-A*02:09", "HLA-A*02:10", and "HLA-A*02:11". The allele designations may be italicized. The allele designations which begin with "HLA-A*02:" followed by 2 or 3 additional digits may constitute the complete designation or a beginning portion of the designation. The term "HLA-A2" also refer to HLA proteins identified with designations which begin with "HLA-A*02" according to this naming system, including but not limited to the designations "HLA-A*02:01", "HLA-A*02:02", "HLA-A*02:03", "HLA-A*02:04", "HLA-A*02:05", "HLA-A*02:06", "HLA-A*02:07", "HLA-A*02:08", "HLA-A*02:09", "HLA-A*02:10", and "HLA-A*02:11".

Other examples of autoantigens include, without limitation, aquaporin water channels (such as, for example, aquaporin-4 water channel (AQP4)), Hu, Ma2, collapsin response-mediator protein 5 (CRMP5), and amphiphysin, voltage-gated potassium channel (VGKC), N-methyl-d-aspartate receptor (NMDAR), α-amino-3-hydroxy-5-methyl-4-isoxazoleproprionic acid (AMPAR), thyroid peroxidase, thyroglobulin, anti-N-methyl-D-aspartate receptor (NR1 subunit), Rh blood group antigens, I antigen, desmoglein 1 or 3 (Dsg1/3), BP180, BP230, Acetylcholine nicotinic postsynaptic receptors, thyrotropin receptors, platelet integrin, GpIIb:IIIa, Collagen (such as, for example, Collagen alpha-3(IV) chain), rheumatoid factor, calpastatin, citrullinated proteins, Myelin basic protein (MBP), Myelin oligodendrocyte glycoprotein (MOG) peptides, alpha-beta-crystallin, DNA, histone, ribosomes, RNP, tissue transglutaminase (TG2), intrinsic factor, 65-kDa antigen, phosphatidylserine, ribosomal phosphoproteins, anti-neutrophil cytoplasmic antibody, Scl-70, U1-RNP, ANA, SSA, anti-SSB, antinuclear antibodies (ANA), antineutrophil cytoplasm antibodies (ANCA), Jo-1, antimitochondrial antibodies, gp210, p62, sp100, antiphospholipid antibodies, U1-70 kd snRNP, GQ1b ganglioside, GM1, asialo GM1, GD1b, anti-smooth muscle antibodies (ASMA), anti-liver-kidney microsome-1 antibodies (ALKM-1), anti-liver cytosol antibody-1 (ALC-1), IgA antiendomysial antibodies, neutrophil granule proteins, streptococcal cell wall antigen, intrinsic factor of gastric parietal cells, insulin (IAA), glutamic acid decarboxylase (GAA or GAD) and protein tyrosine phosphatase (such as, for example, IA2 or ICA512), PLA2R1 and THSD7A1.

In one embodiment, the antigen is a cancer antigen.

As used herein, the term "cancer antigen" refers to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively.

Other cancer antigens include, but are not limited to, 707-AP (707 alanine proline), AFP (alpha (a)-fetoprotein), ART-4 (adenocarcinoma antigen recognized by T4 cells), BAGE (B antigen; b-catenin/m, b-catenin/mutated), BCMA (B cell maturation antigen), Bcr-abl (breakpoint cluster region-Abelson), CAIX (carbonic anhydrase IX), CD19 (cluster of differentiation 19), CD20 (cluster of differentiation 20), CD22 (cluster of differentiation 22), CD30 (cluster of differentiation 30), CD33 (cluster of differentiation 33), CD44v7/8 (cluster of differentiation 44, exons 7/8), CAMEL (CTL-recognized antigen on melanoma), CAP-1 (carcinoembryonic antigen peptide-1), CASP-8 (caspase-8), CDC27m (cell-division cycle 27 mutated), CDK4/m (cycline-dependent kinase 4 mutated), CEA (carcinoembryonic antigen), CT (cancer/testis (antigen)), Cyp-B (cyclophilin B), DAM (differentiation antigen melanoma), EGFR (epidermal growth factor receptor), EGFRvIII (epidermal growth factor receptor, variant III), EGP-2 (epithelial glycoprotein 2), EGP-40 (epithelial glycoprotein 40), Erbb2, 3, 4 (erythroblastic leukemia viral oncogene homolog-2, -3, 4), ELF2M (elongation factor 2 mutated), ETV6-AML1 (Ets variant gene 6/acute myeloid leukemia 1 gene ETS), FBP (folate binding protein), fAchR (Fetal acetylcholine receptor), G250 (glycoprotein 250), GAGE (G antigen), GD2 (disialoganglioside 2), GD3 (disialoganglioside 3), GnT-V (N-acetylglucosaminyltransferase V), Gp100 (glycoprotein 100 kD), HAGE (helicose antigen), HER-2/neu (human epidermal receptor-2/neurological; also known as EGFR2), HLA-A (human leukocyte antigen-A) HPV (human papilloma virus), HSP70-2M (heat shock protein 70-2 mutated), HST-2 (human signet ring tumor-2), hTERT or hTRT (human telomerase reverse transcriptase), iCE (intestinal carboxyl esterase), IL-13R-a2 (interleukin-13 receptor subunit alpha-2), KIAA0205, KDR (kinase insert domain receptor), κ-light chain, LAGE (L antigen), LDLR/FUT (low density lipid receptor/GDP-L-fucose: b-D-galactosidase 2-a-Lfucosyltransferase), LeY (Lewis-Y antibody), L1 CAM (L1 cell adhesion molecule), MAGE (melanoma antigen), MAGE-A1 (Melanoma-associated antigen 1), mesothelin, Murine CMV infected cells, MART-1/Melan-A (melanoma antigen recognized by T cells-I/Melanoma antigen A), MCi R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NKG2D (Natural killer group 2, member D) ligands, NY-BR-1 (New York breast differentiation antigen 1), NY-ESO-1 (New York esophageal squamous cell carcinoma-1), oncofetal antigen (h5T4), P15 (protein 15), p190 minor bcr-abl (protein of 190 KD bcr-abl), Pml/RARa (promyelocytic leukaemia/retinoic acid receptor a), PRAME (preferentially expressed antigen of melanoma), PSA (prostate-specific antigen), PSCA (Prostate stem cell antigen), PSMA (prostate-specific membrane antigen), RAGE (renal antigen), RU1 or RU2 (renal ubiquitous 1 or 2), SAGE (sarcoma antigen), SART-1 or SART-3 (squamous antigen rejecting tumor 1 or 3), SSX1, -2, -3, 4 (synovial sarcoma X1, -2, -3, -4), TAA (tumor-associated antigen), TAG-72 (Tumor-associated glycoprotein 72), TEL/AML1 (translocation Ets-family leukemia/acute myeloid leukemia 1), TPI/m (triosephosphate isomerase mutated), TRP-1 (tyrosinase related protein 1, or gp75), TRP-2 (tyrosinase related protein 2), TRP-2/INT2 (TRP-2/intron 2), VEGF-R2 (vascular endothelial growth factor receptor 2), or WT1 (Wilms' tumor gene).

Other examples of autoantigens include, without limitation, aquaporin water channels (such as, for example, aquaporin-4 water channel (AQP4)), Hu, Ma2, collapsin response-mediator protein 5 (CRMP5), and amphiphysin, voltage-gated potassium channel (VGKC), N-methyl-d-aspartate receptor (NMDAR), α-amino-3-hydroxy-5-methyl-4-isoxazoleproprionic acid (AMPAR), thyroid peroxidase, thyroglobulin, anti-N-methyl-D-aspartate receptor (NR1 subunit), Rh blood group antigens, I antigen, desmoglein 1 or 3 (Dsg1/3), BP180, BP230, Acetylcholine nicotinic post-synaptic receptors, thyrotropin receptors, platelet integrin, GpIIb:IIIa, Collagen (such as, for example, Collagen alpha-3(IV) chain), rheumatoid factor, calpastatin, citrullinated proteins, Myelin basic protein (MBP), Myelin oligodendrocyte glycoprotein (MOG) peptides, alpha-beta-crystallin, DNA, histone, ribosomes, RNP, tissue transglutaminase (TG2), intrinsic factor, 65-kDa antigen, phosphatidylserine, ribosomal phosphoproteins, anti-neutrophil cytoplasmic antibody, Scl-70, U1-RNP, ANA, SSA, anti-SSB, antinuclear antibodies (ANA), antineutrophil cytoplasm antibodies (ANCA), Jo-1, antimitochondrial antibodies, gp210, p62, sp100, antiphospholipid antibodies, U1-70 kd snRNP, GQ1b ganglioside, GM1, asialo GM1, GD1b, anti-smooth muscle antibodies (ASMA), anti-liver-kidney microsome-1 antibodies (ALKM-1), anti-liver cytosol antibody-1 (ALC-1), IgA antiendomysial antibodies, neutrophil granule proteins, streptococcal cell wall antigen, intrinsic factor of gastric parietal cells, insulin (IAA), glutamic acid decarboxylase (GAA or GAD) and protein tyrosine phosphatase (such as, for example, IA2 or ICA512), PLA2R1 and THSD7A1.

In one embodiment, said at least one other extracellular antigen binding domain (preferably scFv) is capable of binding to an antigen associated with infected cells.

As used herein, the term "infected cells" refers to cells contaminated with something that affects their quality, character, or condition unfavorably.

In one embodiment, the antigen is associated with virally infected cells. In another embodiment, the antigen is associated with bacterially infected cells. In another embodiment, the antigen is associated with fungally infected cells. In another embodiment, the antigen is associated with parasitic infected cells.

In another embodiment, said at least one other extracellular antigen binding domain (preferably scFv) is capable of binding to an inhaled allergen, an ingested allergen or a contact allergen.

Examples of inhaled allergens include, but are not limited to, allergens from *Astigmata* (e.g., *Acarus siro* (Storage mite, Aca s 13), *Blomia tropicalis* (Mite, Blo t), *Dermatophagoides farinae* (American house dust mite, Der f), *Dermatophagoides microceras* (House dust mite, Der m), *Dermatophagoides pteronyssinus* (European house dust mite, Der p), *Euroglyphus maynei* (House dust mite, Eur m), *Glycyphagus domesticus* (Storage mite, Gly d 2), *Lepidoglyphus destructor* (Storage mite, Lep d), *Tyrophagus putrescentiae* (Storage mite, Tyr p)); *Blattaria* (e.g., *Blattella germanica* (German cockroach, Bla g), *Periplaneta americana* (American cockroach, Per a)); *Coleoptera* (e.g., *Harmonia axyridis* (Asian ladybeetle, Har a)), Diptera (e.g., *Aedes aegypti* (Yellow fever mosquito, Aed a), *Chironomus kiiensis* (Midge, Chi k), *Chironomus thummi thummi* (Midge, Chi t), *Forcipomyia taiwana* (Biting midge, For t), *Glossina morsitans* (Savannah Tsetse fly, Glo m), *Hemidiptera: Triatoma protracta* (California kissing bug, Tria p)), Hymenoptera (e.g., *Apis cerana* (Eastern hive bee, Api c), *Apis dorsata* (Giant honeybee, Api d), *Apis mellifera* (Honey bee, Api m), *Bombus pennsylvanicus* (Bumble bee, Bom p), *Bombus terrestris* (Bumble bee, Bom t), *Dolichovespula arenaria* (Yellow hornet, Dol a), *Dolichovespula maculata* (White face hornet, Dol m), *Myrmecia pilosula* (Australian jumper ant, Myr p), *Polistes annularis* (Wasp, Pol a), *Polistes dominulus* (Mediterranean paper wasp, Pol d), *Polistes exclamans* (Wasp, Pol e), *Polistes fuscatus* (Wasp, Pol f), *Polistes gallicus* (Wasp, Pol g), *Polistes metricus* (Wasp, Pol m), *Polybia paulista* (Wasp, Pol p), *Polybia scutellaris* (Wasp, Pol s), *Solenopsis geminata* (Tropical fire ant, Sol g), *Solenopsis invicta* (Red imported fire ant, Sol i), *Solenopsis richteri* (Black fire ant, Sol r), *Solenopsis saevissima* (Brazilian fire ant, Sol s), *Vespa crabro* (European hornet, Vesp c), *Vespa mandarinia* (Giant asian hornet, Vesp m), *Vespula fiavopilosa* (Yellow jacket, Vesp f), *Vespula germanica* (Yellow jacket, Vesp g), *Vespula maculifrons* (Yellow jacket, Vesp m), *Vespula pensylvanica* (Yellow jacket, Vesp p), *Vespula squamosa* (Yellow jacket, Vesp s), *Vespula vidua* (Wasp, Vesp vi), *Vespula vulgaris* (Yellow jacket, Vesp v)), Ixodida (e.g., *Argas reflexus* (Pigeon tick, Arg r)), Lepidoptera (e.g., *Bombyx mori* (Silk moth, Bomb n), *Plodia interpunctella* (Indianmeal moth, Plo i), *Thaumetopoea pityocampa* (Pine processionary moth, Tha p)), Thysanura (e.g., *Lepisma saccharina* (Silverfish, Lep s)), Siphonaptera (e.g., *Ctenocephalides felis felis* (Cat flea, Cte f)), Carnivora (e.g., *Canis familiaris* (dog, Can f), *Felis domesticus* (cat, Fel d)); Lagomorpha (e.g., *Oryctolagus cuniculus* (rabbit, Ory c), Perissodactlyla: *Equus caballus* (domestic horse, Equ c)), Pleuronectiformes (e.g., *Lepidorhombus whiffiagonis* (Megrim, Whiff, Gallo, Lep w)); Rodentia (e.g., *Cavia porcellus* (guinea pig, Cav p), *Mus musculus* (mouse, Mus m), *Rattus norvegius* (rat, Rat n)); Coniferales: *Chamaecyparis obtusa* (Japanese cypress, Cha o), *Cupressus arizonica* (Cypress, Cup a), *Cryptomeria japonica* (Sugi, Cry j), *Cupressus sempervirens* (Common cypress, Cup s), *Juniperus ashei* (Mountain cedar, Jun a), *Juniperus oxycedrus* (Prickly juniper, Jun o), *Juniperus sabinoides* (Mountain cedar, Jun s), *Juniperus virginiana* (Eastern red cedar, Jun v)); Gentianales (e.g., *Catharanthus roseus* (Rosy periwinkle, Cat r)); Poales (e.g., *Anthoxanthum odoratum* (Sweet vernal grass, Ant o 1), *Cynodon dactylon* (Bermuda grass, Cyn d 1, Cyn d 7, Cyn d 12, Cyn d 15, Cyn d 22w, Cyn d 23, Cyn d 24), *Dactylis glomerata* (Orchard grass, Dae g 1, Dae g 2, Dae g 3, Dae g 4, Dae g 5), *Festuca pratensis* (Meadow fescue, Fes p 4)), *Holcus lanatus* (Velvet grass, Hol 11, Hol 1 5), *Hordeum vulgare* (Barley, Hor v 1, Hor v 5, Hor v 12, Hor v 15, Hor v 16, Hor v 17, Hor v 21), *Lolium perenne* (Rye grass, Lol p 1, Lol p 2, Lol p 3, Lol p 4, Lol p 5, Lol p 11), *Oryza sativa* (Rice, Ory s 1, Ory s 12), *Paspalum notarum* (Bahia grass, Pas n 1), *Phalaris aquatica* (Canary grass, Pha a 1, Pha a 5), *Phleum pratense* (Timothy, Phl p 1, Phl p 2, Phl p 4, Phl p 5, Phl p 6, Phl p 7, Phl p 11, Phl p 12, Phl p 13), *Poa pratensis* (Kentucky blue grass, Poa p 1, Poa p 5), *Secale cereale* (Rye, Sec c 1, Sec c 20), *Sorghum halepense* (Johnson grass, Sor h 1), *Triticum aestivum* (Wheat, Tri a 12, Tri a 14, Tri a 185, Tri a 19, Tri a 25, Tri a 26, Tri a 27, Tri a 28, Tri a 29, Tri a 30), *Zea mays* (Maize, Zea m 1, Zea m 12, Zea m 14, Zea m 25), Fagales: *Alnus glutinosa* (Alder, Aln g 1, Aln g 4), *Betula verrucosa* (Birch, Bet v 1, Bet v 2, Bet v 3, Bet v 4, Bet v 5, Bet v 6, Bet v 7), *Carpinus betuhxs* (Hornbeam, Car b 1)); Lamiales (e.g., *Fraxinus excelsior* (Ash, Fra e 1), *Ligustrum vulgare* (Privet, Lig v), *Syringa vulgaris* (Lilac, Syr v)); Malpighiales (e.g., *Hevea brasiliensis* (para rubber tree (latex), Hev b 1, Hev b 2, Hev b 3, Hev b 4, Hev b 5, Hev b 6, Hev b 7, Hev b 8, Hev b 9, Hev b 10, Hev b 11, Hev b 12, Hev b 13)); Proteales (e.g., *Platanus acerifolia* (London plane tree, Pla a 1, Pla a 2, Pla a 3), *Platanus orientalis* (Oriental plane, Pla or 1, Pla or 2, Pla or 3)).

Examples of ingested allergens include, but are not limited to, allergens from Fungi Ascomycota, such as, for example, Dothideales (e.g., *Alternaria alternata* (*Alternaria* rot fungus, Alt a), *Cladosporium cladosporioides* (Cla c), *Cladosporium herbarum* (Cla h), *Curvularia lunata* (Cur 1),—Eurotiales: *Aspergillus flavus* (Asp fl), *Aspergillus fumigatus* (Asp f), *Aspergillus niger* (Asp n), *Aspergillus oryzae* (Asp o), *Penicillium brevicompactum* (Pen b), *Penicillium chrysogenum* (Pen ch), *Penicillium citrinum* (Pen c), *Penicillium oxalicum* (Pen o)), Hypocreales (e.g., *Fusarium culmorum* (Fus c)); Onygenales (e.g., *Trichophyton rubrum* (Tri r), *Trichophyton tonsurans* (Tri t), Saccharomycetales: *Candida albicans* (Yeast, Cand a), *Candida boidinii* (Yeast, Cand b)); Tuberculariales (e.g., *Epicoccum purpurascens* (Epi p)), allergens from Fungi Basidiomycota, such as, for example, Hymenomycetes (e.g., *Coprinus comatus* (Shaggy mane, Cop c), *Psilocybe cubensis* (Magic mushroom, Psi c), Urediniomycetes (e.g., *Rhodotorula mucilaginosa* (Yeast, Rho m)); Ustilaginomycetes (e.g., *Malassezia furfur* (Pityriasis versicolor infect. Agent, Mala f), *Malassezia sympodialis* (Mala s)); antibiotics (such as, for example, Penicillins, Cephalosporins, Aminosides, Quinolones, Macrolides, Tetracycline, Sulfamids); drugs (such as, for example, acetylsalicylic acid, vaccines, morphines and derivatives); vitamins such as, for example, vitamin KI; and food allergens (such as, for example, allergen from milk, egg, peanut, tree nut (walnut, cashew, etc.), fish, shellfish, soy, wheat, and carrot, apple, pear, avocado, apricot, peach).

Examples of contact allergens include, but are not limited to, heavy metals (such as, for example, nickel, chrome, gold), latex, haptens such as, for example halothane, hydralazine.

In one embodiment, said at least one other extracellular antigen binding domain (preferably scFv) is capable of binding to an antigen selected from the group comprising ovalbumin, MOG, type II collagen fragments, variants and mixtures thereof. In one embodiment, said at least one other extracellular antigen binding domain (preferably scFv) is capable of binding to an antigen selected from the group comprising citrullinated vimentin, citrullinated type II collagen, citrullinated fibrinogen, variants and mixtures thereof.

In one embodiment, said at least one other extracellular antigen binding domain (preferably scFv) is capable of binding to ovalbumin, fragments, variants and mixtures thereof.

In another embodiment, said at least one other extracellular antigen binding domain (preferably scFv) is capable of binding to MOG, fragments, variants and mixtures thereof.

In another embodiment, said at least one other extracellular antigen binding domain (preferably scFv) is capable of binding to type II collagen, fragments, variants and mixtures thereof.

In another embodiment, said at least one other extracellular antigen binding domain (preferably scFv) is capable of binding to citrullinated vimentin, citrullinated type II collagen, citrullinated fibrinogen, fragments, variants and mixtures thereof.

In one embodiment, the extracellular IL-23R binding domain is connected to a transmembrane domain by a hinge domain.

In one embodiment, the hinge domain is a short oligo- or polypeptide linker, preferably having a length ranging from 2 to 10 amino acids, as described hereinabove.

Another example of hinge domain that may be used in the present invention is described in WO2012/138475, incorporated herein by reference.

In one embodiment, the hinge domain comprises an amino acid sequence selected from the group comprising the amino acid sequence AGSSSSGGSTTGGSTT (SEQ ID NO: 7), the amino acid sequence GTTAASGSSGGSSSGA (SEQ ID NO: 8), the amino acid sequence SSATATAGTGSSTGST (SEQ ID NO: 9), and the amino acid sequence TSGSTGTAASSTSTST (SEQ ID NO: 10).

In one embodiment, the hinge domain is encoded by a nucleotide sequence of GGTGGCGGAGGTTCTGGAGGTGGAGGTTCC (SEQ ID NO: 11).

In another embodiment, the hinge domain is a KIR2DS2 hinge corresponding to KIRRDSS (SEQ ID NO: 12).

In one embodiment, the hinge domain comprises or consists in the amino acid sequence of a CD8 hinge (SEQ ID NO: 13) or an amino acid sequence with at least about 95, preferably about 96%, 97%, 98% or 99% identity to SEQ ID NO: 13. In one embodiment, the hinge domain is a CD8 hinge encoded by the nucleic acid sequence SEQ ID NO: 14 or a nucleic acid sequence with at least about 95, preferably about 96%, 97%, 98% or 99% identity to SEQ ID NO: 14.

In another embodiment, the hinge domain comprises or consists in the amino acid sequence of a IgG4 hinge (SEQ ID NO: 15), or an amino acid sequence with at least about 95, preferably about 96%, 97%, 98% or 99% identity to SEQ ID NO: 15. In one embodiment, the hinge domain is an IgG4 hinge encoded by the nucleic acid sequence SEQ ID NO: 16 or a nucleic acid sequence with at least about 95, preferably about 96%, 97%, 98% or 99% identity to SEQ ID NO: 16.

In another embodiment, the hinge domain comprises or consists in the amino acid sequence of a IgD hinge (SEQ ID NO: 17) or an amino acid sequence with at least about 95, preferably about 96%, 97%, 98% or 99% identity to SEQ ID NO: 17. In one embodiment, the hinge domain is an IgD hinge encoded by the nucleic acid sequence SEQ ID NO: 18 or a nucleic acid sequence with at least about 95, preferably about 96%, 97%, 98% or 99% identity to SEQ ID NO: 18.

In another embodiment, the hinge region comprises or consists in the amino acid sequence of a CD28 hinge (SEQ ID NO: 19) or an amino acid sequence with at least about 95, preferably about 96%, 97%, 98% or 99% identity to SEQ ID NO: 19. In one embodiment, the hinge domain is a CD28 hinge encoded by the nucleic acid SEQ ID NO: 20 or a nucleic acid sequence with at least about 95, preferably about 96%, 97%, 98% or 99% identity to SEQ ID NO: 20.

Examples of transmembrane domains that may be used in the chimeric receptor of the invention include, but are not limited to, transmembrane domains of an alpha, beta or zeta chain of a T-cell receptor, or of CD28, CD3 gamma, CD3 delta, CD3 epsilon, CD3 zeta, CD45, CD4, CD5, CD8, CD9, CD16, CD22, CD33, CD37, CD64, CD80, CD86, CD134, CD137, CD154, KIRDS2, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R a, ITGA1, VLA1, CD49a, ITGA4, IA4, CD49D, ITGA6, VLA-6, CD49f, ITGAD, CD1 Id, ITGAE, CD103, ITGAL, CD11a, LFA-1, ITGAM, CD11b, PD1, ITGAX, CDllc, ITGB1, CD29, ITGB2, CD18, LFA-1, ITGB7, TNFR2, DNAM1 (CD226), SLAMF4 (CD244, 2B4), CD84, CD96 (Tactile), CEACAMI, CRT AM, Ly9 (CD229), CD160 (BY55), PSGL1, CDIOO (SEMA4D), SLAMF6 (NTB-A, Lyl08), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In one embodiment, the transmembrane domain comprises or consists in the amino acid sequence of a CD8 transmembrane domain (SEQ ID NO: 21), or an amino acid sequence with at least about 95, preferably about 96%, 97%, 98% or 99% identity to SEQ ID NO: 21. In another embodiment, the transmembrane domain comprises or consists in an amino acid sequence having at least one, two or three modifications but not more than 20, 10 or 5 modifications of an amino acid sequence of SEQ ID NO: 21, or an amino acid sequence with at least about 95, preferably about 96%, 97%, 98% or 99% identity to SEQ ID NO: 21.

In another embodiment, the transmembrane domain is encoded by the nucleotide sequence of a CD8 transmembrane domain (SEQ ID NO: 22), or a nucleotide sequence with at least about 95, preferably about 96%, 97%, 98% or 99% identity to SEQ ID NO: 22.

In another embodiment, the transmembrane domain comprises or consists in the amino acid sequence of a CD28 transmembrane domain (SEQ ID NO: 23) or an amino acid sequence with at least about 95, preferably about 960%, 970%, 98% or 99% identity to SEQ ID NO: 23. In one embodiment, the transmembrane domain is a CD28 transmembrane domain encoded by the nucleic acid sequence SEQ ID NO: 24 or a nucleic acid sequence with at least about 95, preferably about 96%, 97%, 98% or 99% identity to SEQ ID NO: 24.

In one embodiment, the transmembrane domain may be recombinant, in which case it will comprise predominantly hydrophobic amino acids such as valine or leucine.

In one embodiment, the intracellular signaling domain may comprise the entire intracellular portion, or the entire native intracellular signaling domain, of the molecule from which it is derived, or a functional fragment or derivative thereof.

In one embodiment, the intracellular signaling domain comprises a T cell primary signaling domain (or a sequence derived therefrom) and optionally one or more intracellular domain(s) of a T cell costimulatory molecule (or sequence(s) derived therefrom).

In one embodiment, the intracellular signaling domain of the CAR of the invention consists in a primary signaling domain.

In one embodiment, the intracellular signaling domain comprises one or more intracellular domain(s) of a T cell costimulatory molecule. In one embodiment, the intracellular signaling domain consists in one or more intracellular domain(s) of a T cell costimulatory molecule.

In another embodiment, the intracellular signaling domain of the CAR of the invention comprises at least one costimulatory domain and a primary signaling domain.

In another embodiment, the intracellular signaling domain of the CAR of the invention comprises at least two costimulatory domains and a primary signaling domain.

In one embodiment of the invention, the T cell primary signaling domain comprises a signaling domain of a protein selected in the group of CD3 zeta, CD3 gamma, CD3 delta, CD3 epsilon, common FcR gamma (FCER1G), FcR beta (Fc Epsilon Rib), CD79a, CD79b, Fcgamma RIIa, DAP10, and DAP 12 and sequences derived therefrom.

In one embodiment, the T cell primary signaling domain comprises or consists in a functional signaling domain of CD3 zeta.

In one embodiment, the T cell primary signaling domain comprises or consists in the amino acid sequence of the CD3-zeta domain of SEQ ID NO: 25, 26, 61 or 62, or an amino acid sequence with at least about 95, preferably about 96%, 97%, 98° % or 99% identity to SEQ ID NO: 25, 26, 61 or 62.

In another embodiment, the CD3 zeta primary signaling domain comprises or consists in an amino acid sequence having at least one, two or three modifications but not more than 20, 10 or 5 modifications of an amino acid sequence of SEQ ID NO: 25, 26, 61 or 62, or an amino acid sequence with at least about 95, preferably about 96%, 97%, 98% or 99% identity to SEQ ID NO: 25, 26, 61 or 62.

Thus, in one embodiment, the nucleic acid sequence encoding the T cell primary signaling domain comprises or consists in the nucleic acid sequence of the CD3-zeta domain of SEQ ID NO: 27 or SEQ ID NO: 28, or a nucleotide sequence with at least about 95, preferably about 96%, 97%, 98% or 99% identity to SEQ ID NO: 27 or SEQ ID NO: 28.

T cell primary signaling domains that act in a stimulatory manner may comprise signaling motifs known as immunoreceptor tyrosine-based activation motifs (ITAMS).

Examples of ITAM containing T cell primary intracellular signaling domains that are of particular use in the invention include, but are not limited to, those of (or derived from) CD3 zeta, common FcR gamma (FCER1G), Fc gamma RIIa, FcR beta (Fc Epsilon Rib), CD3 gamma, CD3 delta, CD3 epsilon, CD5, CD22, CD66b, CD79a, CD79b, DAP10, and DAP12.

In one embodiment, the T cell primary signaling domain comprises a modified ITAM domain, e.g., a mutated ITAM domain which has altered (e.g., increased or decreased) activity as compared to the native ITAM domain. In one embodiment, a primary signaling domain comprises a modified ITAM-containing primary intracellular signaling domain, e.g., an optimized and/or truncated ITAM-containing primary intracellular signaling domain. In an embodiment, a primary signaling domain comprises one, two, three, four or more ITAM motifs.

In one embodiment, the intracellular signaling domain of the CAR of the invention comprises a T cell primary signaling domain (such as, for example, a CD3-zeta signaling domain), combined with one or more costimulatory signaling domains.

Examples of intracellular domains of a T cell costimulatory molecule include, but are not limited to, the signaling domains of proteins selected in the group of CD27, CD28, 4-1BB (CD137), an MHC class I molecule, BTLA, a Toll ligand receptor, OX40, CD30, CD40, PD-1, ICOS (CD278), lymphocyte function-associated antigen-1 (LFA-1), CD2, CD7, LIGHT, NKG2C, B7-H3, a ligand that specifically binds with CD83, CDS, ICAM-1, GITR, ARHR, BAFFR, HVEM (LIGHTR), SLAMF7, NKp80 (KLRF1), NKp44, NKp30, NKp46, CD160 (BY55), CD19, CD19a, CD4, CD8alpha, CD8beta, IL2ra, IL6Ra, IL2R beta, IL2R gamma, IL7R alpha, IL-13RA1/RA2, IL-33R(IL1RL1), IL-10RA/RB, IL-4R, IL-5R (CSF2RB), IL-21R, ITGA4, VLA1, CD49a, ITGA4, IA4, CD49D, ITGA6, VLA-6, CD49f, ITGAD, CD11 d, ITGAE, CD103, ITGAL, CD11a/ CD18, ITGAM, CD11b, ITGAX, CD11c, ITGB1, CD29, ITGB2, CD18, ITGB7, NKG2D, NKG2C, CTLA-4 (CD152), CD95, TNFR1 (CD120a/TNFRSF1A), TNFR2 (CD120b/TNFRSF1B), TGFbR1/2/3, TRANCE/RANKL, DNAM1 (CD226), SLAMF4 (CD244, 2B4), CD84, CD96 (Tactile), CEACAMI, CRTAM, Ly9 (CD229), PSGL1, CD100 (SEMA4D), CD69, SLAMF6 (NTB-A, Lyl08), SLAM (SLAMF1, CD150, IPO-3), BLAME (SLAMF8), SELPLG (CD162), LTBR, LAT, GADS, SLP-76, PAG/Cbp, common gamma chain, a ligand that specifically binds with CD83, NKp44, NKp30, NKp46, or NKG2D, and any combination thereof.

In one embodiment of the invention, the chimeric receptor comprises at least one intracellular domain of a T cell costimulatory molecule selected from the group comprising 4-1BB, ICOS, CD27, OX40, CD28, CTLA4 and PD-1.

In one embodiment, the T cell costimulatory signaling domain comprises or consists in the amino acid sequence of a 4-1BB intracellular domain (SEQ ID NO: 29) or an amino acid sequence with at least about 95, preferably about 96%, 97%, 98% or 99% identity to SEQ ID NO: 29. In another embodiment, the T cell costimulatory signaling domain comprises or consists in an amino acid sequence having at least one, two or three modifications but not more than 20, 10 or 5 modifications of an amino acid sequence of SEQ ID NO: 29.

In one embodiment, the T cell costimulatory signaling domain comprises or consists in the amino acid sequence of a CD27 intracellular domain (SEQ ID NO: 30) or an amino acid sequence with at least about 95, preferably about 96%, 97%, 98% or 99% identity to SEQ ID NO: 30. In another embodiment, the T cell costimulatory signaling domain comprises or consists in an amino acid sequence having at least one, two or three modifications but not more than 20, 10 or 5 modifications of an amino acid sequence of SEQ ID NO: 30.

In one embodiment, the T cell costimulatory signaling domain comprises or consists in the amino acid sequence of a CD28 intracellular domain (SEQ ID NO: 31) or an amino acid sequence with at least about 95, preferably about 96%, 97%, 98% or 99% identity to SEQ ID NO: 31. In another embodiment, the T cell costimulatory signaling domain comprises or consists in an amino acid sequence having at least one, two or three modifications but not more than 20, 10 or 5 modifications of an amino acid sequence of SEQ ID NO: 31.

In one embodiment of the invention, the chimeric receptor comprises a combination of at least two intracellular domains of a T cell costimulatory molecule, preferably selected from an intracellular domain of CD28, an intracellular domain of CD27 and an intracellular domain of 4-1BB.

In one embodiment, the chimeric receptor comprises the amino acid sequence of a 4-1BB intracellular domain (SEQ ID NO: 29) or an amino acid sequence with at least about 95, preferably about 96%, 97%, 98% or 99% identity to SEQ ID NO: 29 and the amino acid sequence of a CD27 intracellular domain (SEQ ID NO: 30) or an amino acid sequence with at least about 95, preferably about 96%, 97%, 98% or 99% identity to SEQ ID NO: 30.

In another embodiment, the chimeric receptor comprises the amino acid sequence of a 4-1BB intracellular domain (SEQ ID NO: 29) or an amino acid sequence with at least about 95, preferably about 96° %, 97%, 98% or 99% identity to SEQ ID NO: 29 and the amino acid sequence of a CD28 intracellular domain (SEQ ID NO: 31) or an amino acid sequence with at least about 95, preferably about 96%, 97%, 98% or 99% identity to SEQ ID NO: 31.

In yet another embodiment, the chimeric receptor comprises the amino acid sequence of a CD27 intracellular domain (SEQ ID NO: 30) or an amino acid sequence with at least about 95, preferably about 96%, 97%, 98% or 99% identity to SEQ ID NO: 30 and the amino acid sequence of a CD28 intracellular domain (SEQ ID NO: 31) or an amino acid sequence with at least about 95, preferably about 96%, 97%, 98% or 99% identity to SEQ ID NO: 31.

In one embodiment, the chimeric receptor comprises the amino acid sequence of a 4-1BB intracellular domain (SEQ ID NO: 29) or an amino acid sequence with at least about 95, preferably about 96%, 97%, 98% or 99% identity to SEQ ID NO: 29 and the amino acid sequence of a CD27 intracellular domain (SEQ ID NO: 30) or an amino acid sequence with at least about 95, preferably about 96%, 97%, 98% or 99% identity to SEQ ID NO: 30 and the amino acid sequence of a CD28 intracellular domain (SEQ ID NO: 31) or an amino acid sequence with at least about 95, preferably about 96%, 97%, 98% or 990% identity to SEQ ID NO: 31.

Thus, in one embodiment, the nucleic acid sequence encoding the T cell costimulatory signaling domain comprises the nucleic acid sequence of a 4-1BB intracellular domain (SEQ ID NO: 32) or a nucleic acid sequence with at least about 95, preferably about 96%, 970%, 98% or 99% identity to SEQ ID NO: 32, and/or the nucleic acid sequence of a CD27 intracellular domain (SEQ ID NO: 33) or a nucleic acid sequence with at least about 95, preferably about 96%, 97%, 98% or 99% identity to SEQ ID NO: 33, and/or the nucleic acid sequence of a CD28 intracellular domain (SEQ ID NO: 34), or a nucleic acid sequence with at least about 95, preferably about 96%, 97%, 98% or 99% identity to SEQ ID NO: 34.

In embodiment, the intracellular signaling domain of the CAR of the invention comprises:
the amino acid sequence of a 4-1BB intracellular domain of SEQ ID NO: 29 or an amino acid sequence with at least about 95, preferably about 96%, 97%, 98% or 99% identity to SEQ ID NO: 29, and/or the amino acid sequence of a CD27 intracellular domain of SEQ ID NO: 30 or an amino acid sequence with at least about 95, preferably about 96%, 97%, 98% or 99% identity to SEQ ID NO: 30, and/or the amino acid sequence of a CD28 intracellular domain of SEQ ID NO: 31 or an amino acid sequence with at least about 95, preferably about 96%, 97%, 98% or 99% identity to SEQ ID NO: 31; and
the amino acid sequence of a CD3-zeta intracellular domain of SEQ ID NO: 25, 26, 61 or 62, or an amino acid sequence with at least about 95, preferably about 96%, 970%, 98° % or 99% identity to SEQ ID NO: 25, 26, 61 or 62;
wherein the sequences comprised in the intracellular domain are expressed in the same frame and as a single polypeptide chain.

Thus, in one embodiment, the nucleic acid sequence encoding the intracellular signaling domain of the CAR of the invention comprises:
the nucleic acid sequence of a 4-1BB intracellular domain of SEQ ID NO: 32 or a nucleic acid sequence with at least about 95, preferably about 96%, 97%, 98% or 99% identity to SEQ ID NO: 32, and/or the nucleic acid sequence of a CD27 intracellular domain of SEQ ID NO: 33 or a nucleic acid sequence with at least about 95, preferably about 96%, 97%, 98% or 99% identity to SEQ ID NO: 33, and/or the nucleic acid sequence of a CD28 intracellular domain of SEQ ID NO: 34 or a nucleic acid sequence with at least about 95, preferably about 96%, 97%, 98% or 99% identity to SEQ ID NO: 34; and
the nucleic acid sequence of a CD3-zeta intracellular domain of SEQ ID NO: 27 or SEQ ID NO: 28, or a sequence with at least about 95, preferably about 96%, 97%, 98% or 99% identity to SEQ ID NO: 27 or SEQ ID NO: 28.

In one embodiment, the intracellular signaling domain of the CAR of the invention comprises at least two different domains (e.g., a primary signaling domain and at least one intracellular domain of a T cell costimulatory molecule) that may be linked to each other in a random or in a specified order.

Optionally, a short oligo- or polypeptide linker, for example, between 2 and 10 amino acids (e.g., 2, 3, 4, 5, 6, 7, 8, 9, or 10 amino acids) in length may form the linkage between distinct signaling domains. In one embodiment, a glycine-serine doublet (GS) is used as a suitable linker. In one embodiment, a single amino acid, e.g., an alanine (A), a glycine (G), is used as a suitable linker. Other examples of linker are described herein.

In another embodiment, the intracellular signaling domain of the CAR of the invention comprises two or more, e.g., 2, 3, 4, 5, or more, costimulatory signaling domains. In another embodiment, the two or more, e.g., 2, 3, 4, 5, or more, costimulatory signaling domains, are separated by a linker molecule, e.g., a linker molecule as described hereinabove.

In one embodiment, the intracellular signaling domain of the chimeric receptor of the invention comprises the primary signaling domain of CD3-zeta (preferably SEQ ID NO: 25, 26, 61 or 62) and the co-stimulatory signaling domain of CD28 (preferably SEQ ID NO: 31).

In another embodiment, the intracellular signaling domain of the chimeric receptor of the invention comprises the primary signaling domain of CD3-zeta (preferably SEQ ID NO: 25, 26, 61 or 62) and the co-stimulatory signaling domain of 4-1BB (preferably SEQ ID NO: 29).

In another embodiment, the intracellular signaling domain of the chimeric receptor of the invention comprises the signaling domain of CD3-zeta (preferably SEQ ID NO: 25, 26, 61 or 62) and the signaling domain of CD27 (preferably SEQ ID NO: 30).

In one embodiment, the CAR of the invention further comprises a leader sequence located N-terminally from the IL-23R specific extracellular binding domain. A non-limiting example of leader sequence is a leader sequence of CD8 that may comprise or consists in the sequence SEQ ID NO: 39.

In one embodiment, the CAR further comprises a tag, such as, for example, a tag for quality control, enrichment, tracking in vivo and the like. Said tag may be localized N-terminally, C-terminally and/or internally. Examples of tags that may be used in the CAR of the invention are well known by the skilled artisan. For example, but without limitation, a tag used in the invention can be a tag selected from the group comprising or consisting of Hemagglutinin Tag, Poly Arginine Tag, Poly Histidine Tag, Myc Tag, Strep Tag, S-Tag, HAT Tag, 3× Flag Tag, Calmodulin-binding peptide Tag, SBP Tag, Chitin binding domain Tag, GST Tag, Maltose-Binding protein Tag, Fluorescent Protein Tag, T7 Tag, V5 Tag and Xpress Tag. Other examples of tag include, without limitation, NWSHPQFEK (SEQ ID NO: 59) or SAWSHPQFEK (SEQ ID NO: 60).

In one embodiment, the CAR of the invention further comprises P2A (SEQ ID NO: 44) and GFP (SEQ ID NO: 45) sequences.

According to a first embodiment, the CAR of the invention comprises an extracellular IL-23R binding domain, optionally an extracellular hinge domain, a transmembrane domain, and an intracellular signaling domain.

In one embodiment, the CAR of the invention comprises an IL-23R binding domain; a transmembrane domain of CD8 (preferably SEQ ID NO: 21); and a CD3-zeta primary signaling domain (preferably SEQ ID NO: 25, 26, 61 or 62).

In one embodiment, the CAR of the invention comprises an IL-23R binding domain; a transmembrane domain of CD28 (preferably SEQ ID NO: 23); and a CD3-zeta primary signaling domain (preferably SEQ ID NO: 25, 26, 61 or 62).

In another embodiment, the CAR of the invention comprises an IL-23R binding domain; a hinge domain of CD8 (preferably SEQ ID NO: 13); a transmembrane domain of CD8 (preferably SEQ ID NO: 21); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD28 (preferably SEQ ID NO: 23); and a CD3-zeta primary signaling domain (preferably SEQ ID NO: 25, 26, 61 or 62).

In another embodiment, the CAR of the invention comprises an IL-23R binding domain; a hinge domain of IgG4 (preferably SEQ ID NO: 15); a transmembrane domain of CD8 (preferably SEQ ID NO: 21); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD28 (preferably SEQ ID NO: 23); and a CD3-zeta primary signaling domain (preferably SEQ ID NO: 25, 26, 61 or 62).

In another embodiment, the CAR of the invention comprises an IL-23R binding domain; a hinge domain of IgD (preferably SEQ ID NO: 17); a transmembrane domain of CD8 (preferably SEQ ID NO: 21); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD28 (preferably SEQ ID NO: 23); and a CD3-zeta primary signaling domain (preferably SEQ ID NO: 25, 26, 61 or 62).

In another embodiment, the CAR of the invention comprises an IL-23R binding domain; a hinge domain of CD28 (preferably SEQ ID NO: 19); a transmembrane domain of CD8 (preferably SEQ ID NO: 21); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD28 (preferably SEQ ID NO: 23); and a CD3-zeta primary signaling domain (preferably SEQ ID NO: 25, 26, 61 or 62).

According to a second embodiment, the CAR of the invention comprises an IL-23R binding domain, optionally an extracellular hinge domain, a transmembrane domain, a single intracellular domain of a T cell costimulatory molecule and a T cell primary signaling domain.

In one embodiment, the CAR of the invention comprises an IL-23R binding domain; a transmembrane domain of CD8 (preferably SEQ ID NO: 21); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a transmembrane domain of CD8 (preferably SEQ ID NO: 21); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a transmembrane domain of CD8 (preferably SEQ ID NO: 21); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a transmembrane domain of CD28 (preferably SEQ ID NO: 23); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a transmembrane domain of CD28 (preferably SEQ ID NO: 23); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a transmembrane domain of CD28 (preferably SEQ ID NO: 23); an intracellular domain of CD28 (preferably SEQ ID NO: 31); and a CD3-zeta primary signaling domain (preferably SEQ ID NO: 25, 26, 61 or 62).

In another embodiment, the CAR of the invention comprises an IL-23R binding domain; a hinge domain of CD8 (preferably SEQ ID NO: 13); a transmembrane domain of CD8 (preferably SEQ ID NO: 21); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD8 (preferably SEQ ID NO: 21); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD8 (preferably SEQ ID NO: 21); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD28 (preferably SEQ ID NO: 23); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD28 (preferably SEQ ID NO: 23); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD28 (preferably SEQ ID NO: 23); an intracellular domain of CD28 (preferably SEQ ID NO: 31); and a CD3-zeta primary signaling domain (preferably SEQ ID NO: 25, 26, 61 or 62).

In another embodiment, the CAR of the invention comprises an IL-23R binding domain; a hinge domain of IgG4 (preferably SEQ ID NO: 15); a transmembrane domain of CD8 (preferably SEQ ID NO: 21); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD8 (preferably SEQ ID NO: 21); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD8 (preferably SEQ ID NO: 21); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD28 (preferably SEQ ID NO: 23); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD28 (preferably SEQ ID NO: 23); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD28 (preferably SEQ ID NO: 23); an intracellular domain of CD28 (preferably SEQ ID NO: 31); and a CD3-zeta primary signaling domain (preferably SEQ ID NO: 25, 26, 61 or 62).

In another embodiment, the CAR of the invention comprises an IL-23R binding domain; a hinge domain of IgD (preferably SEQ ID NO: 17); a transmembrane domain of CD8 (preferably SEQ ID NO: 21); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD8 (preferably SEQ ID NO: 21); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD8 (preferably SEQ ID NO: 21); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD28 (preferably SEQ ID NO: 23); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD28 (preferably SEQ ID NO: 23); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD28 (preferably SEQ ID NO: 23); an intracellular domain of CD28 (preferably SEQ ID NO: 31); and a CD3-zeta primary signaling domain (preferably SEQ ID NO: 25, 26, 61 or 62).

In another embodiment, the CAR of the invention comprises an IL-23R binding domain; a hinge domain of CD28 (preferably SEQ ID NO: 19); a transmembrane domain of CD8 (preferably SEQ ID NO: 21); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD8 (preferably SEQ ID NO: 21); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD8 (preferably SEQ ID NO: 21); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD28 (preferably SEQ ID NO: 23); an intracellular domain of 4-1BB (preferably SEQ ID NO: 29); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD28

(preferably SEQ ID NO: 23); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD28 (preferably SEQ ID NO: 23); an intracellular domain of CD28 (preferably SEQ ID NO: 31); and a CD3-zeta primary signaling domain (preferably SEQ ID NO: 25, 26, 61 or 62).

According to a third embodiment, the CAR of the invention comprises an IL-23R binding domain, optionally an extracellular hinge domain, a transmembrane domain, two intracellular domains of a T cell costimulatory molecule and a T cell primary signaling domain.

In one embodiment, the CAR of the invention comprises an IL-23R binding domain; a transmembrane domain of CD8 (preferably SEQ ID NO: 21); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a transmembrane domain of CD8 (preferably SEQ ID NO: 21); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a transmembrane domain of CD8 (preferably SEQ ID NO: 21); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a transmembrane domain of CD28 (preferably SEQ ID NO: 23); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a transmembrane domain of CD28 (preferably SEQ ID NO: 23); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a transmembrane domain of CD28 (preferably SEQ ID NO: 23); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In another embodiment, the CAR of the invention comprises an IL-23R binding domain; a hinge domain of CD8 (preferably SEQ ID NO: 13); a transmembrane domain of CD8 (preferably SEQ ID NO: 21); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD8 (preferably SEQ ID NO: 21); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD8 (preferably SEQ ID NO: 21); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD28 (preferably SEQ ID NO: 23); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD28 (preferably SEQ ID NO: 23); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of CD8 (preferably SEQ ID NO: 13); a transmembrane domain of CD28 (preferably SEQ ID NO: 23); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In another embodiment, the CAR of the invention comprises an IL-23R binding domain; a hinge domain of IgG4 (preferably SEQ ID NO: 15); a transmembrane domain of CD8 (preferably SEQ ID NO: 21); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD8 (preferably SEQ ID NO: 21); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD8 (preferably SEQ ID NO: 21); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD28 (preferably SEQ ID NO: 23); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD28 (preferably SEQ ID NO: 23); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of IgG4 (preferably SEQ ID NO: 15); a transmembrane domain of CD28 (preferably SEQ ID NO: 23); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In another embodiment, the CAR of the invention comprises an IL-23R binding domain; a hinge domain of IgD, preferably comprising the amino acid sequence SEQ ID NO: 17; a transmembrane domain of CD8 (preferably SEQ ID NO: 21); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD8 (preferably SEQ ID NO: 21); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD8 (preferably SEQ ID NO: 21); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD28 (preferably SEQ ID NO: 23); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD28 (preferably SEQ ID NO: 23); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of IgD (preferably SEQ ID NO: 17); a transmembrane domain of CD28 (preferably SEQ ID NO: 23); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In another embodiment, the CAR of the invention comprises an IL-23R binding domain; a hinge domain of CD28 (preferably SEQ ID NO: 19); a transmembrane domain of CD8 (preferably SEQ ID NO: 21); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD8 (preferably SEQ ID NO: 21); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD8 (preferably SEQ ID NO: 21); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD28 (preferably SEQ ID NO: 23); an intracellular domain of 4-1BB (preferably SEQ ID NO: 29); an intracellular domain of CD27 (preferably SEQ ID NO: 30); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD28 (preferably SEQ ID NO: 23); an intracellular domain of 4-1BB (preferably SEQ ID NO: 29); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises an IL-23R binding domain; a hinge domain of CD28 (preferably SEQ ID NO: 19); a transmembrane domain of CD28 (preferably SEQ ID NO: 23); an intracellular domain of CD27 (preferably SEQ ID NO: 30); an intracellular domain of CD28 (preferably SEQ ID NO: 31); and a CD3-zeta primary signaling domain (preferably SEQ ID NO: 25, 26, 61 or 62).

In one embodiment, the CAR of the invention comprises (i) an IL-23R binding domain, (ii) a hinge region of human CD28, (iii) a transmembrane domain of human CD28, (iv) an intracellular domain of human CD28 and (v) an intracellular domain of human CD3ζ chain.

In one embodiment, the part of the CAR comprising a hinge region of human CD28, a transmembrane domain of human CD28, an intracellular domain of human CD28 and an intracellular domain of human CD3ζ chain corresponds to the amino acid sequence of SEQ ID NO: 35 or 63 or an amino acid sequence with at least about 95, preferably about 96%, 97%, 98% or 99% identity to SEQ ID NO: 35 or 63.

In one embodiment, the CAR of the invention comprises an IL-23R binding domain, linked to an amino acid sequence of SEQ ID NO: 35 or 63 or a sequence or an amino acid sequence with at least about 95, preferably about 96%, 97%, 98% or 99% identity to SEQ ID NO: 35 or 63.

In another embodiment, the CAR of the invention comprises (i) an IL-23R binding domain, (ii) a hinge region of human CD8, (iii) a transmembrane domain of human CD8, (iv) an intracellular domain of human 4-1BB and (v) an intracellular domain of human CD3ζ. In one embodiment, the part of the CAR comprising a hinge region of human CD8, a transmembrane domain of human CD8, an intracellular domain of human 4-1BB and an intracellular domain of human CD3ζ comprises or consists in the amino acid sequence SEQ ID NO: 49, 50, 70 or 71, or any amino acid sequence with at least about 95, preferably about 96%, 97%, 98% or 99% identity with SEQ ID NO: 49, 50, 70 or 71.

In another embodiment, the CAR of the invention comprises (i) an IL-23R binding domain, (ii) a hinge region of human CD8, (iii) a transmembrane domain of human CD8, (iv) an intracellular domain of human CD28 and (v) an intracellular domain of human CD3ζ. In one embodiment, the part of the CAR comprising a hinge region of human CD8, a transmembrane domain of human CD8, an intracellular domain of human CD28 and an intracellular domain of human CD3ζ comprises or consists in the amino acid sequence SEQ ID NO: 51 or 72, or any amino acid sequence with at least about 95, preferably about 96%, 97%, 98% or 99% identity with SEQ ID NO: 51 or 72.

In one embodiment, the CAR of the invention comprises an anti-IL-23R scFv (e.g., comprising or consisting of a sequence SEQ ID NO: 55, 36 or 57, preferably SEQ ID NO: 55), a hinge region of CD8, a transmembrane domain of human CD8, an intracellular domain of human 4-1BB and an intracellular domain of human CD3ζ. In one embodiment, said CAR comprises or consists in SEQ ID NO: 41, 43, 65 or 67 or an amino acid sequence with at least about 95, preferably about 96%, 97%, 98% or 99% identity to SEQ ID NO: 41, 43, 65 or 67.

In one embodiment, the CAR of the invention comprises a leader sequence of CD8, an anti-IL-23R scFv (e.g., comprising or consisting of a sequence SEQ ID NO: 55, 36 or 57, preferably SEQ ID NO: 55), a hinge region of CD8, a transmembrane domain of human CD8, an intracellular domain of human 4-1BB and an intracellular domain of human CD3ζ. In one embodiment, said CAR comprises or consists in SEQ ID NO: 40, 42, 64 or 66 or an amino acid sequence with at least about 95, preferably about 96%, 97%, 98% or 99% identity to SEQ ID NO: 40, 42, 64 or 66.

In one embodiment, the CAR of the invention comprises an anti-IL-23R scFv (e.g., comprising or consisting of a sequence SEQ ID NO: 55, 36 or 57, preferably SEQ ID NO: 55), a hinge region of CD8, a transmembrane domain of human CD8, an intracellular domain of human CD28 and an intracellular domain of human CD3ζ. In one embodiment, said CAR comprises or consists in SEQ ID NO: 48, 53, 69 or 74 or an amino acid sequence with at least about 95, preferably about 96%, 97%, 980% or 99% identity to SEQ ID NO: 48, 53, 69 or 74.

In one embodiment, the CAR of the invention comprises a leader sequence of CD8, an anti-IL-23R scFv (e.g., comprising or consisting of a sequence SEQ ID NO: 55, 36 or 57, preferably SEQ ID NO: 55), a hinge region of CD8, a transmembrane domain of human CD8, an intracellular domain of human CD28 and an intracellular domain of human CD3ζ. In one embodiment, said CAR comprises or consists in SEQ ID NO: 47, 52, 68 or 73 or an amino acid sequence with at least about 95, preferably about 96%, 97%, 98% or 99% identity to SEQ ID NO: 47, 52, 68 or 73.

In one embodiment, the CAR of the invention comprises a CD8 leader sequence having the SEQ ID NO: 39, an anti-human IL-23R scFv, comprising a VH having the sequence SEQ ID NO: 37 and a VL having SEQ ID NO: 38, linked by a $(G_4S)_3$ linker (SEQ ID NO: 3), a hinge domain derived from CD8a having the sequence of SEQ ID NO: 13, a human CD8a transmembrane domain having the SEQ ID NO: 21, and an intracellular signaling domain comprising a human 4-1BB signaling domain having SEQ ID NO: 29 and a human CD3 zeta domain having SEQ ID NO: 26.

In one embodiment, the CAR of the invention comprises an anti-human IL-23R scFv, comprising a $V_H$ having the sequence SEQ ID NO: 37 and a $V_L$ having SEQ ID NO: 38, linked by a $(G_4S)_3$ linker (SEQ ID NO: 3), a hinge domain derived from CD80 having the sequence of SEQ ID NO: 13, a human CD8a transmembrane domain having the SEQ ID NO: 21, and an intracellular signaling domain comprising a human 4-1BB signaling domain having SEQ ID NO: 29 and a human CD3 zeta domain having SEQ ID NO: 26.

In one embodiment, the CAR of the invention has a sequence SEQ ID NO: 54 or a sequence with at least about 95, preferably about 96%, 97%, 98% or 99% identity to SEQ ID NO: 54.

The present invention further relates to a T cell, preferably an isolated T cell, engineered to express on the cell surface a CAR as described hereinabove.

The present invention also relates to an isolated and/or substantially purified T cell population comprising cells engineered to express on the cell surface a CAR as described hereinabove.

In one embodiment, the T cells of the invention are suppressive for cells expressing at their surface the IL-23R recognized by the CAR.

In one embodiment, the T cells of the invention are cytotoxic for cells expressing at their surface the IL-23R recognized by the CAR.

In one embodiment, the T cell population of the invention comprises or consists in regulatory T cells (Treg), CD8$^+$ T cells, CD4$^+$ T cells and NK T cells.

In one embodiment, the T cells of the invention are Treg cells.

In one embodiment, the T cell is a regulatory immune cell, such as, for example, any regulatory immune cell suitable for use in cellular therapy.

In one embodiment, the Treg cells of the population of the invention all express a chimeric receptor (CAR) as defined herein and may thus be defined as CAR-monospecific (i.e., all the Treg cells recognize the same antigen (IL-23R) with the CAR they express). In one embodiment, the Treg cell population is TCR-monospecific (i.e., all the Treg cells recognize the same antigen with their TCR). In another embodiment, the Treg cell population is TCR-polyspecific (i.e., the Treg cells may recognize different antigens with their TCR).

In one embodiment, the Treg cell population is TCR-monospecific, and the TCR recognizes an antigen, a fragment of an antigen, a variant of an antigen or a mixture thereof.

In one embodiment, the Treg cell population is TCR-monospecific, and the TCR is specific of a food antigen from the common human diet.

In another embodiment, the Treg cell population is TCR-monospecific, and the TCR is specific of an autoantigen, such as, for example, a multiple sclerosis-associated antigen, a joint-associated antigen, an eye-associated antigen, a human HSP antigen, a skin-associated antigen or an antigen involved in graft rejection or GVHD. Examples of autoantigens, in particular of multiple sclerosis-associated antigens, joint-associated antigens, eye-associated antigens, human HSP antigens, skin-associated antigens and antigens involved in graft rejection or GVHD are given herein.

In another embodiment, the Treg cell population is TCR-monospecific, and the TCR is specific of an inhaled allergen, an ingested allergen or a contact allergen.

In one embodiment, the Treg cell population is TCR-monospecific, and the TCR is specific of an antigen selected from the group comprising ovalbumin, MOG, type II collagen fragments, variants and mixtures thereof.

In one embodiment, the Treg cell population is TCR-monospecific, and the TCR is specific of ovalbumin, fragments, variants and mixtures thereof.

In another embodiment, the Treg cell population is TCR-monospecific, and the TCR is specific of MOG, fragments, variants and mixtures thereof.

In another embodiment, the Treg cell population is TCR-monospecific, and the TCR is specific of type II collagen, fragments, variants and mixtures thereof.

In one embodiment, Treg cells expressing the CAR of the invention are suppressive against cells expressing IL-23R recognized by the CAR.

In one embodiment, the CAR of the invention when expressed by a Treg cell, confers to the Treg cell the ability to bind to cells expressing IL-23R on their cell surface and be activated by the IL-23R, differently from the antigen that the Treg cells are or would have been specific or activated by.

The Treg cell population of the invention may thus be defined as a redirected Treg cell population. As used herein, the term "redirected" refers to a Treg cell carrying a chimeric receptor as described herein, which confers to the Treg cell the ability to bind to and be activated by a ligand that is different from the one the Treg cell is or would have been specific or be activated by.

In one embodiment, Treg cells of the invention are not cytotoxic. In another embodiment, Treg cells of the invention are cytotoxic.

Examples of cells expressing IL-23R include, but are not limited to, Th17, αβ T cells, neutrophils, gamma delta T cells, NK, NKT, dendritic cells and macrophages.

In one embodiment, Treg cells of the invention may be selected form the group comprising CD4$^+$CD25 Foxp3$^+$ Treg, Tr1 cells, TGF-β secreting Th3 cells, regulatory NK T cells, regulatory γδ T cells, regulatory CD8$^+$ T cells, and double negative regulatory T cells.

In one embodiment, the regulatory cell is a CD4$^+$ regulatory T cell (Treg). In one embodiment, the Treg is a thymus derived Treg or an adaptive or induced Treg. In one embodiment, the Treg is a CD4$^+$FOXP3$^+$ regulatory T cell or a CD4$^+$FOXP3$^-$ regulatory T cell (Tr1 cell), preferably a CD4$^+$FOXP3$^+$ regulatory T cell.

In one embodiment, the regulatory cell is a CD8$^+$ regulatory T cell (Treg). In one embodiment, the CD8$^+$ regulatory T cell is selected from the group consisting of a CD8+CD28$^-$ regulatory T cell, a CD8$^+$CD103$^+$ regulatory T cell, a CD8$^+$FoxP3$^+$ regulatory T cell, a CD8$^+$CD122$^+$ regulatory T cell, and any combination thereof. In one embodiment, the regulatory cell is an INFγ$^+$IL10$^+$IL34$^+$ CD8$^+$CD45RC$^{low}$ regulatory T cell.

In one embodiment, the Treg cells of the invention are mammal cells, preferably human Treg cells.

In one embodiment, the Treg is derived from stem cells, such as, for example, induced-stem cells, including, without limitation, induced pluripotent stem cells (iPS or iPSC).

As used herein, the term "induced pluripotent stem cells", "iPS" or "iPSC" refers to artificial pluripotent stem cells, derived from non-pluripotent cells, in particular from adult somatic cells, by dedifferentiation or reprogramming. In particular, iPSC may be obtained by introducing a specific set of pluripotency-associated genes into a cell, such as, for example, the transcription factors Oct4 (Pou5f1), Sox2, cMyc, and Klf4. In addition to their morphology, self-renewal property and pluripotency similar to those of embryonic stem cells, iPSCs also exhibit epigenetic reprogramming with an overall profile of histone methylation and gene expression very close to that of embryonic stem cells. IPSCs in particular express pluripotency markers, such as for example, Nanog, Sox2, Oct4 and Ssea3/4 proteins.

In one embodiment, the regulatory cell has the following phenotype: CD4$^+$CD25$^+$, such as, for example, CD4$^+$CD25$^+$CD127$^-$, such as, for example, CD4$^+$CD25$^+$CD127$^-$CD45RA$^+$. Preferably, the regulatory immune cell has the following phenotype: FoxP3$^+$CD4$^+$CD25$^+$, such as, for example, FoxP3$^+$CD4$^+$CD25$^+$CD127$^-$, such as, for example, FoxP3$^+$CD4$^+$CD25$^+$CD127$^-$CD45RA$^+$.

In one embodiment, the regulatory cell presents at least one of the following phenotypes: CD4$^+$CD25$^+$, FoxP3$^+$, CD127$^{lo/-}$, CTLA-4$^+$, CD39$^+$, Helios$^+$, CD62L$^{+/hi}$, VLA4$^+$, LFA1$^+$, CD49b$^{int}$, ITGb7$^{int}$, PSGL-1$^+$, ICOS$^+$, GITR$^+$, PD-1$^{int}$, Perf$^{lo/-}$, CCR7$^+$. In one embodiment, the immune regulatory cell does not express Granzyme A and/or Granzyme B.

In one embodiment, the determination of the expression level of molecules is conducted by flow cytometry, immunofluorescence or image analysis, for example high content analysis. Preferably, the determination of the expression level of molecules is conducted by flow cytometry. In one embodiment, before conducting flow cytometry analysis, cells are fixed and permeabilized, thereby allowing detecting intracellular proteins.

In one embodiment, the determination of the expression level of a molecule in a cell population comprises determining the percentage of cells of the cell population expressing the molecule (i.e. cells "+" for the molecule). Preferably, said percentage of cells expressing the molecule is measured by FACS.

The terms "expressing (or +)" and "not expressing (or -)" are well known in the art and refer to the expression level of the cell marker of interest, in that the expression level of the cell marker corresponding to "+" is high or intermediate, also referred as "+/-", and the expression level of the cell marker corresponding to "-" is null.

The term "low" or "lo" or "lo/-" is well known in the art and refers to the expression level of the cell marker of interest, in that the expression level of the cell marker is low by comparison with the expression level of that cell marker in the population of cells being analyzed as a whole. More particularly, the term "lo" refers to a distinct population of cells that express the cell marker at a lower level than one or more other distinct population of cells.

The term "high" or "hi" or "bright" is well known in the art and refers to the expression level of the cell marker of interest, in that the expression level of the cell marker is high by comparison with the expression level of that cell marker in the population of cells being analyzed as a whole.

Generally, cells in the top 2, 3, 4, or 5% of staining intensity are designated "hi", with those falling in the top half of the population categorized as being "+". Those cells falling below 50%, of fluorescence intensity are designated as "lo" cells and below 5% as "-" cells.

The expression level of the cell marker of interest is determined by comparing the Median Fluorescence Intensity (MFI) of the cells from the cell population stained with fluorescently labeled antibody specific for this marker to the fluorescence intensity (FI) of the cells from the same cell population stained with fluorescently labeled antibody with an irrelevant specificity but with the same isotype, the same fluorescent probe and originated from the same specie (referred as Isotype control). The cells from the population stained with fluorescently labeled antibody specific for this marker and that show equivalent MFI or a lower MFI than the cells stained with the isotype controls are not expressing this marker and then are designated (−) or negative. The cells from the population stained with fluorescently labeled antibody specific for this marker and that show a MFI value superior to the cells stained with the isotype controls are expressing this marker and then are designated (+) or positive.

In one embodiment, the cells of the Treg cell population of the invention express at their cell surface a CAR of the invention, and another receptor (herein referred to as "second receptor"), that binds to another ligand than the IL-23R recognized by the CAR of the invention. According to the invention, this other receptor comprises an extracellular ligand binding domain, optionally a hinge, optionally a transmembrane domain, and an intracellular signaling domain, as previously described.

In one embodiment, the second receptor is endogenous (such as, for example, the endogenous TCR). In another embodiment, the second receptor is exogenous, and its expression is induced in the cells of the Treg cell population of the invention by transformation or transduction of a nucleic acid encoding it. Said exogenous receptor may be an exogenous TCR or a CAR. Therefore, in one embodiment, the Treg cells of the invention express two CARs, wherein the first one recognizes a IL-23R, and the second one recognizes a distinct ligand. In another embodiment, the Treg cells of the invention express two CARs, wherein the first one recognizes a first epitope on an IL-23R, and the second one recognizes a distinct epitope on the same IL-23R. In another embodiment, the Treg cells of the invention express two CARs, wherein the first one recognizes an IL-23R, and the second one recognizes a distinct IL-23R (such as, for example, a variant of IL-23R).

In one embodiment, at least one of the CAR of the invention and the second receptor (preferably the second CAR) is inducible, i.e., its expression on the cell surface may be induced.

In one embodiment, the expression of one of the CAR of the invention and the second receptor (preferably the second CAR) is induced by the activation of the other receptor. In a first embodiment, the expression of the CAR of the invention is induced by the activation of the second receptor. In a second embodiment, the expression of the second receptor is induced by the activation of the CAR of the invention. Inducible CARs were previously described in the art, such as, for example, by Roybal et al (Cell, 2006).

In one embodiment, the second receptor, preferably the second CAR, is specific of an antigen, a fragment of an antigen, a variant of an antigen or a mixture thereof.

In one embodiment, the second receptor, preferably the second CAR, is specific of a food antigen from the common human diet.

The term "food antigen from common human diet" refers to an immunogenic peptide, which comes from foodstuffs common for humans, such as food antigens of the following non-limiting list: bovine antigens such as lipocalin, Ca-binding S100, alpha-lactalbumin, lactoglobulins such as beta-lactoglobulin, bovine serum albumin, caseins. Food-antigens may also be atlantic salmon antigens such as parvalbumin; chicken antigens such as ovomucoid, ovalbumin, Ag22, conalbumin, lysozyme or chicken serum albumin; peanut antigens; shrimp antigens such as tropomyosin; wheat antigens such as agglutinin or gliadin; celery antigens such as celery profilin; carrot antigens such as carrot profilin; apple antigens such as thaumatin, apple lipid transfer protein, or apple profilin; pear antigens such as pear profilin, or isoflavone reductase; avocado antigens such as endochitinase; apricot antigens such as apricot lipid transfer protein; peach antigens such as peach lipid transfer protein or peach profilin; soybean antigens such as HPS, soybean profilin or (SAM22) PR-I0 prot; fragments, variants and mixtures thereof.

In another embodiment, the second receptor, preferably the second CAR, is specific of an autoantigen, such as, for example, a multiple sclerosis-associated antigen, a joint-associated antigen, an eye-associated antigen, a human HSP antigen, a skin-associated antigen or an antigen involved in graft rejection or GVHD.

Examples of multiple sclerosis-associated antigens include, but are not limited to, myelin basic protein (MBP), myelin associated glycoprotein (MAG), myelin oligodendrocyte glycoprotein (MOG), proteolipid protein (PLP), oligodendrocyte myelin oligoprotein (OMGP), myelin associated oligodendrocyte basic protein (MOBP), oligodendrocyte specific protein (OSP/Claudinl 1), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase), fragments, variants and mixtures thereof.

Examples of joint-associated antigens include, but are not limited to, citrulline-substituted cyclic and linear filaggrin peptides, type II collagen peptides, human cartilage glycoprotein 39 (HCgp39) peptides, HSP, heterogeneous nuclear ribonucleoprotein (hnRNP) A2 peptides, hnRNP B1, hnRNP D, Ro60/52, HSP60, HSP65, HSP70 and HSP90, BiP, keratin, vimentin, fibrinogen, type I, III, IV and V collagen peptides, annexin V, Glucose 6 phosphate isomerase (GPI), acetyl-calpastatin, pyruvate dehydrogenase (PDH), aldolase, topoisomerase I, snRNP, PARP, Scl-70, Scl-100, phospholipid antigens including anionic cardiolipin and phosphatidylserine, neutrally charged phosphatidylethanolamine and phosphatidylcholine, matrix metalloproteinase, fibrillin, aggrecan, fragments, variants and mixtures thereof. Other examples of joint associated antigens include, but are not limited to, citrullinated vimentin, citrullinated type II collagen, citrullinated fibrinogen.

Examples of eye-associated antigens include, but are not limited to, type II collagen, retinal arrestin, S-arrestin, interphotoreceptor retinoid-binding proteins (IRBP1), beta-crystallin B1, retinal proteins, choroid proteins and fragments, variants and mixtures thereof.

Examples of human HSP antigens include, but are not limited to, human HSP60, HSP70, HSP90, fragments, variants and mixtures thereof.

In one embodiment, the antigen is an inflammatory nervous system condition-associated antigen, preferably a multiple sclerosis-associated antigen. Examples of inflammatory nervous system condition-associated antigens, preferably of multiple sclerosis-associated antigens include, but are not limited to myelin basic protein (MBP), myelin associated glycoprotein (MAG), myelin oligodendrocyte protein (MOG), proteolipid protein (PLP), oligodendrocyte myelin oligoprotein (OMGP), myelin associated oligodendrocyte basic protein (MOBP), oligodendrocyte specific protein (OSP/Claudinl 1), heat shock proteins, oligodendrocyte specific proteins (OSP), NOGO A, glycoprotein Po, peripheral myelin protein 22 (PMP22), 2'3'-cyclic nucleotide 3'-phosphodiesterase (CNPase), fragments, variants and mixtures thereof.

In one embodiment, the antigen is a skin-associated antigen. Examples of skin-associated antigens include, but are not limited to, keratinocytes antigens, an antigen present in the dermis or epidermis, a melanocyte antigen (such as, for example, melanin or tyrosinase), desmoglein (e.g., desmoglein 1 or 3, that may also be referred to as Dsg1/3), BP180, BP230, plectin, integrins (e.g., integrin α4β6), collagens (e.g., collagen type VII), laminins (e.g., laminin 332 or laminin γ1), plakins (e.g., envoplakin, periplakin, or desmoplakins), keratins (e.g., KRT5, KRT8, KRT15, KRT17 and KRT31), keratin filament-associated proteins, filaggrin, corneodesmosin, and elastin.

In one embodiment, the antigen is an antigen involved in graft rejection or GVHD. Examples of such antigens include, but are not limited to, the MHC specific to the transplanted tissue or to the host, β2-microglobulin, antigens from ABO system, antigens from rhesus system (in particular antigens from the C, c, E et e and D system) and isohaemagglutinins. Other examples of antigens that may be involved in graft rejection or GVHD include, but are not limited to HLA-DR (in particular during the first six months following grafting), HLA-B (in particular during the first two years following grafting), HLA-A, minor histocompatibility antigens (miHA, e.g., HLA-E, HLA-F and HLA-G), HLAs corresponding to MHC class I (A, B, and C), HLAs corresponding to MHC class II (DP, DM, DOA, DOB, DQ, and DR) and HLAs corresponding to MHC class III (e.g., components of the complement system).

In one embodiment, the antigen is a HLA-A2 cell surface protein. In one embodiment, the extracellular binding domain comprises an antibody directed to HLA-A2 or an antigen binding fragment thereof.

The term "HLA-A2" as used herein refers to human leukocyte antigen (HLA) proteins including cell surface proteins, encoded by the HLA-A*02 allele family at the HLA-A locus of the HLA gene complex. HLA proteins encompassed by the term "HLA-A2" include HLA proteins identified as belonging to the HLA-A*02 antigen type by serological testing or genotyping. Additional names for the HLA-A*02 antigen type include "HLA-A2", HLA-A02" and "HLA-A*2". Different naming systems have been developed which identify HLA proteins encoded by this family of alleles including the HLA naming system developed in 2010 by the WHO Committee for Factors of the HLA System. The term "HLA-A2" refer to HLA proteins encoded by alleles having designations according to this naming system which begin with "HLA-A*02", including but not limited to designations which begin with "HLA-A*02:01", "HLA-A*02:02", "HLA-A*02:03", "HLA-A*02:04", "HLA-A*02:05", "HLA-A*02:06", "HLA-A*02:07", "HLA-A*02:08", "HLA-A*02:09", "HLA-A*02:10", and "HLA-A*02:11". The allele designations may be italicized. The allele designations which begin with "HLA-A*02:" followed by 2 or 3 additional digits may constitute the complete designation or a beginning portion of the designation. The term "HLA-A2" also refer to HLA proteins identified with designations which begin with "HLA-A*02" according to this naming system, including but not limited to the designations "HLA-A*02:01", "HLA-A*02:02", "HLA-A*02:03", "HLA-A*02:04", "HLA-A*02:05", "HLA-A*02:06", "HLA-A*02:07", "HLA-A*02:08", "HLA-A*02:09", "HLA-A*02:10", and "HLA-A*02:11".

Other examples of autoantigens include, without limitation, aquaporin water channels (such as, for example, aquaporin-4 water channel (AQP4)), Hu, Ma2, collapsin response-mediator protein 5 (CRMP5), and amphiphysin, voltage-gated potassium channel (VGKC), N-methyl-d-aspartate receptor (NMDAR), α-amino-3-hydroxy-5-methyl-4-isoxazoleproprionic acid (AMPAR), thyroid peroxidase, thyroglobulin, anti-N-methyl-D-aspartate receptor (NR1 subunit), Rh blood group antigens, I antigen, desmoglein 1 or 3 (Dsg1/3), BPI 80, BP230, Acetylcholine nicotinic postsynaptic receptors, thyrotropin receptors, platelet integrin, GpIIb:IIIa, Collagen (such as, for example, Collagen alpha-3(IV) chain), rheumatoid factor, calpastatin, citrullinated proteins, Myelin basic protein (MBP), Myelin oligodendrocyte glycoprotein (MOG) peptides, alpha-beta-crystallin, DNA, histone, ribosomes, RNP, tissue transglutaminase (TG2), intrinsic factor, 65-kDa antigen, phosphatidylserine, ribosomal phosphoproteins, anti-neutrophil cytoplasmic antibody, Scl-70, U1-RNP, ANA, SSA, anti-SSB, antinuclear antibodies (ANA), antineutrophil cytoplasm antibodies (ANCA), Jo-1, antimitochondrial antibodies, gp210, p62, sp100, antiphospholipid antibodies, U1-70 kd snRNP, GQ1b ganglioside, GM1, asialo GM1, GD1b, anti-smooth muscle antibodies (ASMA), anti-liver-kidney microsome-1 antibodies (ALKM-1), anti-liver cytosol antibody-1 (ALC-1), IgA antiendomysial antibodies, neutrophil granule proteins, streptococcal cell wall antigen, intrinsic factor of gastric parietal cells, insulin (IAA), glutamic acid decarboxylase (GAA or GAD) and protein tyrosine phosphatase (such as, for example, IA2 or ICA512), PLA2R1 and THSD7A1.

In one embodiment, the antigen is a cancer antigen.

As used herein, the term "cancer antigen" refers to antigens which are differentially expressed by cancer cells and can thereby be exploited in order to target cancer cells. Cancer antigens are antigens which can potentially stimulate apparently tumor-specific immune responses. Some of these antigens are encoded, although not necessarily expressed, by normal cells. These antigens can be characterized as those which are normally silent (i.e., not expressed) in normal cells, those that are expressed only at certain stages of differentiation and those that are temporally expressed such as embryonic and fetal antigens. Other cancer antigens are encoded by mutant cellular genes, such as oncogenes (e.g., activated ras oncogene), suppressor genes (e.g., mutant p53), and fusion proteins resulting from internal deletions or chromosomal translocations. Still other cancer antigens can be encoded by viral genes such as those carried on RNA and DNA tumor viruses. Many tumor antigens have been defined in terms of multiple solid tumors: MAGE 1, 2, & 3, defined by immunity; MART-1/Melan-A, gp100, carcinoembryonic antigen (CEA), HER2, mucins (i.e., MUC-1), prostate-specific antigen (PSA), and prostatic acid phosphatase (PAP). In addition, viral proteins such as some encoded by hepatitis B (HBV), Epstein-Barr (EBV), and human papilloma (HPV) have been shown to be important in the development of hepatocellular carcinoma, lymphoma, and cervical cancer, respectively.

Other cancer antigens include, but are not limited to, 707-AP (707 alanine proline), AFP (alpha (a)-fetoprotein), ART-4 (adenocarcinoma antigen recognized by T4 cells), BAGE (B antigen; b-catenin/m, b-catenin/mutated), BCMA (B cell maturation antigen), Bcr-abl (breakpoint cluster region-Abelson), CAIX (carbonic anhydrase IX), CD19 (cluster of differentiation 19), CD20 (cluster of differentiation 20), CD22 (cluster of differentiation 22), CD30 (cluster of differentiation 30), CD33 (cluster of differentiation 33), CD44v7/8 (cluster of differentiation 44, exons 7/8), CAMEL (CTL-recognized antigen on melanoma), CAP-1 (carcinoembryonic antigen peptide-1), CASP-8 (caspase-8), CDC27m (cell-division cycle 27 mutated), CDK4/m (cycline-dependent kinase 4 mutated), CEA (carcinoembryonic antigen), CT (cancer/testis (antigen)), Cyp-B (cyclophilin B), DAM (differentiation antigen melanoma), EGFR (epidermal growth factor receptor), EGFRvIII (epidermal growth factor receptor, variant III), EGP-2 (epithelial glycoprotein 2), EGP-40 (epithelial glycoprotein 40), Erbb2, 3, 4 (erythroblastic leukemia viral oncogene homolog-2, -3, 4), ELF2M (elongation factor 2 mutated), ETV6-AML1 (Ets variant gene 6/acute myeloid leukemia 1 gene ETS), FBP (folate binding protein), fAchR (Fetal acetylcholine receptor), G250 (glycoprotein 250), GAGE (G antigen), GD2 (disialoganglioside 2), GD3 (disialoganglioside 3), GnT-V (N-acetylglucosaminyltransferase V), Gp100 (glycoprotein 100 kD), HAGE (helicose antigen), HER-2/neu (human epidermal receptor-2/neurological; also known as EGFR2), HLA-A (human leukocyte antigen-A) HPV (human papilloma virus), HSP70-2M (heat shock protein 70-2 mutated), HST-2 (human signet ring tumor-2), hTERT or hTRT (human telomerase reverse transcriptase), iCE (intestinal carboxyl esterase), IL-13R-a2 (Interleukin-13 receptor subunit alpha-2), KIAA0205, KDR (kinase insert domain receptor), κ-light chain, LAGE (L antigen), LDLR/FUT (low density lipid receptor/GDP-L-fucose: b-D-galactosidase 2-a-Lfucosyltransferase), LeY (Lewis-Y antibody), L1 CAM (L1 cell adhesion molecule), MAGE (melanoma antigen), MAGE-A1 (Melanoma-associated antigen 1), mesothelin, Murine CMV infected cells, MART-1/Melan-A (melanoma antigen recognized by T cells-I/Melanoma antigen A), MCi R (melanocortin 1 receptor), Myosin/m (myosin mutated), MUC1 (mucin 1), MUM-1, -2, -3 (melanoma ubiquitous mutated 1, 2, 3), NA88-A (NA cDNA clone of patient M88), NKG2D (Natural killer group 2, member D) ligands, NY-BR-1 (New York breast differentiation antigen 1), NY-ESO-1 (New York esophageal squamous cell carcinoma-1), oncofetal antigen (h5T4), P15 (protein 15), p190 minor bcr-abl (protein of 190 KD bcr-abl), Pml/RARa (promyelocytic leukaemia/retinoic acid receptor a), PRAME (preferentially expressed antigen of melanoma), PSA (prostate-specific antigen), PSCA (Prostate stem cell antigen), PSMA (prostate-specific membrane antigen), RAGE (renal antigen), RU1 or RU2 (renal ubiquitous 1 or 2), SAGE (sarcoma antigen), SART-1 or SART-3 (squamous antigen rejecting tumor 1 or 3), SSX1, -2, -3, 4 (synovial sarcoma X1, -2, -3, -4), TAA (tumor-associated antigen), TAG-72 (Tumor-associated glycoprotein 72), TEL/AML1 (translocation Ets-family leukemia/acute myeloid leukemia 1), TPI/m (triosephosphateisomerasemutated), TRP-1 (tyrosinase related protein 1, or gp75), TRP-2 (tyrosinase related protein 2), TRP-2/INT2 (TRP-2/intron 2), VEGF-R2 (vascular endothelial growth factor receptor 2), or WT1 (Wilms' tumor gene).

In one embodiment, the antigen is associated with infected cells.

As used herein, the term "infected cells" refers to cells contaminated with something that affects their quality, character, or condition unfavorably.

In one embodiment, the antigen is associated with virally infected cells. In another embodiment, the antigen is associated with bacterially infected cells. In another embodiment, the antigen is associated with fungally infected cells. In another embodiment, the antigen is associated with parasitic infected cells.

In another embodiment, the second receptor, preferably the second CAR, is specific of an inhaled allergen, an ingested allergen or a contact allergen.

In one embodiment, the second receptor, preferably the second CAR, is specific of an antigen selected from the group comprising ovalbumin, MOG, type II collagen fragments, variants and mixtures thereof.

In one embodiment, the second receptor, preferably the second CAR, is specific of ovalbumin, fragments, variants and mixtures thereof.

In another embodiment, the second receptor, preferably the second CAR, is specific of MOG, fragments, variants and mixtures thereof.

In another embodiment, the second receptor, preferably the second CAR, is specific of type II collagen, fragments, variants and mixtures thereof.

In one embodiment, the CAR of the invention comprises a first intracellular signaling domain, and the second receptor comprises a distinct second intracellular signaling domain. In a first embodiment, the CAR of the invention comprises a T cell primary signaling domain (such as, for example, CD3 zeta), and the second receptor comprises a costimulatory signaling domain (such as, for example, of 4-1BB, CD28 or a combination of costimulatory signaling domain of 4-1BB and CD28). In a second embodiment, the CAR of the invention comprises a costimulatory signaling domain (such as, for example, of 4-1BB, CD28 or a combination of costimulatory signaling domain of 4-1BB and CD28), and the second receptor comprises a T cell primary signaling domain (such as, for example, CD3 zeta).

Consequently, according to these embodiments, the complete activation of the Treg cell population of the invention requires both the binding of the CAR of the invention to IL-23R, and the binding of the second receptor to the ligand to which it is directed.

In one embodiment, the ligand recognized by the second receptor is expressed or present at the diseased tissue or organ, or at the site of the autoimmune response. Consequently, suppressive activity for cells expressing IL-23R will be induced only at the diseased tissue or organ or at the site of the autoimmune response, when said ligand will be present and recognized by the second receptor on the cells of Treg cell population.

In one embodiment, the chimeric receptor of the invention further comprises an extracellular ligand binding domain recognizing a ligand distinct from the IL-23R recognized by the chimeric receptor. In one embodiment, said ligand binding domain is an antibody or an antigen binding fragment thereof.

In one embodiment, the chimeric receptor of the invention comprises an extracellular ligand binding domain comprising an IL-23R binding domain and another ligand binding domain recognizing a ligand distinct from said IL-23R. In one embodiment, said ligand binding domain is a bifunctional antibody recognizing both the IL-23R and the distinct ligand.

In one embodiment, the Treg cells population is obtained by in vitro differentiation of naïve T cells.

The present invention also relates to a nucleic acid sequence encoding a CAR as described hereinabove, wherein said nucleic acid sequence comprises (i) a nucleic acid sequence of an extracellular IL-23R binding domain, (ii) optionally a nucleic acid sequence of an extracellular hinge domain, (iii) optionally a nucleic acid sequence of a transmembrane domain, (iv) one or more nucleic acid sequence(s) of n intracellular signaling domain and (v) optionally a nucleic acid sequence of a Tag and or a leader sequence.

Another object of the invention is a vector comprising the nucleic acid sequence encoding a CAR as described hereinabove.

Examples of vectors that may be used in the present invention include, but are not limited to, a DNA vector, a RNA vector, a plasmid, a phagemid, a phage derivative, an animal virus and a cosmid.

Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses.

In general, a suitable vector contains an origin of replication functional in at least one organism, a promoter sequence, convenient restriction endonuclease sites, and one or more selectable markers, (e.g., WO01/96584; WO01/29058; and U.S. Pat. No. 6,326,193 incorporated herein by reference).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional transcriptionally active elements, e.g., promoters and enhancers, may regulate the frequency of transcriptional initiation. Typically, regarding core promote, these are located in the region 30-110 bp upstream of the start site, although a number of promoters have recently been shown to contain functional elements downstream of the start site as well, and enhancers elements are generally located 500-2000 bp upstream of the start site. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1a (EF-1a). Another example of a suitable promoter is phosphoglycerate kinase (PGK) promoter. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked to when such expression is desired, or turning off the expression when expression is not desired. Examples of inducible promoters include, but are not limited to a metallothionine promoter, a glucocorticoid promoter, a progesterone promoter, and a tetracycline promoter. In addition, bi-directional promoters allowing efficient and coordinate expression of two or more genes may also be of interest in the present invention. Examples of bi-directional promoters include but are not limited to the promoters described by Luigi Naldini in US2006200869, incorporated herein by reference, disclosing a bi-directional promoter comprising i) a first minimal promoter sequence derived from cytomegalovirus (CMV) or mouse mammary tumor virus (MMTV) genomes and ii) a full efficient promoter sequence derived from an animal gene.

In order to assess the expression of a CAR polypeptide or portions thereof, the expression vector to be introduced into a T cell can also contain either a selectable marker gene such as CD34 or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

In some embodiments of the invention, suicide gene technology may be used. Different suicide gene technologies are described in the art depending on their mechanism of action (Jones et al. Frontiers in Pharmacology, 2014 (5): 254). Examples of gene-directed enzyme prodrug therapy (GDEPT) converting a nontoxic drug to a toxic drug include herpes simplex virus thymidine kinase (HSV-TK) and cytosine deaminase (CD). Other examples are chimeric proteins composed of a drug binding domain linked to apoptotic components such as for example the inducible Fas (iFas) or the inducible Caspase 9 (iCasp9) systems. Other examples include systems mediated by therapeutic antibodies such as inducing overexpression of c-myc at the surface of the engineered cell to induce their deletion by administration of an anti-c-myc antibody. The use of EGFR is described as a similar system compared to the c-myc system. In one embodiment, the suicide gene technology used is the technology described in WO2013153391 or WO2016120216 (incorporated herein by reference). WO2013153391 describes a polypeptide comprising a marker moiety (such as, for example, a minimal epitope of CD34) and a suicide moiety, wherein the suicide moiety comprises a minimal epitope based on an epitope from CD20, such that cells expressing said polypeptide can be selectively killed using a lytic antibody such as, for example, Rituximab. More particularly, said peptide may have the formula St-R1-S1-Q-S2-R2 wherein St is a stalk sequence which, when the polypeptide is expressed at the surface of a target cell, causes the R and Q epitopes to be projected from the cell surface; R1 and R2 are a Rituximab-binding epitope; S1 and S2 are optional spacer sequences, which may be the same or different; and Q is a QBEND-10-binding epitope. An example of such a peptide is SEQ ID NO: 76: CPYSNPSLCSGGGGSELPTQGTFSNVSTNVSPAKPTT-TACPYSNPSLCSGGGGSP APRPPTPAPTIA-SQPLSLRPEACRPAAGGAVHTRGLDFACDIYI-WAPLAGTCGVL LLSLVITLYCNHRNRRRVCKCPRPW. WO2016120216 describes a CAR comprising an extracellular binding domain (scFv) modified to allow cell sorting and cell depletion, wherein said modification consists of inserting one or more selected epitopes within the scFv, said epitopes having a specificity to be recognized by one or more specific antibody(ies). In particular, said selected epitope may be an epitope from CD20, such that cells expressing said CAR can be selectively killed using a lytic antibody such as, for example, Rituximab.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

In one embodiment, the T cells of the invention are modified through the introduction of RNA. In one embodiment, an in vitro transcribed RNA CAR can be introduced to a cell as a form of transient transfection. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention.

In one embodiment, the DNA to be used for PCR contains an open reading frame. The DNA can be from a naturally occurring DNA sequence from the genome of an organism. In one embodiment, the DNA is a full-length gene of interest or a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from more than one organism.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art.

"Forward primers" are primers that contain a region of nucleotides that are substantially complementary to nucleotides on the DNA template that are upstream of the DNA sequence that is to be amplified. "Upstream" is used herein to refer to a location 5', to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA. The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments, the 5' UTR can be derived from an RNA virus whose RNA genome is stable in cells. In other embodiments, various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In one embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatemeric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270: 1485-65 (2003).

The conventional method of integration of polyA/T stretches into a DNA template is molecular cloning. However, polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination.

Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on RNAs also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7: 1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposome mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

In one embodiment, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In another embodiment, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In another embodiment, the desired CAR can be expressed in the cells by way of transposons.

Prior to expansion and genetic modification of the Treg cells of the invention, a source of T cells is obtained from a subject. T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, cells from the circulating blood of an individual are obtained by leukapheresis.

In one embodiment, the cells collected by leukapheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. After washing, the cells may be resuspended in a variety of biocompatible buffers, such as, for example, $Ca^{2+}$-free, $Mg^{2+}$-free PBS, PlasmaLyte A, or other saline solution with or without buffer. Alternatively, the undesirable components of the leukapheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. Longer incubation times may be used to isolate T cells in any situation where there are few T cells as compared to other cell types. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention.

In another embodiment, it may be desirable to perform the selection procedure and use the "unselected" cells in the activation and expansion process. "Unselected" cells can also be subjected to further rounds of selection. Enrichment of a T cell population by negative selection can be accomplished with a combination of antibodies directed to surface markers unique to the negatively selected cells. One method is cell sorting and/or selection via negative magnetic immuno-adherence or flow cytometry that uses a cocktail of monoclonal antibodies directed to cell surface markers present on the cells negatively selected. For example, to enrich for CD4$^+$ cells by negative selection, a monoclonal antibody cocktail typically includes antibodies to CD14, CD20, CD11b, CD16, HLA-DR, and CD8. In certain embodiments, T regulatory cells are depleted by anti-CD25 conjugated beads or other similar method of selection.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation.

Also contemplated in the context of the invention is the collection of blood samples or leukapheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment, a blood sample or a leukapheresis is taken from a generally healthy subject. In certain embodiments, a blood sample or a leukapheresis is taken from a generally healthy subject who is at risk of developing a disease, but who has not yet developed a disease, and the cells of interest are isolated and frozen for later use. In certain embodiments, the T cells may be expanded, frozen, and used at a later time.

Whether prior to or after genetic modification of the Treg cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and US20060121005, incorporated herein by reference.

Generally, the Treg cells of the invention are expanded by contact with a surface having attached thereto an agent that stimulates a CD3/TCR complex associated signal and a ligand that stimulates a co-stimulatory molecule on the surface of the cells of the Treg cells. In particular, the Treg cells may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either CD4$^+$ T cells, an anti-CD3 antibody and an anti-CD28 antibody may be used. Examples of an anti-CD28 antibody include, without being limited to, 9.3, B-T3, XR-CD28 (Diaclone, Besancon, France). Other expansion methods commonly known in the art can be used (Berg et al., Transplant Proc. 30(8):3975-3977, 1998; Haanen et al., J. Exp. Med. 190(9): 13191328, 1999; Garland et al., J. Immunol Meth. 227(1-2):53-63, 1999).

In certain embodiments, the primary stimulatory signal and the co-stimulatory signal for the Treg cells of the invention may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, US20040101519 and 20060034810, incorporated herein by reference, for artificial antigen presenting cells (aAPCs) that are contemplated for use in activating and expanding T cells in the present invention.

In one embodiment, the two agents are immobilized on beads, either on the same bead, i.e., "cis" or to separate beads, i.e., "trans". By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for CD4$^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti-CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments, the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that results in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle:cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the Treg cells are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the Treg cells of the invention. In one embodiment, the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate that any cell concentration may be used. For example, the target cell may be very rare in the sample and comprise only 0.01% of the sample or the entire sample (i.e., 1000%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about 8 days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, a-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population (Th, $CD4^+$) that is greater than the cytotoxic or suppressor T cell population (Tc, $CD8^+$). Ex vivo expansion of T cells by stimulating CD3 and CD28 receptors produces a population of T cells that prior to about days 8-9 consists predominately of Th cells, while after about days 8-9, the population of T cells comprises an increasingly greater population of Tc cells. Accordingly, depending on the purpose of treatment, infusing a subject with a T cell population comprising predominately of Th cells may be advantageous. Similarly, if an antigen-specific subset of Tc cells has been isolated it may be beneficial to expand this subset to a greater degree. Further, in addition to CD4 and CD8 markers, other phenotypic markers vary significantly, but in large part, reproducibly during the course of the cell expansion process. Thus, such reproducibility enables the ability to tailor an activated T cell product for specific purposes.

In one embodiment of the invention, the T cells may be cultured in the presence of rapamycin in order to obtain regulatory T cells, as described for example in WO2007110785 incorporated herein by reference. Another method to generate regulatory T cells is described in US2016024470 incorporated herein by reference, where T cells are cultured with a T cell receptor (TCR)/CD3 activator such as for example TCR/CD3 antibodies, a TCR co-stimulator activator such as for example CD28, CD137 (4-1 BB), GITR, B7-1/2, CD5, ICOS, OX40, CD40 or CD137 antibodies, and rapamycin.

In one embodiment of the invention, the T cells genetically modified by expression of the CAR may also have been genetically modified by expression of at least one intracellular factor such as ROR-C, Foxp3, Foxo1, T-bet, or Gata 3, c-Maf, AhR. In one embodiment, the genetically modified immune cell of the invention expresses Foxp3. In one embodiment, the genetically modified immune cell of the invention expresses Foxo1.

In one embodiment, the genetically modified Treg cell of the invention can be an allogeneic Treg cell. For example, the allogeneic Treg cell can be a T cell lacking expression of a functional human leukocyte antigen (HLA), e.g., HLA class I and/or HLA class II, and/or a T cell lacking expression of an endogenous HLA.

In one embodiment, the Treg cells as described herein can be engineered such that they do not express a functional HLA on its surface. For example, a Treg cell as described herein can be engineered such that cell surface expression HLA, e.g., HLA class 1 (in particular an HLA-A, HLA-B or HLA-C) and/or HLA class II or non-classical HLA molecules is downregulated.

In another embodiment, the Treg cell can lack a functional TCR and a functional HLA such as HLA class I (in particular an HLA-A, HLA-B or HLA-C) and/or HLA class II.

In another embodiment, a Treg cell described herein can be engineered such that it does not express an endogenous HLA on its surface.

Modified Treg cells that lack expression of a functional TCR and/or HLA can be obtained by any suitable means, including a knock out or knock down of one or more subunit of TCR or HLA. For example, the Treg cell can include a knock down of TCR and/or HLA using siRNA, shRNA, clustered regularly interspaced short palindromic repeats (CRISPR) transcription-activator like effector nuclease (TALEN), zinc finger endonuclease (ZFN), meganuclease (mn, also known as homing endonuclease), or megaTAL (combining a TAL effector with a mn cleavage domain).

In one embodiment, the nucleic acid encoding a CAR as described herein is inserted at a specific locus in the genome of a Treg, such as, for example, at the locus of a gene to be deleted. In one embodiment, the nucleic acid encoding a CAR as described herein is inserted within a HLA locus, thereby resulting in the inhibition of HLA expression.

In one embodiment, TCR expression and/or HLA expression can be inhibited using siRNA or shRNA that targets a nucleic acid encoding a TCR and/or HLA in a T cell. Expression of siRNA and shRNAs in T cells can be achieved using any conventional expression system, e.g., such as a lentiviral expression system. Exemplary shRNAs that downregulate expression of components of the TCR are described, e.g., in US2012/0321667. Exemplary siRNA and shRNA that downregulate expression of HLA class I and/or HLA class II genes are described, e.g., in US2007/0036773.

"CRISPR" or "CRISPR to TCR and/or HLA" or "CRISPR to inhibit TCR and/or HLA" as used herein refers to a set of clustered regularly interspaced short palindromic repeats, or a system comprising such a set of repeats. "Cas", as used herein, refers to a CRISPR-associated protein. A "CRISPR/Cas" system refers to a system derived from CRISPR and Cas which can be used to silence or mutate a TCR and/or HLA gene.

Naturally-occurring CRISPR/Cas systems are found in approximately 40% of sequenced eubacteria genomes and 90% of sequenced archaea. Grissa et al. (2007) BMC Bioinformatics 8: 172. This system is a type of prokaryotic immune system that confers resistance to foreign genetic elements such as plasmids and phages and provides a form of acquired immunity. Barrangou et al. (2007) Science 315: 1709-1712; Marragini et al. (2008) Science 322: 1843-1845. The CRISPR/Cas system has been modified for use in gene editing (silencing, enhancing or changing specific genes) in eukaryotes such as mice or primates. Wiedenheft et al. (2012) Nature 482: 331-8. This is accomplished by introducing into the eukaryotic cell a plasmid containing a specifically designed CRISPR and one or more appropriate Cas. The CRISPR sequence, sometimes called a CRISPR locus, comprises alternating repeats and spacers. In a naturally-occurring CRISPR, the spacers usually comprise sequences foreign to the bacterium such as a plasmid or phage sequence; in the TCR and/or HLA CRISPR/Cas system, the spacers are derived from the TCR or HLA gene sequence. RNA from the CRISPR locus is constitutively expressed and processed by Cas proteins into small RNAs. These comprise a spacer flanked by a repeat sequence. The RNAs guide other Cas proteins to silence exogenous genetic elements at the RNA or DNA level. Horvath et al. (2010) Science 327: 167-170; Makarova et al. (2006) Biology Direct 1: 7. The spacers thus serve as templates for RNA molecules, analogously to siRNAs. Pennisi (2013) Science 341: 833-836. The CRISPR/Cas system can thus be used to edit a TCR and/or HLA gene (adding or deleting a basepair), or introducing a premature stop which thus decreases expression of a TCR and/or HLA. The CRISPR/Cas system can alternatively be used like RNA interference, turning off HLA gene in a reversible fashion. In a mammalian cell, for example, the RNA can guide the Cas protein to a TCR and/or HLA promoter, sterically blocking RNA polymerases.

Artificial CRISPR/Cas systems can be generated which inhibit TCR and/or HLA, using technology known in the art, e.g., that described in US20140068797, and Cong (2013) Science 339: 819-823. Other artificial CRISPR/Cas systems that are known in the art may also be generated which inhibit TCR and/or HLA, e.g., that described in Tsai (2014) Nature Biotechnol., 32:6 569-576, U.S. Pat. Nos. 8,871,445; 8,865, 406; 8,795,965; 8,771,945; and 8,697,359.

"TALEN" or "TALEN to TCR and/or HLA" or "TALEN to inhibit TCR and/or HLA" refers to a transcription activator-like effector nuclease, an artificial nuclease which can be used to edit the TCR and/or HLA gene. TALENs are produced artificially by fusing a TAL effector DNA binding domain to a DNA cleavage domain. Transcription activator-like effectors (TALEs) can be engineered to bind any desired DNA sequence, including a portion of the TCR and/or HLA gene. By combining an engineered TALE with a DNA cleavage domain, a restriction enzyme can be produced which is specific to any desired DNA sequence, including a TCR and/or HLA sequence. These can then be introduced into a cell, wherein they can be used for genome editing. Boch (2011) Nature Biotech. 29: 135-6; and Boch et al. (2009) Science 326: 1509-12; Moscou et al. (2009) Science 326: 3501.

TALEs are proteins secreted by *Xanthomonas* bacteria. The DNA binding domain contains a repeated, highly conserved 33-34 amino acid sequence, with the exception of the 12th and 13th amino acids. These two positions are highly variable, showing a strong correlation with specific nucleotide recognition. They can thus be engineered to bind to a desired DNA sequence. To produce a TALEN, a TALE protein is fused to a nuclease (N), which is a wild-type or mutated FokI endonuclease. Several mutations to FokI have been made for its use in TALENs; these, for example, improve cleavage specificity or activity. Cermak et al. (2011) Nucl. Acids Res. 39: e82; Miller et al. (2011) Nature Biotech. 29: 143-8; Hockemeyer et al. (2011) Nature Biotech. 29: 731-734; Wood et al. (2011) Science 333: 307; Doyon et al. (2010) Nature Methods 8: 74-79; Szczepek et al. (2007) Nature Biotech. 25: 786-793; and Guo et al. (2010)/. Mol. Biol. 200: 96. The FokI domain functions as a dimer, requiring two constructs with unique DNA binding domains for sites in the target genome with proper orientation and spacing. Both the number of amino acid residues between the TALE DNA binding domain and the FokI cleavage domain and the number of bases between the two individual TALEN binding sites appear to be important parameters for achieving high levels of activity. Miller et al. (2011) Nature Biotech. 29: 143-8. A HLA TALEN can be used inside a cell to produce a double-stranded break (DSB). A mutation can be introduced at the break site if the repair mechanisms improperly repair the break via non-homologous end joining. For example, improper repair may introduce a frame shift mutation. Alternatively, foreign DNA can be introduced into the cell along with the TALEN; depending on the sequences of the foreign DNA and chromosomal sequence, this process can be used to correct a defect in the TCR and/or HLA gene or introduce such a defect into a wt TCR and/or HLA gene, thus decreasing expression of HLA. TALENs specific to sequences in TCR and/or HLA can be constructed using any method known in the art, including various schemes using modular components. Zhang et al. (2011) Nature Biotech. 29: 149-53; Geibler et al. (2011) PLoS ONE 6: e19509.

"ZFN" or "Zinc Finger Nuclease" or "ZFN to TCR and/or HLA" or "ZFN to inhibit TCR and/or HLA" refer to a zinc finger nuclease, an artificial nuclease which can be used to edit the TCR and/or HLA gene. Like a TALEN, a ZFN comprises a FokI nuclease domain (or derivative thereof) fused to a DNA-binding domain. In the case of a ZFN, the DNA-binding domain comprises one or more zinc fingers. Carroll et al. (2011) Genetics Society of America 188: 773-782; and Kim et al. (1996) Proc. Natl. Acad. Sci. USA 93: 1156-1160. A zinc finger is a small protein structural motif stabilized by one or more zinc ions. A zinc finger can comprise, for example, Cys2His2 (SEQ ID NO: 75), and can recognize an approximately 3-bp sequence. Various zinc fingers of known specificity can be combined to produce multi-finger polypeptides which recognize about 6, 9, 12, 15 or 18-bp sequences. Various selection and modular assembly techniques are available to generate zinc fingers (and combinations thereof) recognizing specific sequences, including phage display, yeast one-hybrid systems, bacterial one-hybrid and two-hybrid systems, and mammalian cells.

Like a TALEN, a ZFN must dimerize to cleave DNA. Thus, a pair of ZFNs are required to target non-palindromic DNA sites. The two individual ZFNs must bind opposite strands of the DNA with their nucleases properly spaced apart. Bitinaite et al. (1998) Proc. Natl. Acad. Sci. USA 95: 10570-5. Also like a TALEN, a ZFN can create a double-stranded break in the DNA, which can create a frame-shift mutation if improperly repaired, leading to a decrease in the expression and amount of TCR and/or HLA in a cell. ZFNs can also be used with homologous recombination to mutate in the TCR and/or HLA gene. ZFNs specific to sequences in TCR and/or HLA can be constructed using any method known in the art. See, e.g., Provasi (2011) Nature Med. 18: 807-815; Torikai (2013) Blood 122: 1341-1349; Cathomen et al. (2008) Mol. Ther. 16: 1200-7; Quo et al. (2010)/. Mol. Biol. 400: 96; US2011/0158957; and US2012/0060230.

"Meganuclease" or "meganuclease to TCR and/or HLA" or "meganuclease to inhibit TCR and/or HLA" refers to a monomeric endonuclease with large (>14 base pairs) recognition sites, which can be used to edit the TCR and/or HLA gene. Meganucleases (mn) are monomeric proteins with innate nuclease activity that are derived from bacterial homing endonucleases and engineered for a unique target site. Homing endonucleases are DNA-cleaving enzymes that can generate double strand breaks at individual loci in their host genomes, and thereby drive site-specific gene conversion events. (Stoddard, Structure. 2011 Jan. 12; 19(1):7-15). Despite their small size, homing endonucleases recognize long DNA sequences (typically 20 to 30 base pairs). Homing endonucleases are extremely widespread and are found in microbes, as well as in phages and viruses. The LAGLIDADG and His-Cys box enzymes (which are the most sequence-specific of these enzymes) rely upon antiparallel β-sheets that dock into the major grooves of their DNA target sites (Flick et al., 1998; Jurica et al., 1998). There they establish a collection of sequence-specific and non-specific contacts that are distributed nonuniformly across multiple consecutive basepairs (Chevalier et al., 2003; Scalley-Kim et al., 2007).

The LAGLIDADG homing endonuclease (LHE) family is the primary source of the engineered enzymes used for gene targeting applications. The LHE family is primarily encoded within archaea and in the chloroplast and mitochondrial genomes of algae and fungi (Chevalier et al., 2005; Dalgaard et al., 1997; Sethuraman et al., 2009). Meganucleases that possess a single conserved LAGLIDADG motif (SEQ ID NO: 58) per protein chain form homodimeric proteins that cleave palindromic and nearly palindromic DNA target sequences, while those that contain two such motifs per protein chain form larger, pseudo-symmetric monomers that can target completely asymmetric DNA sequences.

Meganucleases can be engineered to target TCR and/or HLA and thus create a double-stranded break in the DNA, which can create a frame-shift mutation if improperly repaired, leading to a decrease in the expression and amount of TCR and/or HLA in a cell.

"MegaTAL" or "megaTAL to TCR and/or HLA" or "megaTAL to inhibit TCR and/or HLA" refers to an artificial nuclease, which can be used to edit the TCR and/or HLA gene. MegaTALs are hybrid monomeric nucleases obtained through the fusion of minimal TAL (transcription activator-like) effector domains to the N-terminus of meganucleases derived from the LAGLIDADG homing endonuclease family (Nucleic Acids Res. 2014 February; 42(4):2591-601; Takeuchi et al, Methods Mol Biol. 2015; 1239:105-32. doi: 10.1007/978-1-4939-1862-1_6). MegaTALs thus consist of a site-specific meganuclease cleavage head with additional affinity and specificity provided by a TAL effector DNA binding domain.

MegaTALs can be engineered to target TCR and/or HLA and thus create a double-stranded break in the DNA, which can create a frame-shift mutation if improperly repaired, leading to a decrease in the expression and amount of TCR and/or HLA in a cell.

While not wishing to be bound by any particular theory, in some embodiments, a therapeutic T cell has short term persistence in a patient, due to shortened telomeres in the T cell; accordingly, transfection with a telomerase gene can lengthen the telomeres of the T cell and improve persistence of the T cell in the patient. See Carl June, "Adoptive T cell therapy for cancer in the clinic", Journal of Clinical Investigation, 117: 1466-1476 (2007). Thus, in an embodiment, the genetically modified Treg cell, ectopically expresses a telomerase subunit, e.g., the catalytic subunit of telomerase, e.g., TERT, e.g., hTERT. In some aspects, this disclosure provides a method of producing a CR-expressing cell, comprising contacting a cell with a nucleic acid encoding a telomerase subunit, e.g., the catalytic subunit of telomerase, e.g., TERT, e.g., hTERT. The cell may be contacted with the nucleic acid before, simultaneous with, or after being contacted with a construct encoding a CR.

The present invention further relates to a method for obtaining a Treg cell of the invention, wherein said method comprises transducing at least one Treg cell with a nucleic acid encoding a CAR as described hereinabove, and optionally expanding the transduced cells.

In one embodiment, the method is an ex vivo method.

In one embodiment, the method for obtaining Treg cells of the invention comprises:
  an isolation step of Treg cells from a PBMC population (e.g., recovered by leukapheresis)
  a genetic modification step wherein a nucleic acid sequence encoding a CAR as described hereinabove is introduced or transferred within the Treg cells,
  optionally an expansion step,
  optionally a washing step and,
  optionally a freezing step.

In one embodiment, the genetic modification step(s) correspond(s) to a gene disruption step, a gene correction step or a gene addition step, preferably a gene addition step. In one embodiment, the genetic modification step(s) is carried out by a method selected from the group comprising, but not limited to, transfection, transduction or gene editing.

Examples of methods of gene editing that may be used in the present invention include, but are not limited to, methods based on engineered nucleases, methods based on recombinant Adeno-Associated Virus (or AAV), methods based on Transposons (e.g., Sleeping Beauty transposon system), methods based on homologous recombination, conditional targeting using site-specific recombinases (e.g., Cre-LoxP and Flp-FRT systems), and Multiplex Automated Genomic Engineering (MAGE).

Non-limiting examples of engineered nucleases include, but are not limited to, clustered regularly interspaced short palindromic repeats (CRISPR) transcription-activator like effector nuclease (TALEN), zinc finger endonuclease (ZFN), meganuclease (mn, also known as homing endonuclease), or megaTAL (combining a TAL effector with a mn cleavage domain).

In one embodiment, the method for obtaining Treg cells of the invention comprises:
  an isolation step of Treg cells from a PBMC population (e.g., recovered by leukapheresis)
  a transduction or transfection step with a vector comprising a nucleic acid sequence encoding a CAR as described hereinabove,
  optionally an expansion step,
  optionally a washing step and,
  optionally a freezing step.

Another object of the invention is a composition comprising, consisting or consisting essentially of at least one Treg cell population of the invention.

In one embodiment, said composition comprises, consists or consists essentially of at least one Treg cell population engineered to express on the cell surface a CAR specific for at least one IL-23R as described hereinabove, wherein said CAR comprises (i) an extracellular binding domain specific for IL-23R as described hereinabove, (ii) optionally an extracellular hinge domain as described hereinabove, (iii) optionally a transmembrane domain as described hereinabove, (iv) an intracellular signaling domain as described hereinabove, and, (v) optionally a tag and/or a leader sequence as described hereinabove.

In one embodiment, said composition has been frozen and thawed.

Another object of the invention is a pharmaceutical composition comprising, consisting or consisting essentially of at least one Treg cell population as described hereinabove and at least one pharmaceutically acceptable excipient.

Another object of the invention is a medicament comprising, consisting or consisting essentially of at least one Treg cell population as described hereinabove.

In one embodiment, the pharmaceutical composition or medicament comprises at least one isolated and/or substantially purified Treg cell population of the invention.

In one embodiment, the pharmaceutical composition or medicament comprises a combination of Treg cell populations as described hereinabove (i.e., at least two distinct Treg cell populations of the invention).

In one embodiment, the composition, pharmaceutical composition or medicament of the invention further comprises at least one other Treg cell population, wherein cells of said other Treg cell population express on the cell surface a CAR specific of an antigen, a fragment of an antigen, a variant of an antigen or a mixture thereof.

In one embodiment, the cells of said other Treg cell population express on the cell surface a CAR specific of a food antigen from the common human diet.

In another embodiment, the cells of said other Treg cell population express on the cell surface a CAR specific of an autoantigen, such as, for example, a multiple sclerosis-associated antigen, a joint-associated antigen, an eye-associated antigen, a human HSP antigen, a skin-associated antigen or an antigen involved in graft rejection or GVHD.

In another embodiment, the cells of said other Treg cell population express on the cell surface a CAR specific of an inhaled allergen, an ingested allergen or a contact allergen.

In one embodiment, the cells of said other Treg cell population express on the cell surface a CAR specific of an antigen selected from the group comprising ovalbumin, MOG, type II collagen fragments, variants and mixtures thereof.

In one embodiment, the cells of said other Treg cell population express on the cell surface a CAR specific of ovalbumin, fragments, variants and mixtures thereof.

In another embodiment, the cells of said other Treg cell population express on the cell surface a CAR specific of MOG, fragments, variants and mixtures thereof.

In another embodiment, the cells of said other Treg cell population express on the cell surface a CAR specific of type II collagen, fragments, variants and mixtures thereof.

In another embodiment, the cells of said other Treg cell population express on the cell surface a CAR specific of citrullinated vimentin, citrullinated type II collagen or citrullinated fibrinogen, fragments, variants and mixtures thereof.

In another embodiment, the cells of said other immune cell population express on the cell surface a CAR specific of HLA-A2, fragments, variants and mixtures thereof.

In one embodiment, the cells of said other Treg cell population express on the cell surface a CAR wherein the extracellular-binding domain of said CAR is a protein or fragments or variants thereof, such as for example, an autoantigen or fragments or variants thereof.

As used herein, the term "consisting essentially of", with reference to a pharmaceutical composition or medicament, means that the at least one Treg cell population of the invention is the only one therapeutic agent or agent with a biologic activity within said pharmaceutical composition or medicament.

Such compositions and medicaments may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives.

The administration of the compositions may be carried out in any convenient manner, including by aerosol inhalation, injection, ingestion, transfusion, implantation or transplantation. The compositions described herein may be administered to a patient trans arterially, subcutaneously, intradermally, intratumorally, intranodally, intramedullary, intramuscularly, by intravenous (i.v.) injection, or intraperitoneally. In one aspect, the T cell compositions of the present invention are administered to a patient by intradermal or subcutaneous injection.

In one embodiment, the Treg cell populations of the present invention are administered by i.v. injection.

The compositions of the present invention are in one embodiment formulated for intravenous administration.

In another embodiment, the Treg cell populations of the present invention may be injected directly into the site of the autoimmune and/or inflammatory disease or disorder.

The present invention further relates to a Treg cell expressing a CAR of the present invention, to a population of such cells, to a composition, to a pharmaceutical composition or to a medicament as described herein, for use in treating an IL-23R-expressing cell-mediated disease or disorder.

Another object of the invention is thus a method for treating in a subject in need thereof an IL-23R-expressing cell-mediated disease or disorder, wherein said method comprises administering to the subject at least one Treg cell or Treg cell population as described hereinabove.

In one embodiment, the method is a cell therapy method.

In one embodiment, the subject is administered (or is to be administered) with autologous cells. In other words, in one embodiment, the cell therapy is autologous.

In one embodiment, the cell therapy is heterologous.

In another embodiment, the subject is administered (or is to be administered) with allogenic cells. In other words, in one embodiment, the cell therapy is allogenic.

Another object of the present invention is a method for treating in a subject in need thereof an IL-23R-expressing cell-mediated disease or disorder, wherein said method comprises administering to the subject at least one CAR as described herein or nucleic acid encoding a CAR as described herein or vector comprising a CAR as described herein. In one embodiment, the method of the invention is a gene therapy method.

In one embodiment, the IL-23R-expressing cell-mediated disease or disorder is a proinflammatory cell mediated disease or disorder, a Th17-mediated disease or disorder or a γδ T-mediated disease or disorder.

In one embodiment, the IL-23R-expressing cell-mediated disease is an autoimmune disease or disorder and/or an inflammatory disease or disorder.

Examples of IL-23R-expressing cell-mediated diseases or disorders include but are not limited to, Crohn's disease, ulcerative colitis (UC), bullous pemphigoid, lupus (including systemic lupus erythematosus (SLE), lupus nephritis (LN), discoid lupus, lupus erythematosus profundus, Chilbrain lupus erythematosus, tumidus lupus erythematosus, severe systemic lupus erythematosus, acute cutaneous lupus, chronic cutaneous lupus), multiple sclerosis, arthritis (such as, for example, rheumatoid arthritis, reactive arthritis (Reiter syndrome), juvenile idiopathic arthritis, ankylosing spondylitis and psoriatic arthritis), neuromyelitis optica (NMO), autoimmune limbic encephalitis (LE), Hashimoto's disease, N-methyl-D-aspartate receptor (NMDAR) encephalitis, autoimmune hemolytic anemia, pemphigus vulgaris, myasthenia gravis, Graves' disease, idiopathic thrombocytopenic purpura, Goodpasture's syndrome, celiac disease, pernicious anemia, vitiligo, scleroderma, psoriasis, Sjogren's syndrome, Wegener granulomatosis, polymyositis, dermatomyositis, primary biliary cirrhosis, antiphospholipid syndrome, mixed connective tissue disease, Miller Fisher syndrome, Guillain-Barré syndrome, acute motor axonal neuropathy, autoimmune hepatitis, dermatitis herpetiformis, Churg-Strauss disease, microscopic polyangiitis, IgA nephropathy, vasculitis caused by ANCA and other ANCA associated diseases, acute rheumatic fever, pernicious anemia, type 1 diabetes (TID), membranous nephropathy, chronic inflammatory demyelinating polyneuropathy, thrombotic thrombocytopenic purpura, hyperviscosity in monoclonal gammopathies, hemolytic uremic syndrome (atypical, due to antibody to factor H), Wilson disease, fulminant, Lambert-Eaton myasthenic syndrome, RBC alloimmunization in pregnancy, mushroom poisoning, acute disseminated encephalomyelitis, hemolytic uremic syndrome (atypical, due to complement factor mutations), autoimmune hemolytic anemia (life-threatening cold agglutinin disease), myeloma cast nephropathy, post-transfusion purpura, autoimmune hemolytic anemia (warm autoimmune hemolytic anemia), hypertriglyceridemic pancreatitis, thyroid storm, stiff person syndrome, Hemolytic uremic syndrome (typical diarrhea-associated), immune thrombocytopenia, ABO-incompatible solid organ transplantation (SOT), cryoglobulinemia, heparin-induced thrombocytopenia, thyroid storm, chronic inflammatory demyelinating polyradiculoneuropathy, focal segmental glomerulosclerosis and fulminant hepatic failure.

In one embodiment, said IL-23R-expressing cell-mediated disease or disorder is selected from inflammatory bowel disease (such as, for example, Crohn's disease and ulcerative colitis), systemic lupus erythematosus, rheumatoid arthritis, juvenile idiopathic arthritis, Sjögren syndrome, systemic sclerosis, ankylosing spondylitis, Type 1 diabetes, autoimmune thyroid disorders, multiple sclerosis, Myasthenia Gravis, psoriasis, psoriatic arthritis or uveitis.

In one embodiment, IL-23R-expressing cell-mediated disease or disorder is Crohn's disease.

The terms "inflammatory disorder" or "inflammatory disease" are used interchangeably and as used herein refer to any abnormality associated with inflammation.

In one embodiment, the inflammatory condition comprises inflammatory diseases or disorder linked to a cancer.

In one embodiment, the inflammatory condition comprises inflammatory diseases or disorder linked to an autoimmune disease.

Examples of inflammatory diseases or disorders include, but are not limited to, arthritis, rheumatoid arthritis, ankylosing spondylitis, osteoarthritis, psoriatic arthritis, juvenile idiopathic arthritis, juvenile rheumatoid arthritis, arthritis uratica, gout, chronic polyarthritis, periarthritis humeroscapularis, cervical arthritis, lumbosacral arthritis, enteropathic arthritis and ankylosing spondylitis, asthma, dermatitis, psoriasis, scleroderma, polymyositis, dermatomyositis, juvenila dermatomyositis, primary biliary cirrhosis, fibrosis, cystic fibrosis, pulmonary fibrosis, cirrhosis, endomyocardial fibrosis, dediastinal fibrosis, myelofibrosis, retroperitoneal fibrosis, nephrogenic fibrosis, Keloids, scleroderma, arthrofibrosis, post transplantation late and chronic solid organ rejection, multiple sclerosis, systemic lupus erythematosus, lupus nephritis, pemphigus, Pemphigus vulgaris, Pemphigus herpetiformis, Pemphigus vegetans, IgA pemphigus, Pemphigus erythematosus, bullous pemphigoid, Pemphigoid gestationis, Mucous membrane dermatosis, Pemphigoid nodularis, Linear IgA bullous dermatosis, Bullous *Lichen planus*, Epidermolysis bullosa acquisita, autoimmune diabetes, diabetic retinopathy, diabetic nephropathy, diabetic vasculopathy, ocular inflammation, uveitis, rhinitis, ischemia-reperfusion injury, post-angioplasty restenosis, chronic obstructive pulmonary disease (COPD), glomerulonephritis, Graves disease, gastrointestinal allergies, conjunctivitis, atherosclerosis, coronary artery disease, angina, small artery disease, acute disseminated encephalomyelitis, idiopathic thrombocytopenic purpura, multiple sclerosis, systemic sclerosis, antiphospholipid syndrome, Sjoegren's syndrome, autoimmune hemolytic anemia, colitis, Crohn's Disease, ulcerative colitis, Inflammatory Bowel Disease (IBD), embolism, pulmonary embolism, arterial embolism, venous embolism, allergic inflammation, cardiovascular disease, graft-related diseases, graft versus host disease (GVHD), disorders associated with graft transplantation rejection, chronic rejection, and tissue or cell allografts or xenografts, autoimmune diseases, degeneration after trauma, stroke, transplant rejection, allergic conditions and hypersensitivity, e.g., allergic rhinitis, allergic eczema and the like, skin diseases, dermal inflammatory disorders, or any combination thereof.

Examples of skin diseases include, but are not limited to, acne; actinic keratosis; atopic dermatitis; contact dermatitis; decubitus ulcers (bedsores); eczema; erythroderma; hemangioma, such as, for example, hemangioma of childhood; hypertrophic scarring; *Lichen planus*; lichenoid disorders; lymphangiogenesis; psoriasis; pyogenic granulomas; molluscum contagious; neurofibromatosis; rosacea; recessive dystrophic epidermolysis bullosa; scars (keloids); scleroderma; seborrheic keratosis; skin cancers such as angiosarcoma, basal cell carcinoma, hemangioendothelioma, Karposi's sarcoma, malignant melanoma, melanoma, squamous cell carcinoma; skin ulcers; skin damages following skin grafts such as autotransplantation and allotransplantation; Steven-Johnson syndromes and toxic epidermal necrolysis; Sturge-Weber syndrome; tuberous sclerosis; venous ulcers; verruca vulgaris; warts, such as, for example, viral warts; wounds; and the like.

Examples of dermal inflammatory disorders include, but are not limited to, psoriasis, guttate psoriasis, inverse psoriasis, pustular psoriasis, erythroderma psoriasis, acute febrile neutrophilic dermatosis, eczema, asteatotic eczema, dyshidrotic eczema, vesicular palmoplanar eczema, acne vulgaris, atopic dermatitis, contact dermatitis, allergic contact dermatitis, dermatomyositis, exfoliative dermatitis, hand eczema, pompholyx, rosacea, rosacea caused by sarcoidosis, rosacea caused by scleroderma, rosacea caused by Sweet's syndrome, rosacea caused by systemic lupus erythematosus, rosacea caused by urticaria, rosacea caused by zoster-associated pain, Sweet's disease, neutrophilic hidradenitis, sterile pustulosis, drug eruptions, seborrheic dermatitis, *Pityriasis rosea*, cutaneous kikuchi disease, pruritic urticarial papules and plaques of pregnancy, Stevens-Johnson syndrome and toxic epidermal necrolysis, tattoo reactions, Wells syndrome (eosinophilic cellulitis), reactive arthritis (Reiter's syndrome), bowel-associated dermatosis-arthritis syndrome, rheumatoid neutrophilic dermatosis, neutrophilic eccrine hidradenitis, neutrophilic dermatosis of the dorsal hands, balanitis circumscripta plasmacellularis, balanoposthitis, Behcet's disease, erythema annulare centrifugum, erythema dyschromicum perstans, erythema multiforme, granuloma annulare, hand dermatitis, *Lichen nitidus, Lichen planus, Lichen sclerosus* et atrophicus, *Lichen simplex* chronicus, *Lichen spinulosus*, nummular dermatitis, pyoderma gangrenosum, sarcoidosis, subcorneal pustular dermatosis, urticaria, and transient acantholytic dermatosis.

In another embodiment, the CAR of the present invention may be used for treating in a subject in need thereof an autoimmune disease or disorder, wherein said method comprises administering to the subject at least one CAR as described herein or nucleic acid encoding a CAR as described herein or vector comprising a CAR as described herein.

Examples of autoimmune diseases include, but are not limited to, lupus (e.g., lupus erythematosus, lupus nephritis), Hashimoto's thyroiditis, primary myxedema, Graves' disease, pernicious anemia, autoimmune atrophic gastritis, Addison's disease, diabetes (e.g. insulin dependent diabetes mellitus, type I diabetes mellitus, type II diabetes mellitus), good pasture's syndrome, myasthenia gravis, pemphigus, Crohn's disease, sympathetic ophthalmia, autoimmune uveitis, multiple sclerosis, autoimmune hemolytic anemia, idiopathic thrombocytopenia, primary biliary cirrhosis, chronic action hepatitis, ulcerative colitis, Sjogren's syndrome, rheumatic diseases (e.g., rheumatoid arthritis), polymyositis, scleroderma, psoriasis, and mixed connective tissue disease.

In another embodiment, the CAR of the present invention may be used for treating in a subject in need thereof an allergic disease or disorder, wherein said method comprises administering to the subject at least one CAR as described herein or nucleic acid encoding a CAR as described herein or vector comprising a CAR as described herein.

Examples of allergic diseases include but are not limited to, allergic diseases against an inhaled allergen, an ingested allergen or a contact allergen. Other examples of allergic diseases include but are not limited to, allergic asthma, hypersensitivity lung diseases, food allergy, atopic dermatitis, allergic rhinitis, allergic rhinoconjunctivitis, chronic urticaria, delayed-type hypersensitivity disorders and systematic anaphylaxis.

In another embodiment, the CAR of the present invention may be used for treating in a subject in need thereof a cancer, wherein said method comprises administering to the subject at least one CAR as described herein or nucleic acid encoding a CAR as described herein or vector comprising a CAR as described herein.

As used herein, a "cancer" may be any cancer that is associated with a surface antigen or cancer marker.

Examples of cancers include but are not limited to, acute lymphoblastic leukemia (ALL), acute myeloid leukemia (AML), adenoid cystic carcinoma, adrenocortical, carcinoma, AIDS-related cancers, anal cancer, appendix cancer, astrocytomas, atypical teratoid/rhabdoid tumor, central nervous system, B-cell leukemia, lymphoma or other B cell malignancies, basal cell carcinoma, bile duct cancer, bladder cancer, bone cancer, osteosarcoma and malignant fibrous histiocytoma, brain stem glioma, brain tumors, breast cancer, bronchial tumors, burkitt lymphoma, carcinoid tumors, central nervous system cancers, cervical cancer, chordoma, chronic lymphocytic leukemia (CLL), chronic myelogenous leukemia (CML), chronic myeloproliferative disorders, colon cancer, colorectal cancer, craniopharyngioma, cutaneous t-cell lymphoma, embryonal tumors, central nervous system, endometrial cancer, ependymoblastoma, ependymoma, esophageal cancer, esthesioneuroblastoma, ewing sarcoma family of tumors extracranial germ cell tumor, extragonadal germ cell tumor extrahepatic bile duct cancer, eye cancer fibrous histiocytoma of bone, malignant, and osteosarcoma, gallbladder cancer, gastric (stomach) cancer, gastrointestinal carcinoid tumor, gastrointestinal stromal tumors (GIST), soft tissue sarcoma, germ cell tumor, gestational trophoblastic tumor, glioma, hairy cell leukemia, head and neck cancer, heart cancer, hepatocellular (liver) cancer, histiocytosis, hodgkin lymphoma, hypopharyngeal cancer, intraocular melanoma, islet cell tumors (endocrine pancreas), kaposi sarcoma, kidney cancer, langerhans cell histiocytosis, laryngeal cancer, leukemia, lip and oral cavity cancer, liver cancer (primary), lobular carcinoma in situ (LCIS), lung cancer, lymphoma, macroglobulinemia, male breast cancer, malignant fibrous histiocytoma of bone and osteosarcoma, medulloblastoma, medulloepithelioma, melanoma, merkel cell carcinoma, mesothelioma, metastatic squamous neck cancer with occult primary midline tract carcinoma involving NUT gene, mouth cancer, multiple endocrine neoplasia syndromes, multiple myeloma/plasma cell neoplasm, mycosis fungoides, myelodysplastic syndromes, myelodysplastic/myeloproliferative neoplasms, myelogenous leukemia, chronic (CML), Myeloid leukemia, acute (AML), myeloma, multiple, myeloproliferative disorders, nasal cavity and paranasal sinus cancer, nasopharyngeal cancer, neuroblastoma, non-hodgkin lymphoma, non-small cell lung cancer, oral cancer, oral cavity cancer, oropharyngeal cancer, osteosarcoma and malignant fibrous histiocytoma of bone, ovarian cancer, pancreatic cancer, papillomatosis, paraganglioma, paranasal sinus and nasal cavity cancer, parathyroid cancer, penile cancer, pharyngeal cancer, pheochromocytoma, pineal parenchymal tumors of intermediate differentiation, pineoblastoma and supratentorial primitive neuroectodermal tumors, pituitary tumor, plasma cell neoplasm/multiple myeloma, pleuropulmonary blastoma, pregnancy and breast cancer, primary central nervous system (CNS) lymphoma, prostate cancer, rectal cancer, renal cell (kidney) cancer, renal pelvis and ureter, transitional cell cancer, retinoblastoma, rhabdomyosarcoma, salivary gland cancer, sarcoma, sezary syndrome, small cell lung cancer, small intestine cancer, soft tissue sarcoma, squamous cell carcinoma, squamous neck cancer, stomach (gastric) cancer, supratentorial primitive neuroectodermal tumors, t-cell lymphoma, cutaneous, testicular cancer, throat cancer, thymoma and thymic carcinoma, thyroid cancer, transitional cell cancer of the renal pelvis and ureter, trophoblastic tumor, ureter and renal pelvis cancer, urethral cancer, uterine cancer, uterine sarcoma, vaginal cancer, vulvar cancer, Waldenstrom macroglobulinemia, Wilms Tumor.

In some aspects, the cancer is a B cell malignancy. Examples of B cell malignancies include, but are not limited to, Non-Hodgkin's Lymphomas (NHL), Diffuse Large B Cell Lymphoma (DLBCL), Small lymphocytic lymphoma (SLL/CLL), Mantle cell lymphoma (MCL), Follicular lymphoma (FL), Marginal zone lymphoma (MZL), Extranodal (MALT lymphoma), Nodal (Monocytoid B-cell lymphoma), Splenic, Diffuse large cell lymphoma, B cell chronic lymphocytic leukemia/lymphoma, Burkitt's lymphoma and Lymphoblastic lymphoma.

In one embodiment, the subject (e.g., human) receives an initial administration of the Treg cell population of the invention, and one or more subsequent administrations, wherein the one or more subsequent administrations are administered less than 15 days, e.g., 14, 13, 12, 11, 10, 9, 8, 7, 6, 5, 4, 3, or 2 days after the previous administration.

In one embodiment, a therapeutically effective amount of Treg cells is administered or is to be administered to the subject.

In one embodiment, the amount of Treg cells of the at least one immune cell population of the invention administered to the subject is at least of $10^2$, $10^3$, $10^4$, $10^5$, $10^6$, $10^7$, $10^8$ or $10^9$ cells.

In one embodiment, the amount of Treg cells of the at least one Treg cell population of the invention administered to the subject ranges from about $10^2$ to about $10^9$, from about $10^3$ to about $10^8$, from about $10^4$ to about $10^7$, or from about $10^5$ to about $10^6$ cells.

In another embodiment, the amount of Treg cells of the at least one Treg cell population of the invention administrated to the subject ranges from about $10^6$ to about $10^9$, from about $10^6$ to $10^7$, from about $10^6$ to $10^8$, from about $10^7$ to $10^9$, from about $10^7$ to $10^8$, from about $10^8$ to $10^9$. In another embodiment, the amount of Treg cells of the at least one Treg cell population of the invention administrated to the subject is about $10^6$, about $10^7$, about $10^8$, or is about $10^9$.

In one embodiment, the amount of Treg cells of the at least one Treg cell population of the invention administered to the subject is at least of $10^2$, $10^1$, $10^4$, $10^5$, $10^6$, $10^7$, $10^8$ or $10^9$ cells/kg body.

In one embodiment, the amount of Treg cells of the at least one Treg cell population of the invention administered to the subject ranges from about $10^4$ to $10^9$ cells/kg body weight or $10^5$ to $10^8$ cells/kg body weight, including all integer values within those ranges.

In one embodiment, the subject receives more than one administration of the at least one Treg cell population of the invention per week, e.g., 2, 3, or 4 administrations of the at least one Treg cell population of the invention are administered per week to the subject.

In one embodiment, the at least one Treg cell population is administered to the subject in need thereof in combination with an active agent. According to one embodiment, the at least one Treg cell population is administered before, at the same time or after the administration of an active agent.

Another object of the present invention is an article of manufacture containing materials useful for the treatment of an IL-23R-expressing cell-mediated disease or disorder.

The article of manufacture may comprise a container and a label or package insert on or associated with the container. Suitable containers include, for example, bottles, vials, syringes, pouch, etc. The containers may be formed from a variety of materials such as glass or plastic. The container holds a composition which is effective for treating the IL-23R-expressing cell-mediated disease or disorder, such as an autoimmune and/or inflammatory disease or disorder, and may have a sterile access port (for example the container may be an intravenous solution bag or a vial having a stopper pierceable by a hypodermic injection needle). At least one active agent in the composition is a Treg cell population of the invention.

The label or package insert may indicate that the composition is used for treating an IL-23R-expressing cell-mediated disease or disorder.

The article of manufacture, label or package insert may further comprise instructional material for administering the Treg cell population of the invention to the patient. Additionally, the article of manufacture may further comprise a second container comprising a pharmaceutically acceptable buffer, such as, for example, bacteriostatic water for injection (BWFI), phosphate-buffered saline, Ringer's solution and dextrose solution. It may further include other materials desirable from a commercial and user standpoint, including other buffers, diluents, filters, needles, and syringes.

Another object of the invention is a kit comprising at least one Treg cell population of the invention. By "kit" is intended any manufacture (e.g., a package or a container) comprising at least one Treg cell population of the invention. The kit may be promoted, distributed, or sold as a unit for performing the methods of the present invention. Furthermore, any or all of the kit reagents may be provided within containers that protect them from the external environment, such as in sealed containers.

The kits may also contain a package insert describing the kit and methods for its use. Kits are also provided that are useful for various purposes (e.g., for treating an IL-23R-expressing cell-mediated disease or disorder). Kits can be provided which contain the Treg cell population of the invention. As with the article of manufacture, the kit may comprise a container and a label or package insert on or associated with the container. The container holds a composition comprising at least one Treg cell population of the invention. Additional containers may be included that contain, e.g., diluents and buffers. The label or package insert may provide a description of the composition as well as instructions for the intended use.

EXAMPLES

Figures 1, 2:
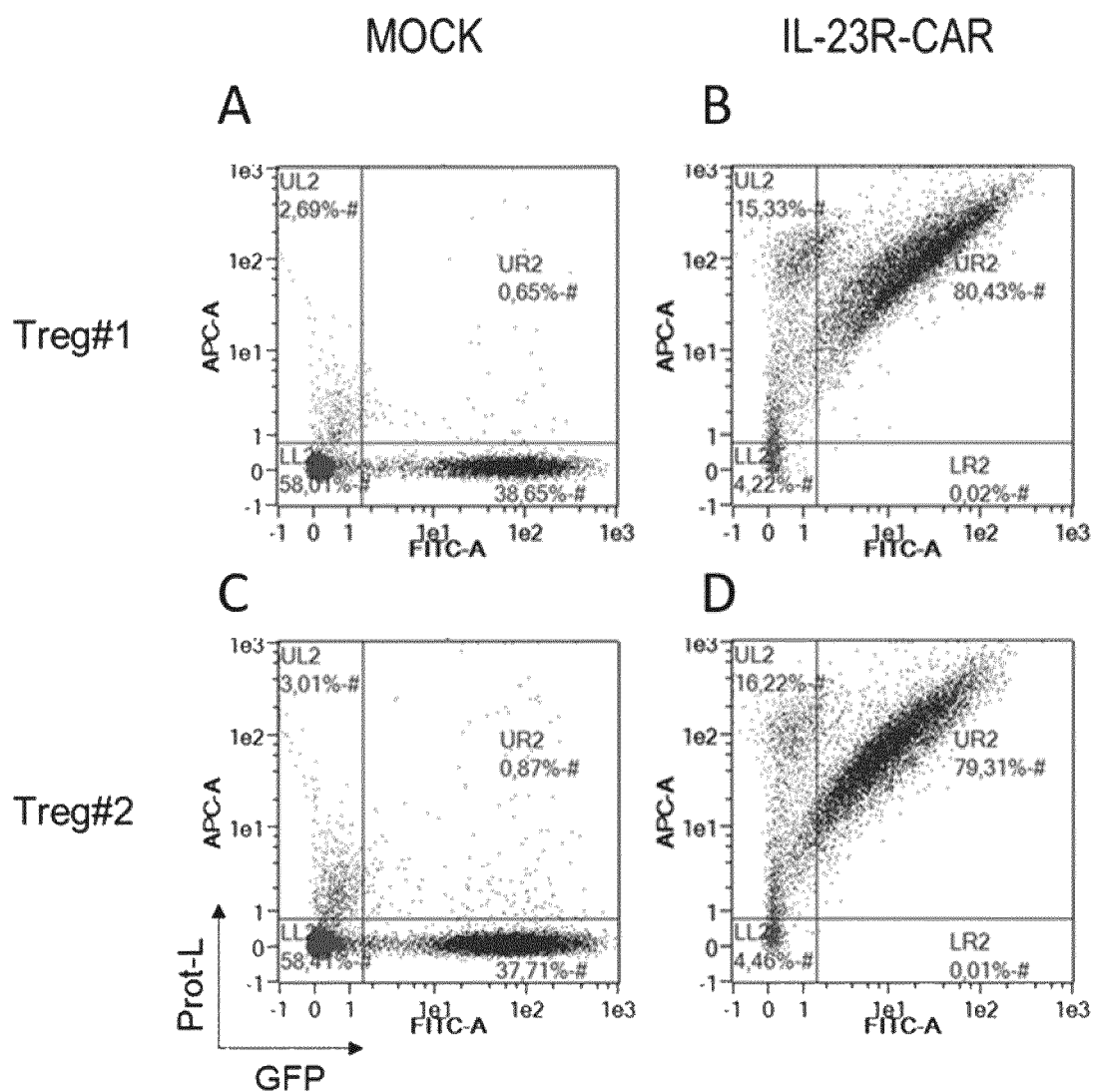
FIG. 1 represents a schematic view of an anti-IL-23R Chimeric Antigen Receptor (CAR) construct of the invention (such as, for example, the CAR having a sequence SEQ ID NO: 54). The anti-IL23R CAR comprises a human CD8 leader sequence (CD8), a scFv directed against the human IL23R (αIL23R), a CD8 hinge (CD8 linker), a transmembrane domain derived from the human CD8 alpha (CD8 TM), an activation domain of human 4-1BB (4-IBB) and CD3 zeta (CD3Z). The CAR construct is in frame with a P2A-GFP coding sequence.
FIG. 2 is a combination of dot plots of flow cytometry showing Treg transduction efficacy and membrane expression of the CAR. Results obtained with two Treg clones are shown (representative results). Transduction efficacy was assessed by GFP expression in flow cytometry. Membrane expression of the CAR was assessed by protein-L staining in flow cytometry. Results obtained with two Treg clones (clone 1: A-B; clone 2: C-D) are shown (representative results). (A, C) GFP-transduced Treg (MOCK), (B, D): Treg transduced with IL-23R CAR of the invention.

The present invention is further illustrated by the following examples.

Example 1: Anti-IL23R CAR humanTreg

Material and Methods
Cells and Reagents

HEK293T cells (LentiX, Ozyme, France) were cultured in DMEM medium supplemented with 10% Fetal Bovine Serum (FBS).

FoxP3 Treg isolation

CD4$^+$CD25$^+$CD127$^{low}$ Treg cells were freshly isolated from buffy coats using the EasySep™ Human CD4$^+$ CD127$^{low}$CD25$^+$ Regulatory T Cell Isolation Kit from StemCell. After isolation purity was assessed by FoxP3 staining. Isolated Treg cells were plated at 5×10$^5$ cells per well in a 24-well plate (Costar) into X-VIVO 15 media (Lonza) and activated with anti-CD3/anti-CD28 coated microbeads (Invitrogen, Carlsbad, CA) at a 1:1 bead-to-cell ratio. Tregs cells received rapamycin (100 ng/ml) at the same time that the activation. At day 2, 5, 7, and 9 IL-2 was added (1000 units/ml, Miltenyi).

CAR Construct

The anti-IL23R CAR construct comprises a human CD8 leader sequence (aa1-22) (e.g., having the sequence SEQ ID NO: 39), a scFv directed against the human IL23R (e.g., having the sequence SEQ ID NO: 55), a CD8 hinge (e.g., having the sequence SEQ ID NO: 13) and transmembrane domain derived from the human CD8 alpha (aa138-206) (e.g., having the sequence SEQ ID NO: 21), an activation domain of human 4-1BB (aa214-255) (e.g., having the sequence SEQ ID NO: 29) and CD3 zeta (aa52-164) (e.g., having the sequence SEQ ID NO: 26). The CAR construct is in frame with a P2A-GFP coding sequence.

Vector and Titration

The CAR constructs were produced using a classical 4-plasmid lentiviral system. Briefly, HEK293T cells were transfected with a third-generation lentiviral transfer vector (pTX266), the plasmid expressing HIV-1 gagpol (pMDLgpRRE), the plasmid expressing HIV-1 rev (pRSV.Rev) and the plasmid expressing VSV-G, the envelope glycoprotein of the vesicular stomatitis virus (pMD2.G). One-day post-transfection, viral supernatants were harvested, concentrated by centrifugation, aliquoted and frozen at −80° C. for long term storage. The infectious titers, expressed as the number of transducing units per milliliter (TU/ml), were obtained after transduction of Jurkat T cells with a serial dilution of viral supernatants and transduction efficiency evaluated after 3 days by monitoring the green fluorescent protein (GFP) expression using flow cytometry.

Lentiviral Transduction

Tregs were transduced 2 days after their activation with a chimeric receptor composed of the sequence leader of the CD8 followed by an scFv anti-IL-23R. This extracellular domain is linked to the signaling sequence via the hinge and the transmembrane region of the human CD8. The signaling sequence is composed to the intracellular domain of 4-1BB followed by intracellular human CD3ζ chain. Briefly transduction was carried out by loading 0.5×10$^7$ Transduction unit (TU) per ml to each well. After 6 hours at 37° C., viral particles were removed by washout. The plates were then incubated at 37° C. with 5% CO2. The efficiency of transduction (assessed by GFP expression) and the level of chimeric receptors at cell surface (assessed by protein-L staining) were checked 5 days after transduction.

Protein-L Staining

The quantification of cell surface CAR expression was performed by labelling the CAR with APC-conjugated protein L and analyzed using flow cytometry. Briefly, after wash, cells were resuspended in 0.2 ml of the ice-cold wash buffer (PBS 4% BSA) and incubated with 5 μg of protein L at 4° C. for 20 minutes. Cells were washed with 0.2 ml of the ice-cold wash buffer three times, and then incubated (in the dark) with 1 μl of APC-conjugated streptavidin in 0.2 ml of the wash buffer. Immunofluorescence staining was analyzed on a MACQUANT (Miltenyi) using MacsQuantify software (Miltenyi).

Results

Human Treg cells were sorted using a kit from Stem Cell based on CD4$^+$CD127$^{low}$CD25$^+$ profile and pre-stimulated with anti-CD3/anti-CD28 coated beads as well as IL-2 for 2 days prior to viral transduction. Treg were transduced with a chimeric antigen receptor (IL-23R-CAR) composed of a single chain variable fragment (scFv) of an anti-IL-23R and is linked to a signaling sequence via the hinge and the transmembrane region of the human CD8, to the intracellular part of a human 4-1BB, which was in turn fused to an intracellular human CD3ζ chain (see FIG. 1).

Viral supernatant was added to 5×10$^5$ stimulated Tregs in 250 μl Xvivo medium. Cells were cultured for 7 days with addition of IL-2 every 2 days. Transduction efficiency assessed by GFP expression in FoxP3 positive cells show around 80% of GFP$^+$ and all of them expressed the CAR at cell surface (FIG. 2).

We then examined the ability of transduced Tregs to be activated via the IL-23R CAR. Tregs were stimulated with plate-coated recombinant human IL-23R or beads-coated IL-23R. 24 h after stimulation the status of activation was analyzed through CD69 expression in flow cytometry.

Figure 3:
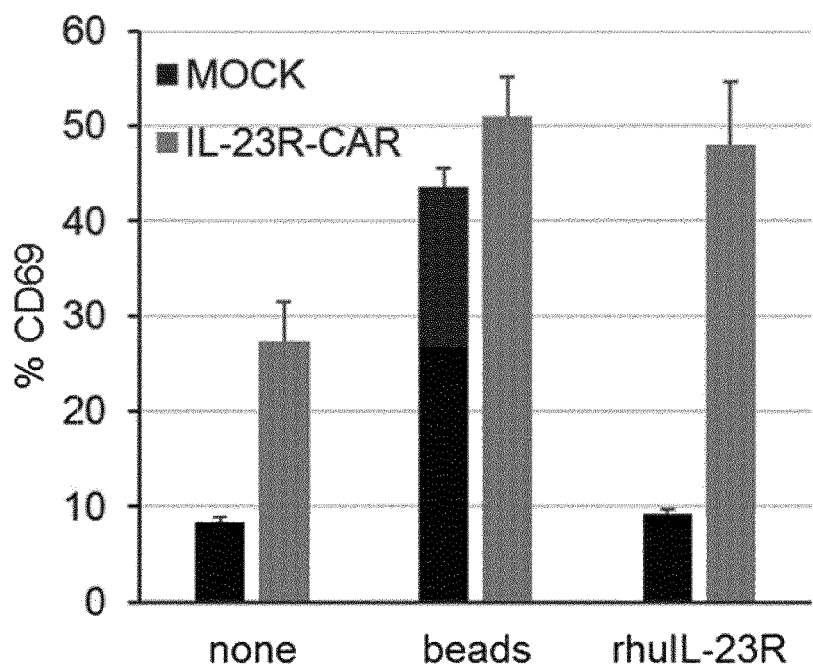
FIG. 3 is a histogram showing the IL-23R CAR mediated Treg activation. Treg cell activation was assessed by CD69 expression by flow cytometry 24 h after activation of untransduced Treg (MOCK) or IL-23R-CAR transduced Treg (IL-23R-CAR) with coated recombinant human IL-23R (rhuIL-23R) (5 µg/ml) or with CD3/CD28 coated beads (at a 1:1 bead-to-cell ratio). Results were expressed as mean of 2 different donors±SEM.

CD69 up-regulation in presence of plate or beads coated recombinant human IL-23R demonstrates that IL-23R CAR transduced Tregs can be activated through CAR triggering (FIG. 3).

Example 2: Anti-IL23R CAR Murine Treg

Material and Methods
FoxP3 Treg Isolation

CD4$^+$CD25$^+$ murine Treg cells were freshly isolated from spleen of C57B16 mice using the Regulatory T Cell Isolation Kit from life technologies. After isolation purity was assessed by FoxP3 staining. Isolated Treg cells were plated at 5×10$^5$ cells per well in a 24-well plate into RPMI 10% SVF and activated with anti-CD3/anti-CD28-coated microbeads (Invitrogen) at a 2:1 bead-to-cell ratio. Tregs cells received rapamycin (50 ng/ml) at the same time that the activation and at Day4. Finally, at day 0, 2, 4, IL-2 was added (1000 units/ml).

CAR Construct

The anti-murine IL23R CAR construct used in this experiment (e.g., having the nucleic acid sequence SEQ ID NO: 77 and the amino acid sequence SEQ ID NO: 78) comprises a human CD8 leader sequence (CD8), a cross reactive scFv directed against the human/murine IL23R (αIL23R), hinge and transmembrane domains derived from the murine CD28 (mCD28 linker & mCD28 TM), an activation domain of murine CD28 (mCD28) and murine CD3 zeta (mCD3Z).

Vector and Titration

The CAR constructs were produced using a classical 4-plasmid lentiviral system. Briefly, HEK293T cells were transfected with a third-generation lentiviral transfer vector, the plasmid expressing HIV-1 gagpol (pMDLgpRRE), the plasmid expressing HIV-1 rev (pRSV.Rev) and the plasmid expressing Eco-MLV, the envelope glycoprotein of the ecotropic murine leukemia virus (pCMV-Eco). One-day post-transfection, viral supernatants were harvested, concentrated by centrifugation, aliquoted and frozen at −80° C. for long term storage. The infectious titers, expressed as the number of transducing units per milliliter (TU/ml), were obtained after transduction of Jurkat T cells with a serial dilution of viral supernatants and transduction efficiency evaluated after 3 days by monitoring the green fluorescent protein (GFP) expression using flow cytometry.

Lentiviral Transduction

Tregs were transduced 2 days after their activation with a chimeric receptor composed of the sequence leader of the CD8 followed by an scFv anti-IL-23R. This extracellular domain is linked to the signaling sequence via the hinge and the transmembrane region of the human CD8. The signaling sequence is composed to the intracellular domain of 4-1BB followed by intracellular human CD3ζ chain. Briefly transduction was carried out by loading $0.5\times10^7$ TU/ml to each well. After 6 hours at 37° C., viral particles were removed by washout. The plates were then incubated at 37° C. with 500 $CO_2$. The efficiency of transduction (assessed by GFP expression) and the level of chimeric receptors at cell surface (assessed by protein-L staining) were checked 5 days after transduction.

Activation Assay of CAR-Tregs

The activation assay was performed at day 7 of the culture. Briefly, $0.05\times10^6$ Treg were seeded in 96 U bottom plate alone or in presence of anti CD28/antiCD3 coated beads (in a 2 to 1 Treg to beads ratio), or in presence of plate-coated murine IL-23R (1 μg/ml) or in presence of dose escalation of beads coated human as well as murine IL-23R in a 200 μl final volume. After 24 h at 37° C., 5% $CO_2$, cells were stained for CD4 and CD69 and then analyzed using flow cytometry.

Suppression Assay of T Cell Proliferation

The suppression assay was performed at day 7 of the culture. Splenocytes from OTII mice (Tg for OVA specific TCR) were cocultured for 4 days in presence of ovalbumin (100 μg/ml), untransduced Tregs (Poly Treg) or IL-23RmCAR Tregs with or without murine IL-23R coated beads or anti-CD3/CD28 beads. At day 4, cells were harvested, and proliferation of CD4 from splenocytes was assessed by flow cytometry through the determination of dye 450 dilution. The percentage of inhibition of Tconv proliferation was calculated as followed:

$$100 - \frac{\%\ of\ Tconv\ proliferation\ in\ presence\ of\ CAR-Treg \times 100}{\%\ of\ Tconv\ proliferation\ in\ absence\ of\ CAR-Treg}$$

Imiquimod-Induced Psoriasis-Like Skin Inflammation

Mice (C57BL/6) at 8 to 10 wk of age received a daily topical dose of 62.5 mg of commercially available IMQ cream (5%) (Aldara; 3M Pharmaceuticals) on the shaved back for 7 consecutive days, Control mice were treated similarly with a control vehicle cream (Vaseline Lanette cream; Fagron). AT day 2, Anti-IL-23 (100 ug) was injected intra peritoneally and $8\times10^6$ Treg per mice (Poly or aIL-23R-CAR) were injected intravenously. All mice were sacrificed at Day 7. To score the severity of inflammation of the back skin, an objective scoring system was developed based on the clinical Psoriasis Area and Severity Index (PASI). Redness, scaling, and thickening were scored independently on a scale from 0 to 4: 0, none; 1, slight; 2, moderate; 3, marked; 4, very marked. The level of redness was scored using a scoring table with red taints. The cumulative score (redness plus scaling plus thickening) served as a measure of the severity of inflammation (scale 0-12). All experiments were approved by the animal ethics committee according to French legislation on animal experiments.

Results

Figure 4:
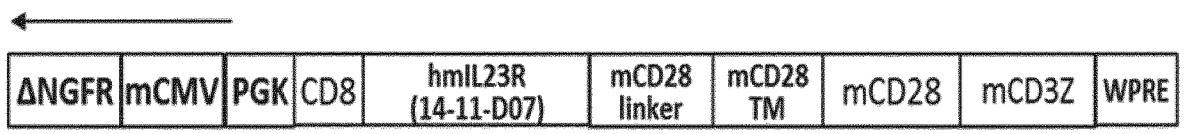
FIG. 4 is a schematic view of an anti-murine IL-23R Chimeric Antigen Receptor (CAR) construct of the invention. The anti-IL23R CAR comprises a human CD8 leader sequence (CD8), a cross reactive scFv directed against the human/murine IL23R (αIL23R), a hinge and transmembrane domain derived from the murine CD28 (mCD28 linker & mCD28 TM), an activation domain of murine CD28 (mCD28) and murine CD3 zeta (mCD3Z).

After isolation, murine Treg (mTreg) cells were pre-stimulated with antiCD3/anti-CD28 coated beads as well as IL-2 for 2 days prior to viral transduction. mTreg were transduced with a chimeric antigen receptor (IL-23R-mCAR) composed of a single chain variable fragment (scFv) of the cross-reactive hu/ms anti-IL-23R and is linked to a signaling sequence via the hinge and the transmembrane region of the murin CD8 to the intracellular part of a murin CD28 which was in turn fused to an intracellular murin CD3ζ chain (FIG. 4).

Figure 5:
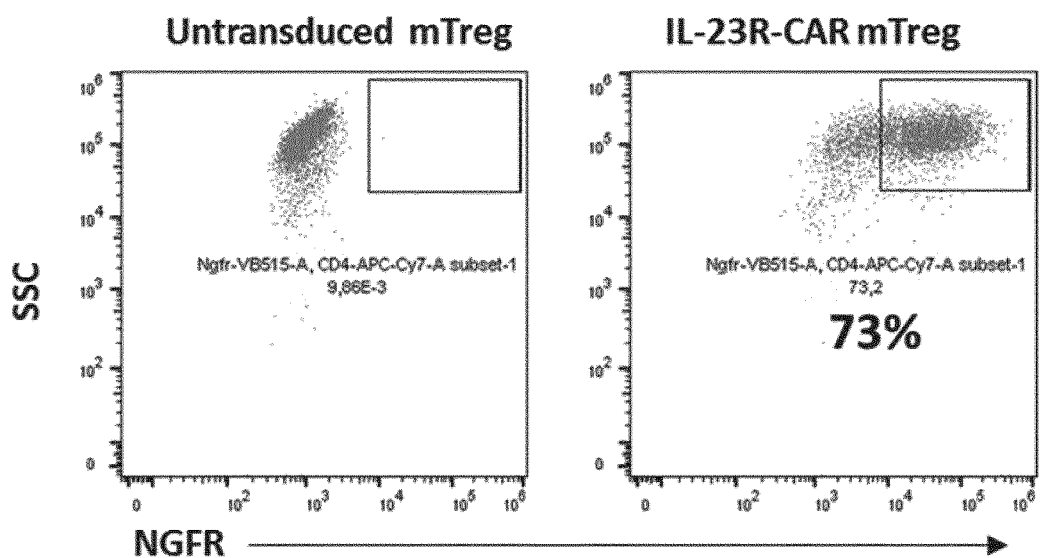
FIG. 5 is a combination of dot plots of flow cytometry showing murine Treg transduction efficacy. Transduction efficacy was assessed by NGFR staining in flow cytometry.

Viral supernatant was added to $5\times10^5$ stimulated Tregs in 250 μl Xvivo medium. Cells were cultured for 7 days with addition of IL-2 every 2 days. Transduction efficiency as well as CAR expression at cell surface, was assessed by NGFR staining and showed around 70% of transduced cells expressing CAR at cell surface. (FIG. 5).

Figure 6:
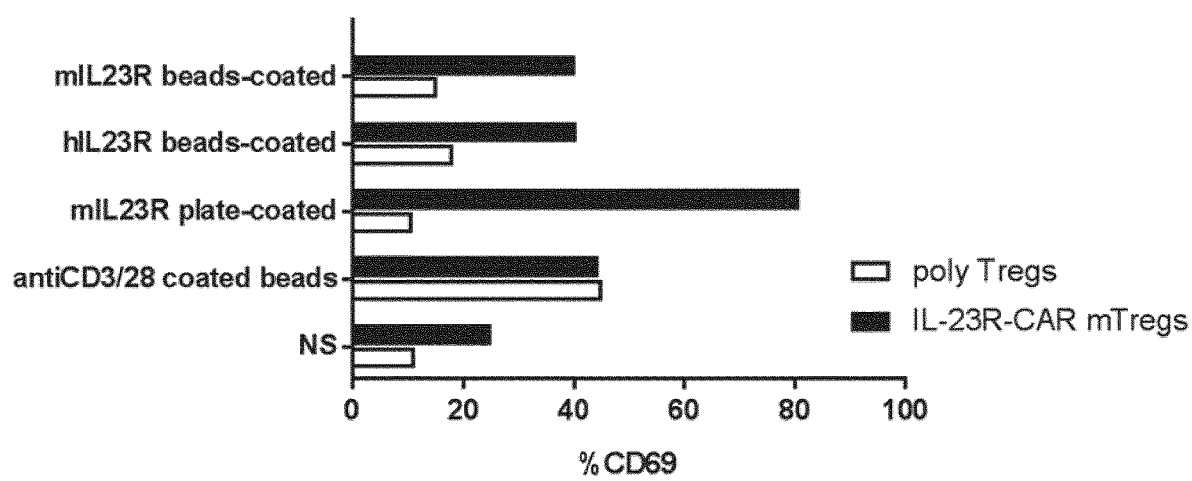
FIG. 6 is a histogram showing the IL-23R CAR mediated murine Treg (mTreg) activation. mTreg cell activation was assessed by CD69 expression by flow cytometry 24 h after activation of untransduced mTreg (Poly Treg) or IL-23R-CAR transduced mTreg (IL-23R-CAR mTreg) with CD3/CD28 coated beads, or plate-coated recombinant murine IL-23R (mIL23R plate-coated 1 µg/ml) or beads coated with human or murine IL-23R.

Then, the ability of transduced mTregs to be activated via the IL-23R CAR was examined. mTregs were stimulated with plate-coated recombinant murine IL-23R or beads-coated human as well as murine IL-23R. 24 h after stimulation the status of activation was analyzed through CD69 expression in flow cytometry. CD69 up-regulation in presence of plate or beads coated recombinant human/murine IL-23R demonstrates that IL-23R CAR transduced mTregs can be activated through CAR triggering (FIG. 6).

Figure 7A:
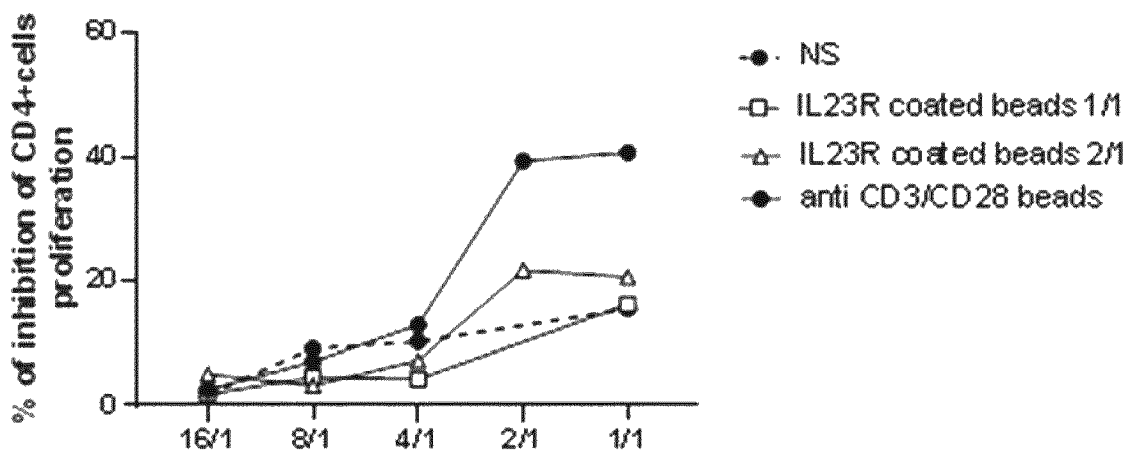
FIG. 7 is a graph showing that IL-23R CARs mTregs exhibit efficient CAR-mediated suppressive activity in vitro. Contact dependent suppression mediated by untransduced Treg (A) or IL-23R-CAR Treg (B) stimulated through their CAR with mIL-23R coated beads (ratios 1:1 or 2:1), with CD3/CD28 coated beads or unstimulated (NS) was evaluated by measuring the proliferation of conventional T cells (Tconv) in flow cytometry.
Figure 7B:
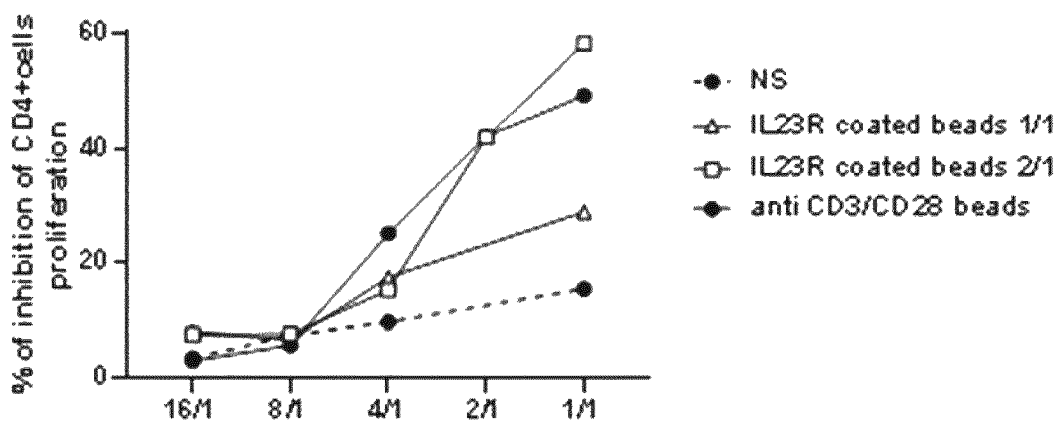

Finally, the important feature is that $FoxP3^+$ Treg cells transduced with IL-23R-CAR maintain their suppressive contact dependent function (FIGS. 7A and B) through the CAR triggering.

Figure 8:
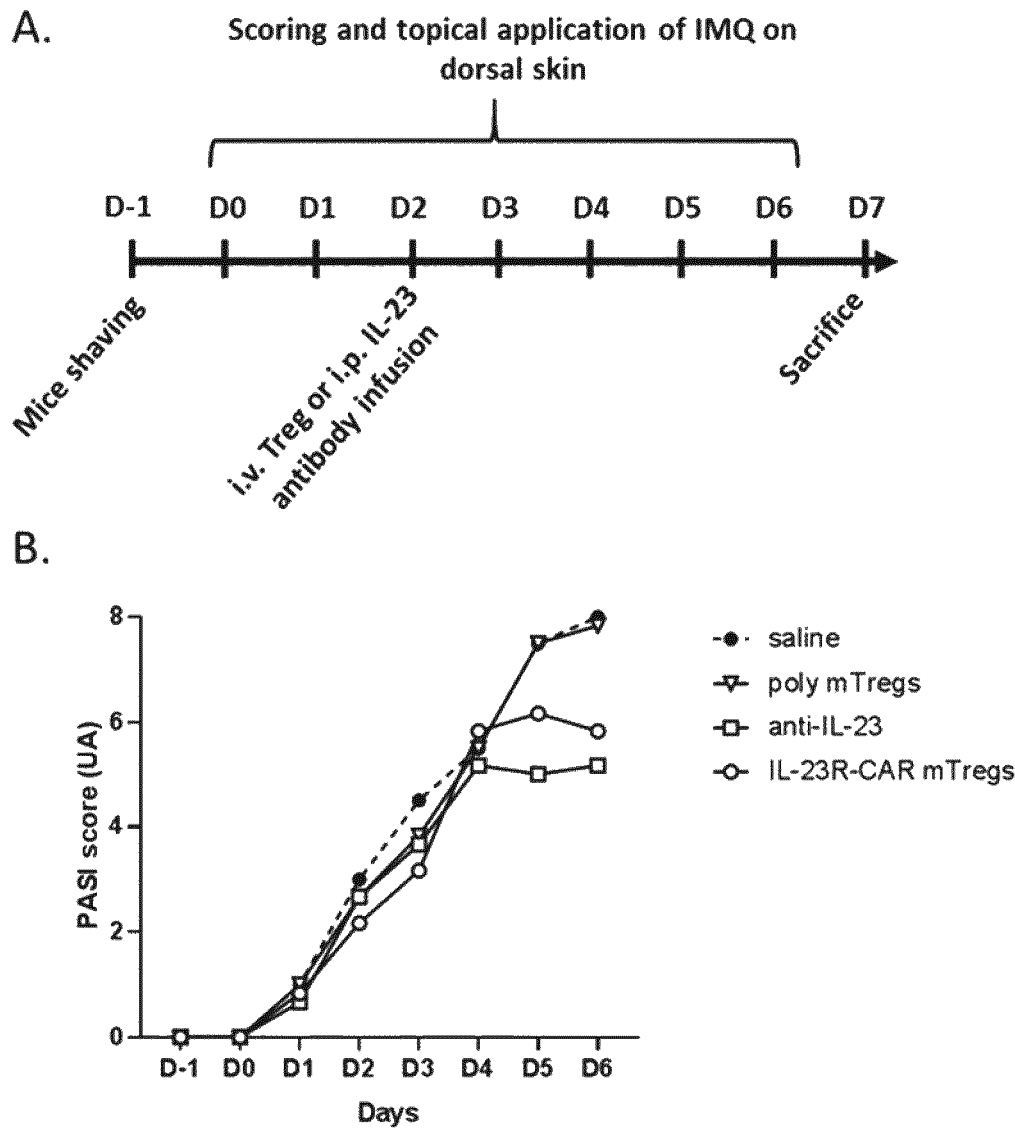
FIG. 8 is a combination of graphs showing (A) a schematic view of the in vivo experimental design and (B) the PASI score of imiquimod-induced skin inflammation model of different group of mice: untreated (saline), treated i.p. with anti-IL-23, treated i.v. with poly-mTreg ($8\times10^6$) or IL-23R-CAR mTreg ($8\times10^6$).

Finally, as shown in FIGS. 8 A and B, the IL-23R CAR Treg was tested for its activity in vivo in the imiquimod-induced skin inflammation model, a model described to be driven by the IL-23/IL-23R axis. An anti-IL-23 antibody (white squares) confirmed that the blockade of IL-23 induce a reduction of clinical score. Interestingly, IL-23R-CAR mTreg (white circles) are also capable to induce a reduction, two days after their i.v. infusion, of clinical score whereas polyclonal Treg (white triangle) have no effect on the clinical course.

The invention claimed is:

1. A chimeric antigen receptor (CAR) specific for at least one IL-23 receptor (IL-23R), wherein said CAR comprises:
   i) an extracellular binding domain, wherein said binding domain binds to said IL-23R,
   ii) optionally an extracellular hinge domain,
   iii) a transmembrane domain,
   iv) an intracellular signaling domain, and,
   v) optionally a tag and/or a leader sequence.

2. The CAR according to claim 1, wherein the extracellular binding domain comprises an scFv fragment directed against said IL-23R.

3. The CAR according to claim 1, wherein the extracellular binding domain comprises an scFv fragment directed against said IL-23R, wherein said scFv comprises a heavy chain variable domain (VH) and a light chain variable domain (VL) and optionally a linker between the VH and the VL, wherein
   the VH has the sequence of SEQ ID NO: 37, and
   the VL has a sequence selected from the group consisting of SEQ ID NOs: 38, 46 and 56.

4. The CAR according to claim 1, wherein the extracellular binding domain comprises an scFv fragment directed against said IL-23R, wherein said scFv has the sequence of SEQ ID NO: 55.

5. The CAR according to claim 1, wherein the hinge domain is a hinge region of human CD8.

6. The CAR according to claim 1, wherein the hinge domain is a hinge region of human CD8 having the sequence of SEQ ID NO: 13.

7. The CAR according to claim 1, wherein the transmembrane domain is a transmembrane domain derived from the human CD8a.

8. The CAR according to claim 1, wherein the transmembrane domain is a transmembrane domain derived from human CD8a having the sequence of SEQ ID NO: 21.

9. The CAR according to claim 1, wherein the intracellular signaling domain comprises a costimulatory signaling domain of a molecule selected from the group consisting of 4-1BB, ICOS, CD27, OX40, CD28, CTLA4 and PD-1 and a T cell primary signaling human CD3 zeta.

10. The CAR according to claim 1, wherein the intracellular signaling domain comprises a costimulatory signaling domain of human 4-1BB having the sequence of SEQ ID NO: 29 and a T cell primary signaling human CD3 zeta having the sequence of SEQ ID NO: 26.

11. The CAR according to claim 1, wherein the intracellular signaling domain comprises a costimulatory signaling domain of human CD28 having the sequence of SEQ ID NO: 31 and a T cell primary signaling human CD3 zeta having the sequence of SEQ ID NO: 26.

12. The CAR according to claim 1, comprising
   i) an anti-IL-23R scFv comprising a VH that has the sequence of SEQ ID NO: 37 and a VL that has the sequence of SEQ ID NO: 38, linked by a $(G45)_3$ linker (SEQ ID NO: 3),
   ii) a hinge domain derived from CD8a,
   iii) a human CD8a transmembrane domain,
   iv) an intracellular signaling domain comprising a costimulatory signaling domain of a molecule selected from the group consisting of 4-1BB, ICOS, CD27, OX40, CD28, CTLA4 and PD-1, and a human CD3 zeta domain, and
   v) optionally a tag and/or a leader sequence.

13. A chimeric antigen receptor (CAR) specific for at least one IL-23 receptor (IL-23R), comprising
   i) an anti-IL-23R scFv comprising a VH that has the sequence of SEQ ID NO: 37 and a VL that has the sequence of SEQ ID NO: 38, linked by a $(G-45)_3$ linker (SEQ ID NO: 3),
   ii) a hinge domain derived from CD8a having the sequence of SEQ ID NO: 13,
   iii) a human CD8a transmembrane domain having the sequence of SEQ ID NO: 21,
   iv) an intracellular signaling domain comprising a human 4-1BB signaling domain having the sequence of SEQ ID NO: 29 and a human CD3 zeta domain having the sequence of SEQ ID NO: 26, and
   v) optionally a tag and/or a leader sequence.

14. A chimeric antigen receptor (CAR) specific for at least one IL-23 receptor (IL-23R), comprising
   i) an anti-IL-23R scFv comprising a VH that has the sequence of SEQ ID NO: 37 and a VL that has the sequence of SEQ ID NO: 38, linked by a $(G-45)_3$ linker (SEQ ID NO: 3),
   ii) a hinge domain derived from CD8a having the sequence of SEQ ID NO: 13,
   iii) a human CD8a transmembrane domain having the sequence of SEQ ID NO: 21,
   iv) an intracellular signaling domain comprising a CD28 signaling domain having the sequence of SEQ ID NO: 31 and a human CD3 zeta domain having the sequence of SEQ ID NO: 26, and
   v) optionally a tag and/or a leader sequence.

15. A nucleic acid sequence encoding a CAR according to claim 1.

16. A T cell population, engineered to express on the cell surface a CAR according to claim 1.

17. The T cell population according to claim 16, wherein said T cell population is a regulatory T cell (Treg) population.

18. The T cell population according to claim 17, wherein said Treg population is selected from the group consisting of $CD4^+CD25^+Foxp3^+$ Treg, Tr1 cells, TGF-β secreting Th3 cells, regulatory NKT cells, regulatory γδ T cells, regulatory $CD8^+$ T cells, and double negative regulatory T cells.

19. A method for treating an IL-23R-expressing cell-mediated disease or disorder in a subject in need thereof, comprising administering to the subject a T cell population according to claim 16, wherein said IL-23R-expressing cell-mediated disease or disorder is an autoimmune and/or inflammatory disease and/or disorder selected from the group consisting of inflammatory bowel diseases, systemic lupus erythematosus, multiple sclerosis, psoriasis, psoriatic arthritis and uveitis.

20. The method according to claim 19, wherein said IL-23R expressing cell-mediated disease or disorder is Crohn's disease or ulcerative colitis.

* * * * *